(12) United States Patent (10) Patent No.: US 12,569,352 B2
El-Naggar (45) Date of Patent: Mar. 10, 2026

(54) MINIMALLY INVASIVE ROBOTIC ASSISTED TRANS-FACET LUMBAR INTERBODY FUSION

(71) Applicant: Amr Osman El-Naggar, Somerset, KY (US)

(72) Inventor: Amr Osman El-Naggar, Somerset, KY (US)

(73) Assignee: Amr Osman El-Naggar, Somerset, KY (US)

( * ) Notice: Subject to any disclaimer, the term of this patent is extended or adjusted under 35 U.S.C. 154(b) by 26 days.

(21) Appl. No.: 18/428,295

(22) Filed: Jan. 31, 2024

(65) Prior Publication Data

US 2024/0299186 A1 Sep. 12, 2024

Related U.S. Application Data

(63) Continuation of application No. 17/586,769, filed on Jan. 27, 2022, now Pat. No. 11,925,566.

(60) Provisional application No. 63/166,966, filed on Mar. 26, 2021, provisional application No. 63/142,228, filed on Jan. 27, 2021.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4405* (2013.01); *A61F 2/4611* (2013.01); *A61F 2002/30579* (2013.01)

(58) Field of Classification Search
CPC ................................................ A61F 2/44–447
See application file for complete search history.

(56) References Cited

U.S. PATENT DOCUMENTS

| | | | | |
|---|---|---|---|---|
| 6,083,225 | A * | 7/2000 | Winslow ............ | A61B 17/1757 |
| | | | | 606/279 |
| 6,805,697 | B1 | 10/2004 | Helm et al. | |
| H2261 | H * | 8/2011 | Simmons, Jr. ...... | A61F 2/30734 |
| | | | | 623/17.11 |
| 9,445,918 | B1 | 9/2016 | Lin et al. | |
| 2006/0111782 | A1* | 5/2006 | Petersen ............ | A61L 27/3608 |
| | | | | 623/17.11 |
| 2011/0087329 | A1* | 4/2011 | Poulos .................... | A61F 2/442 |
| | | | | 606/279 |
| 2011/0230970 | A1* | 9/2011 | Lynn ..................... | A61F 2/4601 |
| | | | | 623/17.16 |
| 2011/0245924 | A1* | 10/2011 | Kuslich .................. | A61F 2/441 |
| | | | | 623/17.16 |
| 2011/0301710 | A1* | 12/2011 | Mather .................. | A61F 2/447 |
| | | | | 623/17.16 |
| 2013/0096683 | A1 | 4/2013 | Kube | |
| 2013/0310942 | A1* | 11/2013 | Abdou .................. | A61F 2/4611 |
| | | | | 623/17.16 |
| 2015/0018886 | A1 | 1/2015 | Ali | |
| 2020/0405501 | A1* | 12/2020 | Orozco Castillo ... | A61F 2/4611 |

* cited by examiner

*Primary Examiner* — Nicholas J Plionis
(74) *Attorney, Agent, or Firm* — Meunier Carlin & Curfman LLC

(57) ABSTRACT

A method for performing lumbar interbody fusion surgery may include forming an access corridor through a facet joint of a patient, removing disc material from a disc space of the patient via one or more instruments advanced through the access corridor, and advancing an interbody device through the access corridor and into the disc space.

20 Claims, 71 Drawing Sheets

MINIMALLY INVASIVE ROBOTIC ASSISTED TRANS-FACET LUMBAR INTERBODY FUSION

CROSS-REFERENCE TO RELATED APPLICATIONS

This application is a continuation of U.S. application Ser. No. 17/586,769, filed on Jan. 27, 2022, which claims priority to and the benefit of U.S. Provisional Patent Application No. 63/142,228, filed on Jan. 27, 2021, and U.S. Provisional Patent Application No. 63/166,966, filed on Mar. 26, 2021, the disclosures of which are expressly incorporated herein by reference in their entirety.

FIELD OF THE DISCLOSURE

The present disclosure relates generally to spinal surgery and more particularly to techniques for performing minimally invasive robotic assisted trans-facet lumbar interbody fusion surgery.

BACKGROUND OF THE DISCLOSURE

Lumbar interbody fusion surgery has been utilized for many years using different approaches, including posterior lumbar interbody fusion (PLIF), trans-foraminal lumbar interbody fusion (TLIF), anterior lumbar interbody fusion (ALIF), direct lateral interbody fusion (DLIF), and extreme lateral interbody fusion (XLIF), among others. Although these approaches may be suitable in certain instances, they may present certain drawbacks, including exposure of the neural elements, risk of nerve root injury, risk of epidural scarring or arachnoiditis, risk of infection, and significant disturbance of the paraspinal muscles. A need therefore exists for improved techniques for performing lumbar interbody fusion surgery, which may overcome one or more of these drawbacks associated with existing approaches.

SUMMARY OF THE DISCLOSURE

The present disclosure provides techniques for performing trans-facet lumbar interbody fusion surgery. In one embodiment, a method for performing lumbar interbody fusion surgery may include forming an access corridor through a facet joint of a patient, removing disc material from a disc space of the patient via one or more instruments advanced through the access corridor, and advancing an interbody device through the access corridor and into the disc space.

In some embodiments, forming the access corridor may include forming an entry point of the access corridor in a middle aspect of the facet joint midway between an inferior articular facet of a vertebra above the disc space and a superior articular facet of a vertebra below the disc space. In some embodiments, forming the access corridor may include advancing a first drill bit through a middle aspect of the facet joint, and advancing a first threaded tap through the middle aspect of the facet joint, with the first threaded tap having a greater diameter than the first drill bit. In some embodiments, advancing the first threaded tap through the middle aspect of the facet joint may include advancing the first threaded tap into a posterior third of the disc space. In some embodiments, forming the access corridor also may include advancing a second threaded tap through the middle aspect of the facet joint, with the second threaded tap having a greater diameter than the first threaded tap, and advancing a second drill bit through the middle aspect of the facet joint, with the second drill bit having a greater diameter than the second threaded tap. In some embodiments, advancing the second threaded tap through the middle aspect of the facet joint may include advancing the second threaded tap into the posterior third of the disc space. In some embodiments, the one or more instruments may include one or more shavers, rongeurs, or curettes.

In some embodiments, the interbody device may be expandable from a compact configuration to an expanded configuration, and advancing the interbody device through the access corridor and into the disc space may include advancing the interbody device through the access corridor and into the disc space while the interbody device is in the compact configuration. In some embodiments, the method also may include expanding the interbody device from the compact configuration to the expanded configuration within the disc space. In some embodiments, the interbody device may have a first maximum transverse dimension when the interbody device is in the compact configuration and a second maximum transverse dimension when the interbody device is in the expanded configuration, and the access corridor may have a third maximum transverse dimension that is greater than the first maximum transverse dimension and less than the second maximum transverse dimension.

In some embodiments, the method also may include placing graft material within the disc space. In some embodiments, the method also may include placing graft material within the interbody device. In some embodiments, placing graft material within the interbody device may include placing graft material within the interbody device before advancing the interbody device through the access corridor and into the disc space. In some embodiments, the method also may include expanding the interbody device within the disc space, and placing graft material within the interbody device may include placing graft material within the interbody device after expanding the interbody device within the disc space. In some embodiments, the method also may include placing graft material within the access corridor. In some embodiments, placing graft material within the access corridor may include placing graft material between the interbody device and an entry point of the access corridor. In some embodiments, placing graft material within the access corridor may include placing graft material up to an entry point of the access corridor. In some embodiments, the method also may include expanding the interbody device within the disc space, and placing graft material within the access corridor may include placing graft material within the access corridor after expanding the interbody device within the disc space. In some embodiments, forming the access corridor may include forming the access corridor through the facet joint without exposing the exiting nerve root above the disc space. In some embodiments, forming the access corridor may include forming the access corridor through the facet joint without exposing the thecal sac.

These and other aspects and improvements of the present disclosure will become apparent to one of ordinary skill in the art upon review of the following detailed description when taken in conjunction with the several drawings and the appended claims.

DETAILED DESCRIPTION OF THE DISCLOSURE

Figure 1A:
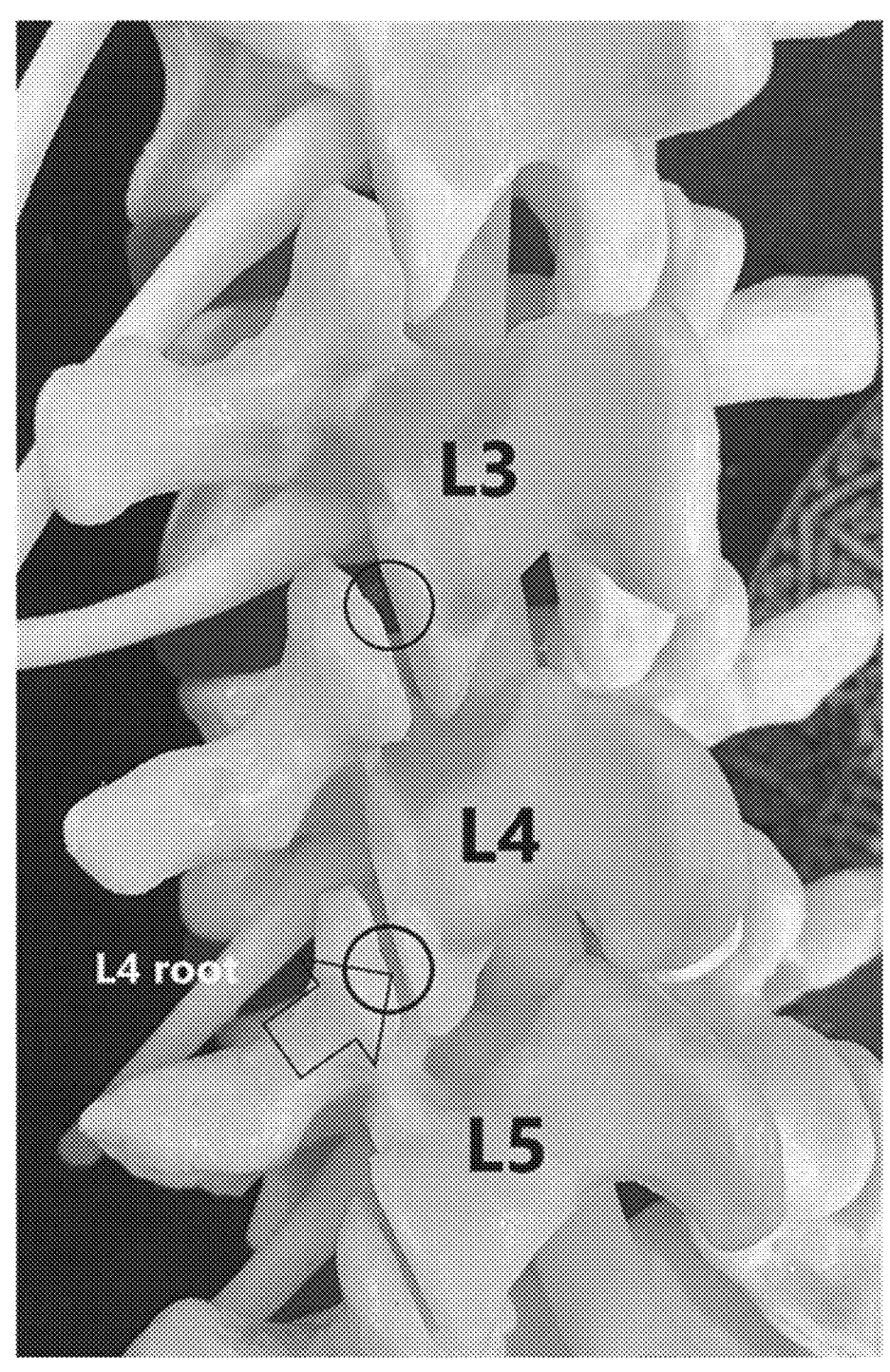
FIG. 1A illustrates a lumbar portion of a spine, showing facet joints of the spine.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

Overview

Figure 1B:
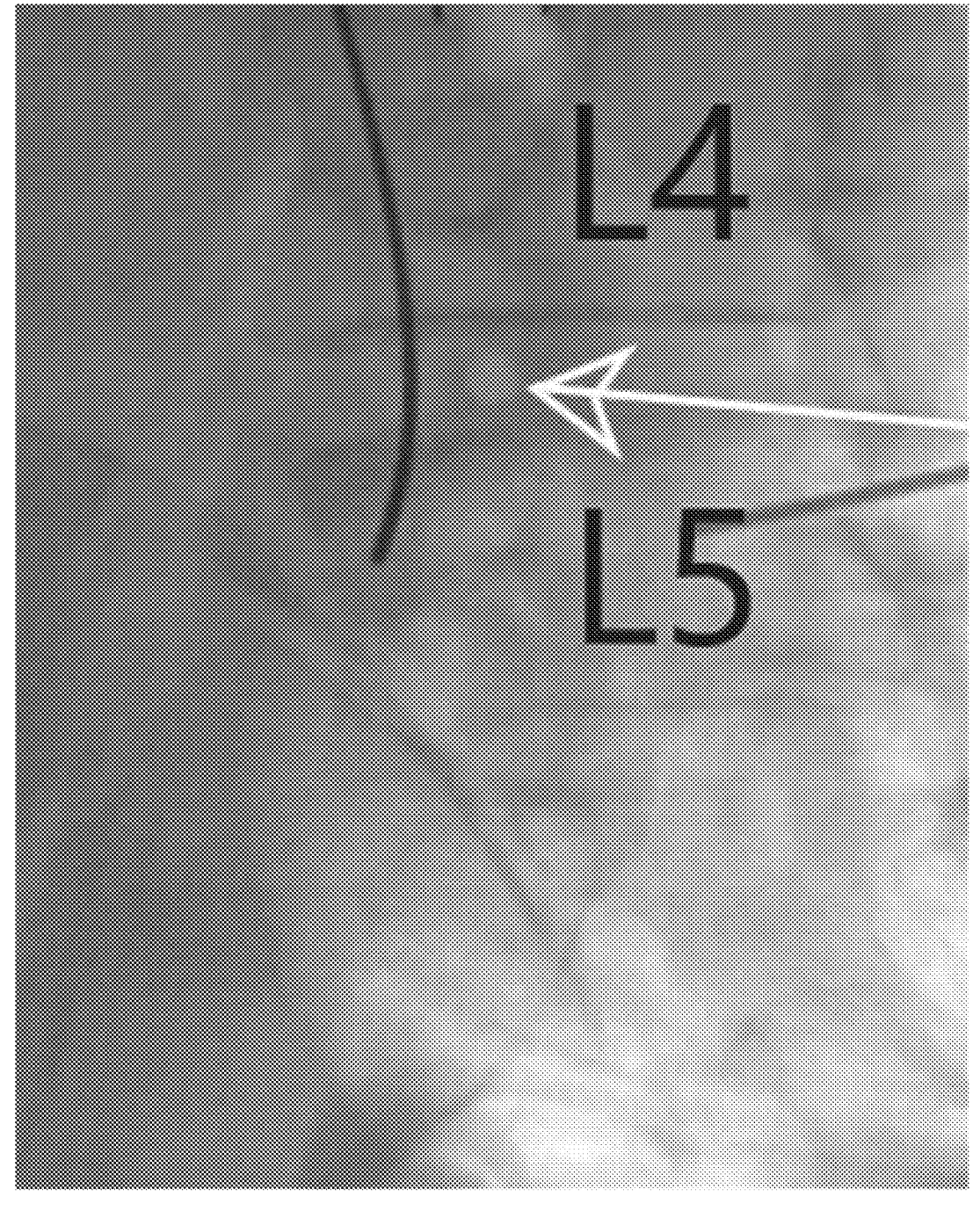
FIG. 1B is a radiographic image showing a facet joint of a spine.
Figure 2A:
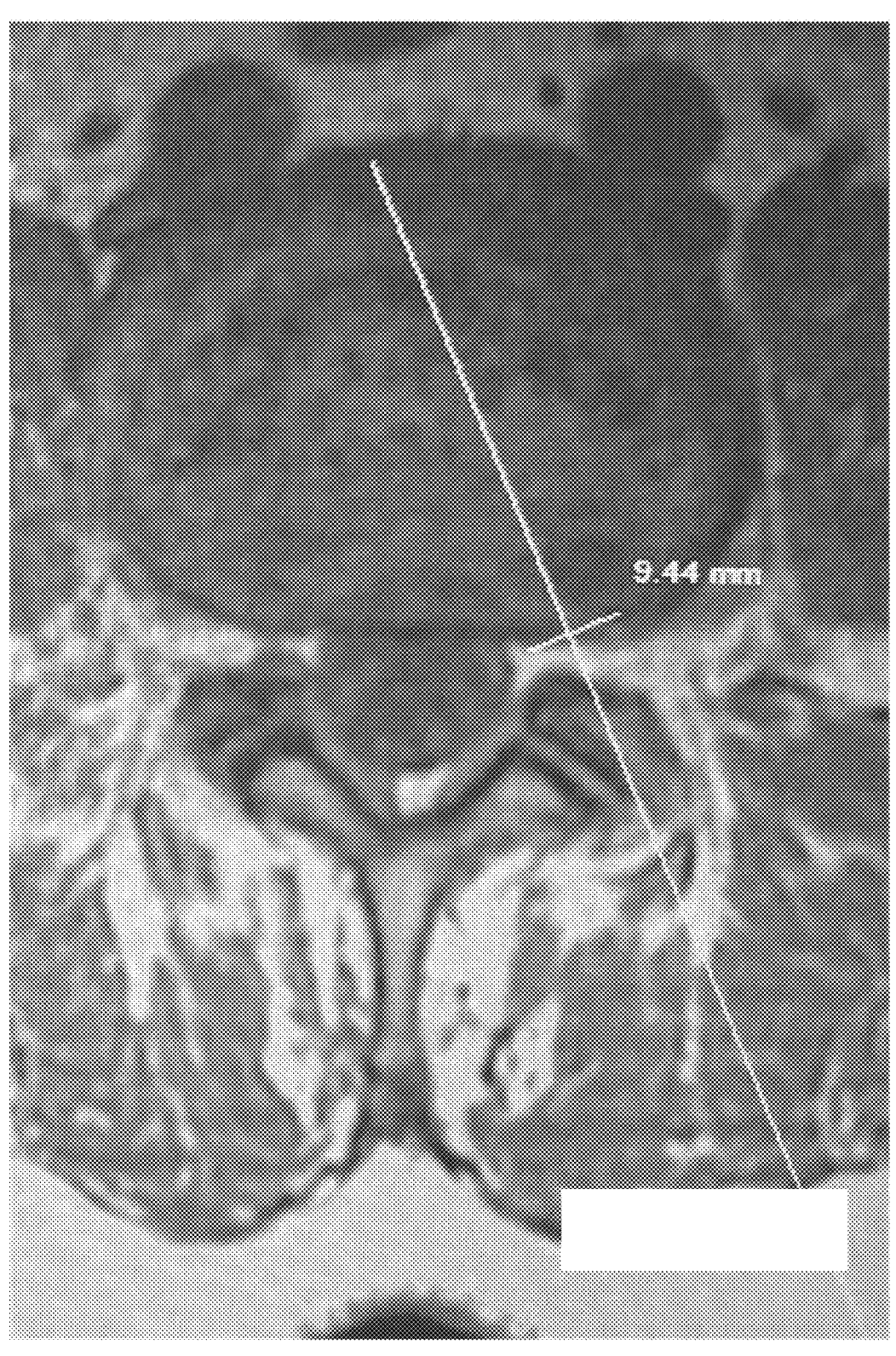
FIGS. 2A, 2B, 2C, and 2D illustrate trajectories for a trans-facet approach in accordance with embodiments of the disclosure.
Figure 2B:
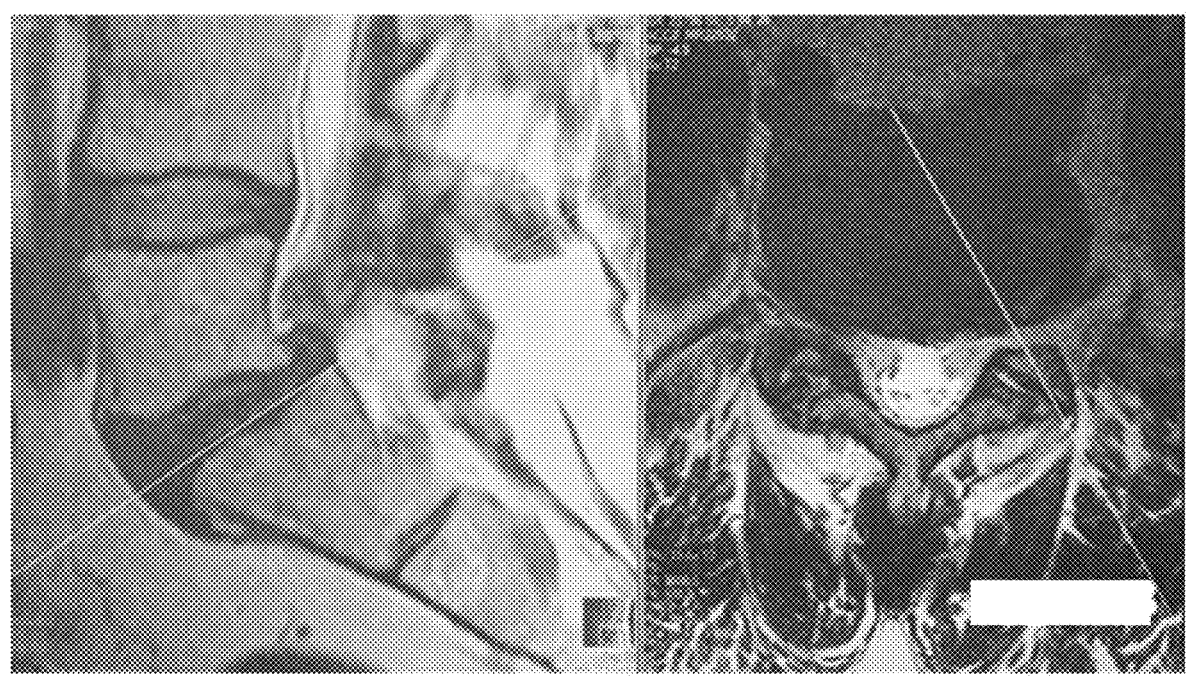
Figure 2C:
Figure 2D:

The present disclosure provides a novel approach and technique of minimally invasive robotic assisted trans-facet lumbar interbody fusion surgery, which also may be referred to as the "Z-LIF Operation," designating the access through the zygapophysial joints, or Z-joints (FIGS. 1A and 1B). As described herein, this operation employs the highest standards of minimally invasive surgery and combines it with the extreme accuracy and sophistication of a robotic system. In addition, this approach may utilize a navigation system in addition to verification of targets with live fluoroscopy. The approach may be confirmed with direct vision using intra-operative microscopy or endoscopy. Moreover, this approach may provide for the highest safety and protection for the neural elements. The sovereignty of exiting nerve roots and the thecal sac may not be compromised with this approach, as with the refinement of the technique, those nerve roots are not exposed. Not only is nerve root injury very unlikely, but also the risk of subsequent epidural scarring or arachnoiditis is very unlikely. The paraspinal muscles are very well respected with the utilization of very small minimal access tubes and microsurgical instruments. For most patients, the surgery may be performed as outpatient. Compared to existing approaches, the operative time may be reduced, and the risk of infection may be minimal to nonexistent. Unlike PLIF and TLIF procedures, the nerve roots are not exposed. Unlike ALIF, DLIF, and XLIF procedures, peritoneal structures and the lumbosacral plexus are not involved. In summary, the only soft tissue structures encountered are skin, subcutaneous tissue, paraspinal muscles, and disc elements. This approach provides for an excellent potential for the development of an elaborate highly intelligent autonomous robotic system.

Still other benefits and advantages of the trans-facet lumbar interbody fusion approach provided herein provided herein over existing approaches will be appreciated by those of ordinary skill in the art from the following description and the appended drawings.

Example Surgical Technique

Patient selection is certainly key to the success of any surgical procedure. The present technique has been employed on patients with severe intractable discogenic lower back pain with degenerative disc disease as well as grade 1 spondylolisthesis, both congenital and degenerative. This technique is suitable for the disc spaces of L3-4, L4-5, and L5-S1. This technique generally may not be recommended for the L1-2 or L2-3 levels. The present technique also may be suitable for patients needing fusion who also have mild or moderate spinal stenosis, with or without claudication pain. In those patients, indirect decompression occurs with restoration of disc height with concomitant widening of the foramina of the nerve roots. The present technique also may be suitable in the presence of severe spinal stenosis, where in addition to the indirect decompression mentioned above, this approach allows for decompression of the spinal canal. This is brought about by microsurgical drilling of the medial wall of the facet joint, with or without excision of the adjacent ligamentum flavum and decompression of the distally exiting nerve root (which may be referred to as "Z-LIF plus"). Most of these patients may undergo lumbosacral MRIs or post myelogram CT scans prior to the decisions to proceed with surgery. A few days prior to surgery, a lumbosacral CT scan with a navigation protocol may be performed with the patient in the prone position.

Figure 3:
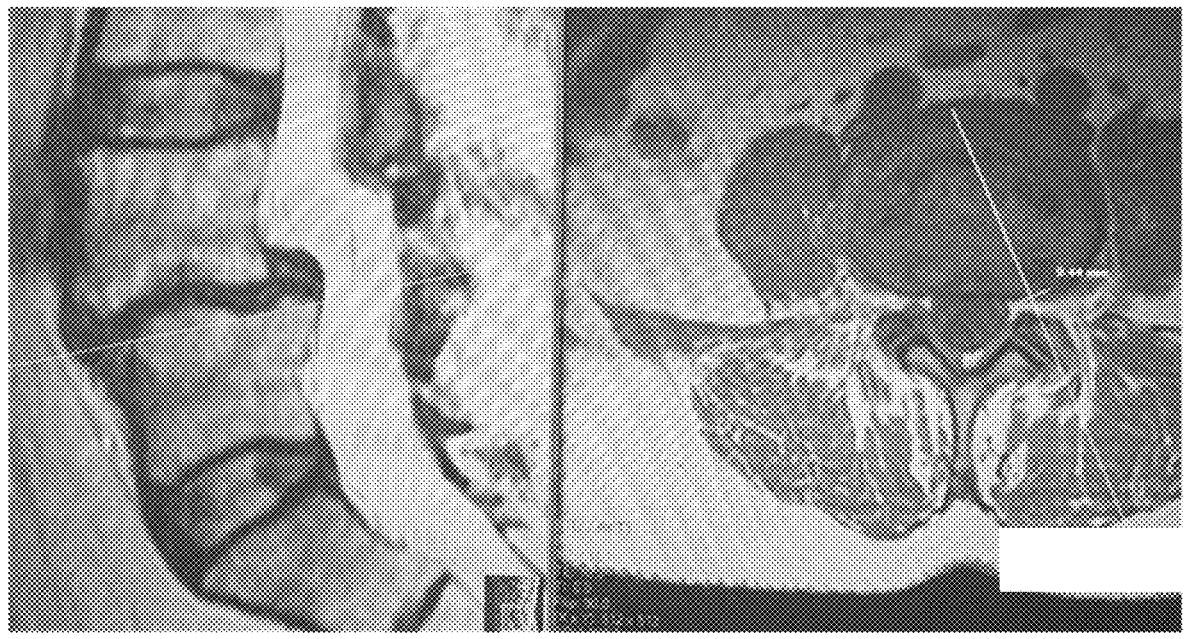
FIG. 3 illustrates an adjusted trajectory for a trans-facet approach in accordance with embodiments of the disclosure.

Various robotic systems may be used for the present technique. For example, the Mazor Robotic System has been used successfully for the approach. Other robotic systems are available and may be considered. Surgical planning may be performed using the Mazor planning software to which the preoperative lumbar CT scan performed in the prone position is uploaded. Along with planning for the trans-facet approach into the disc space, the surgeon also may plan for placement of the pedicle screw wires. The trajectory of the approach into the facet joint area generally may depend on the axial and sagittal CT scan cuts after correlating them with the T1 and T2 MRI images or post myelogram axial CT images. It may be advantageous to identify the lateral edge of the thecal sac within the spinal canal as well as to determine the exact location of the exiting nerve root above the disc space. The trajectory then may be outlined on the axial cut passing through the entry point on the middle portion of the facet joint midway between the inferior articular facet of the vertebra above and the superior articular facet of the vertebra below. The trajectory also may be made to pass towards the target, which may be located 0 to 8 millimeters across the midline area at the anterior aspect of the disc space (FIGS. 2A-D). The trajectory then may be adjusted to pass parallel to the inferior aspect of the disc space immediately above the superior endplate of the vertebra below (FIG. 3). This may keep the trajectory as far as possible from the exiting nerve root superiorly, which may be especially important in a case of grade 1 spondylolisthesis in which the exiting nerve root is closer to the disc space than in a case without spondylolisthesis.

Figure 4A:
FIG. 4A illustrates placement of a Schanz pin in accordance with embodiments of the disclosure.
Figure 4B:
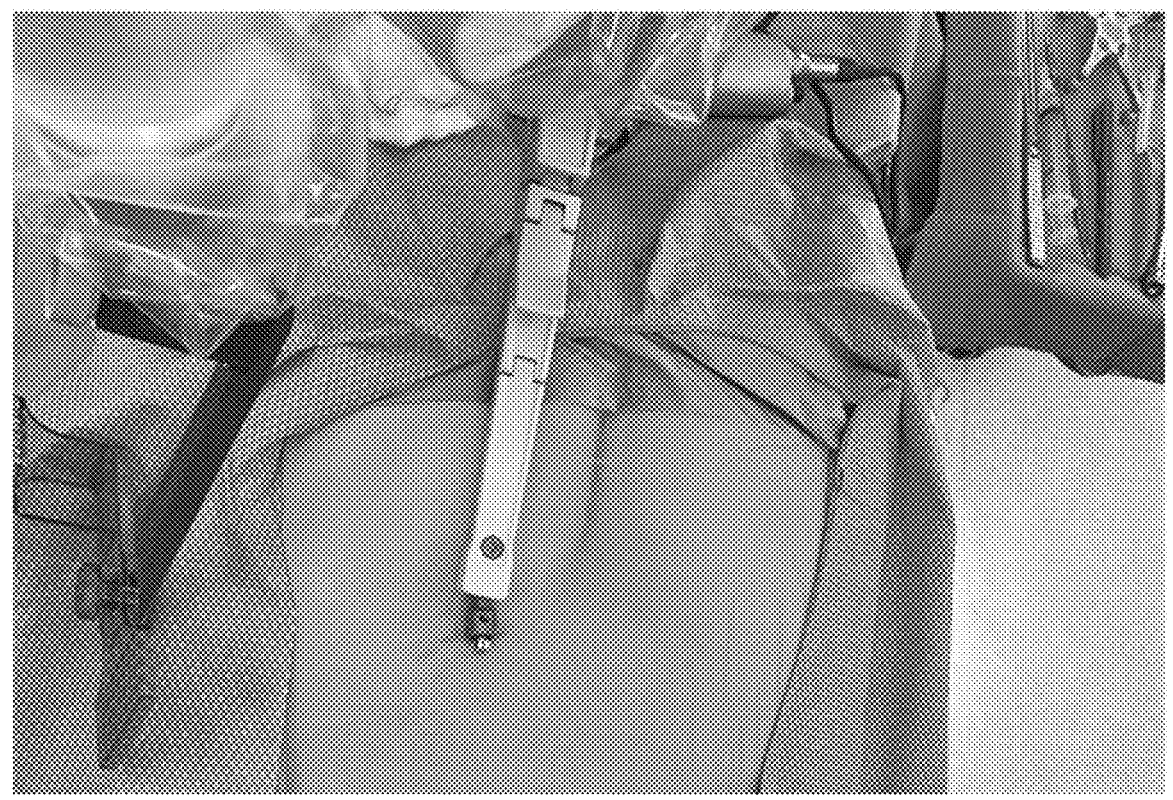
FIG. 4B illustrates attachment of a robotic arm to the Schanz pin.
Figure 5A:
FIGS. 5A and 5B illustrate fluoroscopic images being obtained in accordance with embodiments of the disclosure.
Figure 5B:
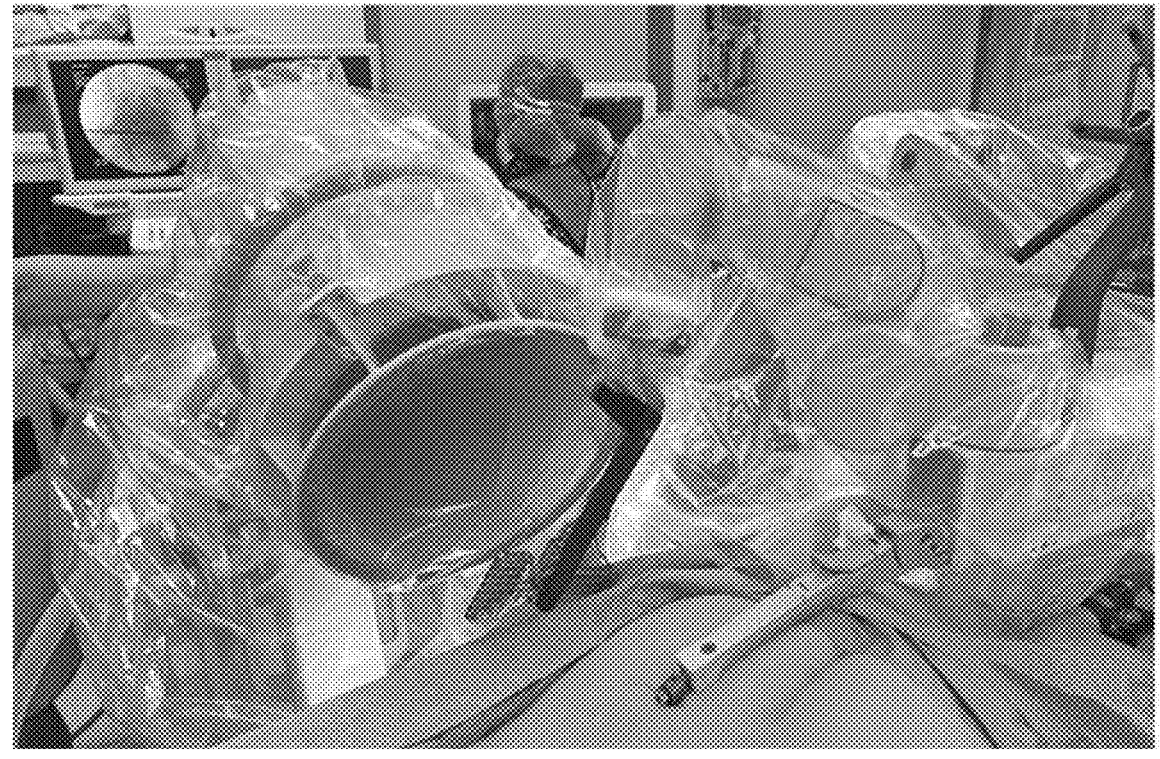
Figure 6A:
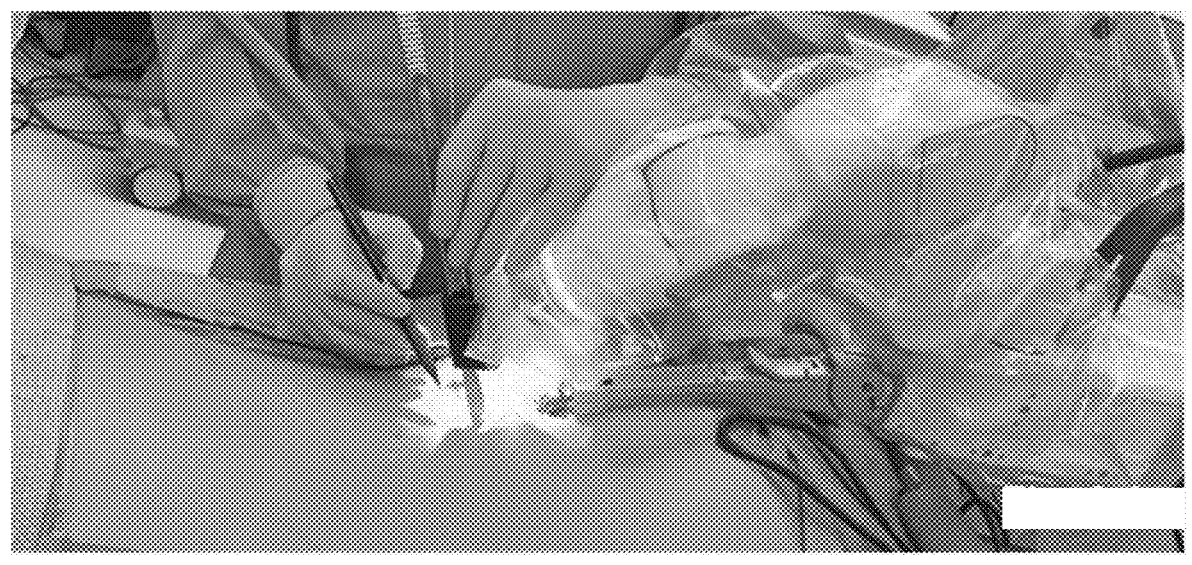
FIG. 6A illustrates marking of a skin incision site in accordance with embodiments of the disclosure.
Figure 6B:
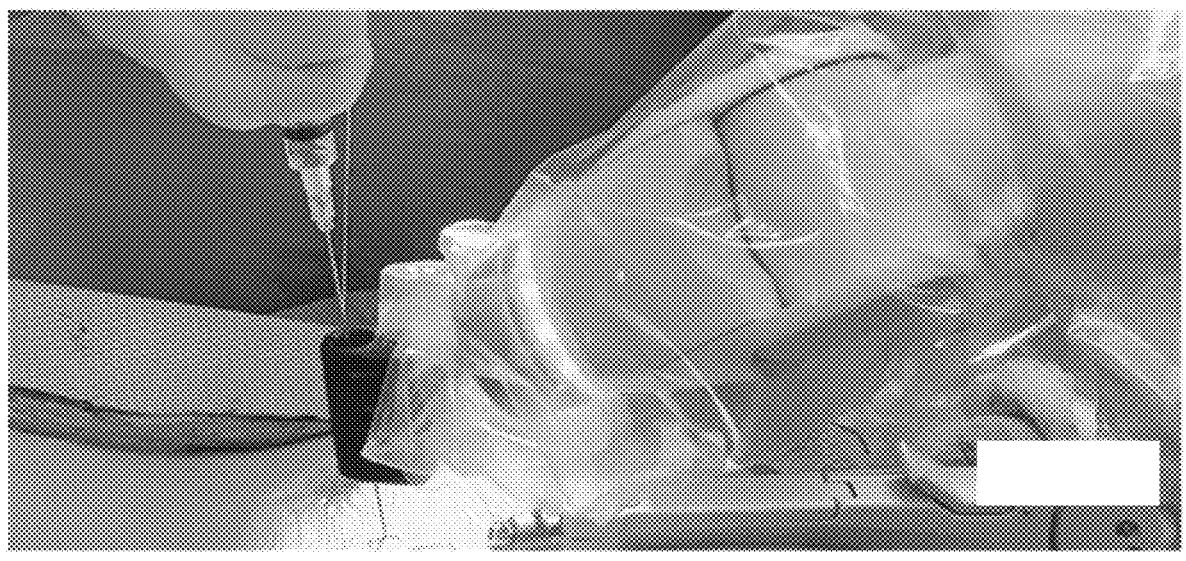
FIGS. 6B, 6C, and 6D illustrate introduction of a local anesthetic in accordance with embodiments of the disclosure.
Figure 6C:
Figure 6D:
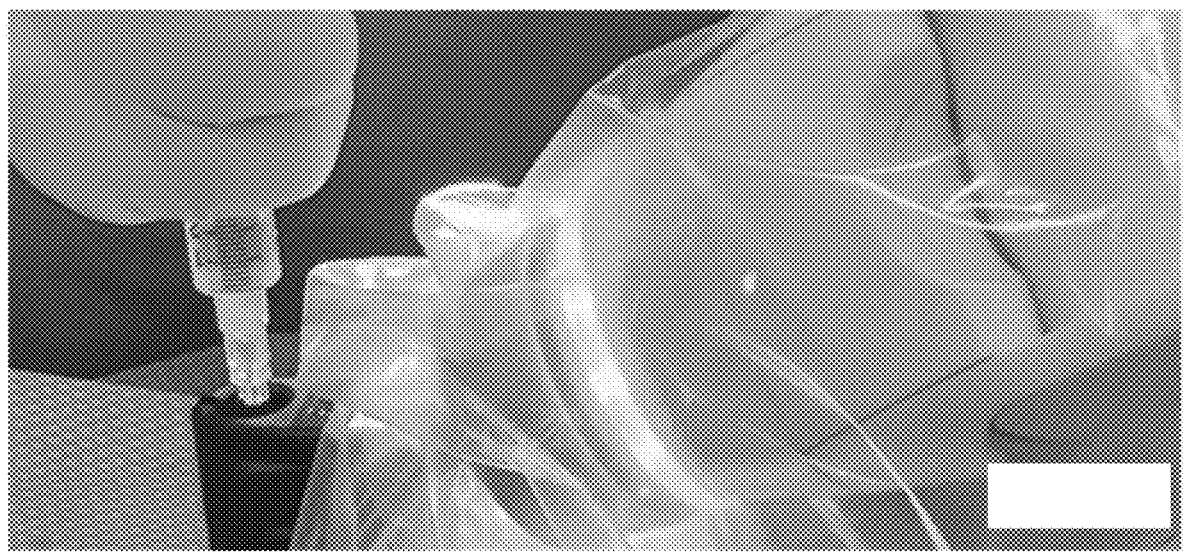
Figure 7:
FIG. 7 illustrates a skin incision being made in accordance with embodiments of the disclosure.
Figure 8A:
FIGS. 8A and 8B illustrate placement of a one-step navigated dissector-dilator in accordance with embodiments of the disclosure.
Figure 8B:
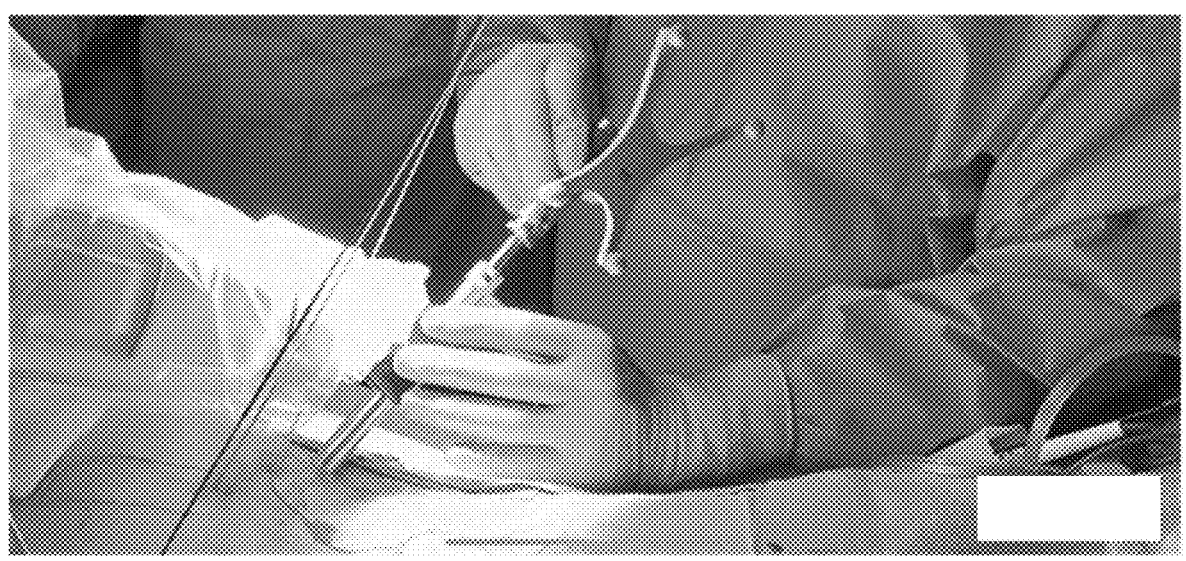

The patient then may undergo general anesthesia and be placed in the prone position well-padded on a Jackson table. The Mazor Robotic System or other robotic system then may be fixed to the table on the right side of the patient on the right side of the hip region. The skin overlying the whole of the lumbosacral region may be prepped adequately. A Schanz pin may be placed into the right posterior superior iliac spine (FIG. 4A). The robotic arm then may be attached to the pin (FIG. 4B) and scan the operative field. Fluoroscopic images may be obtained in the AP, lateral, and oblique trajectories (FIGS. 5A and 5B) and blended with the preoperative CT scan images to adjust for any minimal changes brought about by positioning of the patient as well as adjusting for any changes in the degree of lordosis. The robotic arm then may be moved to execute the plan. The surgeon first may place pedicle screw wires before proceeding with the trans-facet access into the disc space. Through the robotic arm guide, the site of the skin incision may be marked (FIG. 6A). The surgeon may introduce a local anesthetic to infiltrate the whole track from skin to target using an 18 Gauge spinal needle (FIGS. 6B-D). A skin incision then may be made (FIG. 7), followed by placement of a one-step navigated dissector-dilator to the target (FIGS. 8A and 8B).

Figure 9:
FIG. 9 illustrates placement of a navigated drill into a pedicle in accordance with embodiments of the disclosure.
Figure 10:
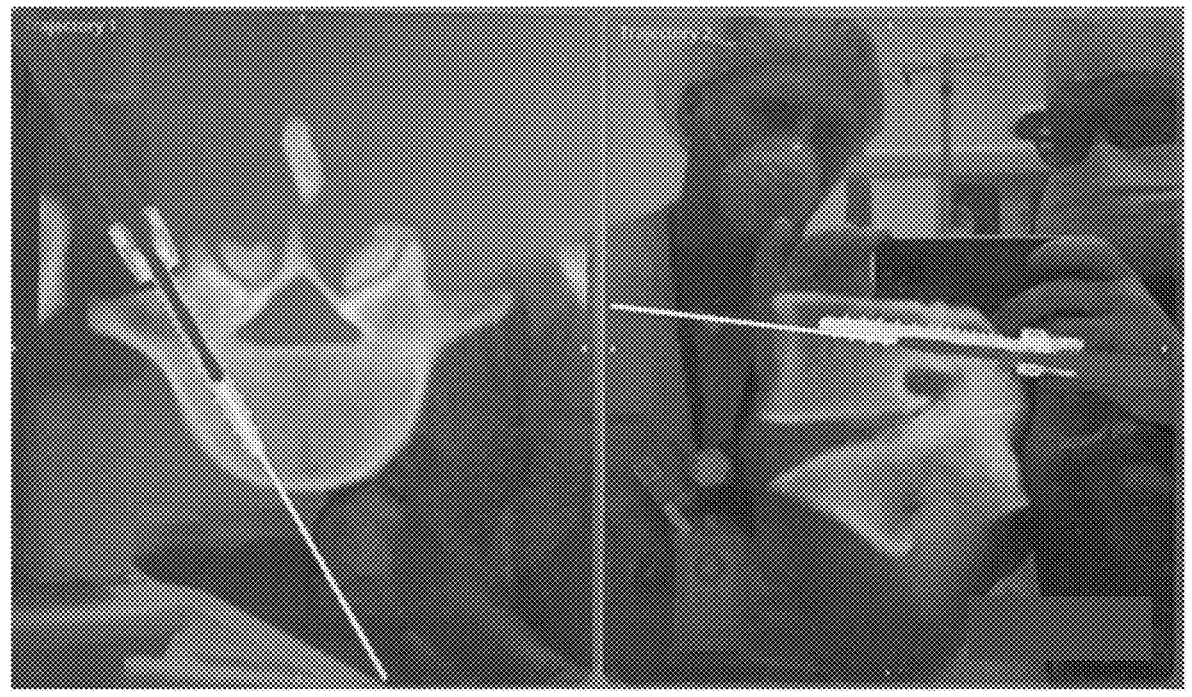
FIG. 10 illustrates placement of a navigated tap into the pedicle in accordance with embodiments of the disclosure.
Figure 11:
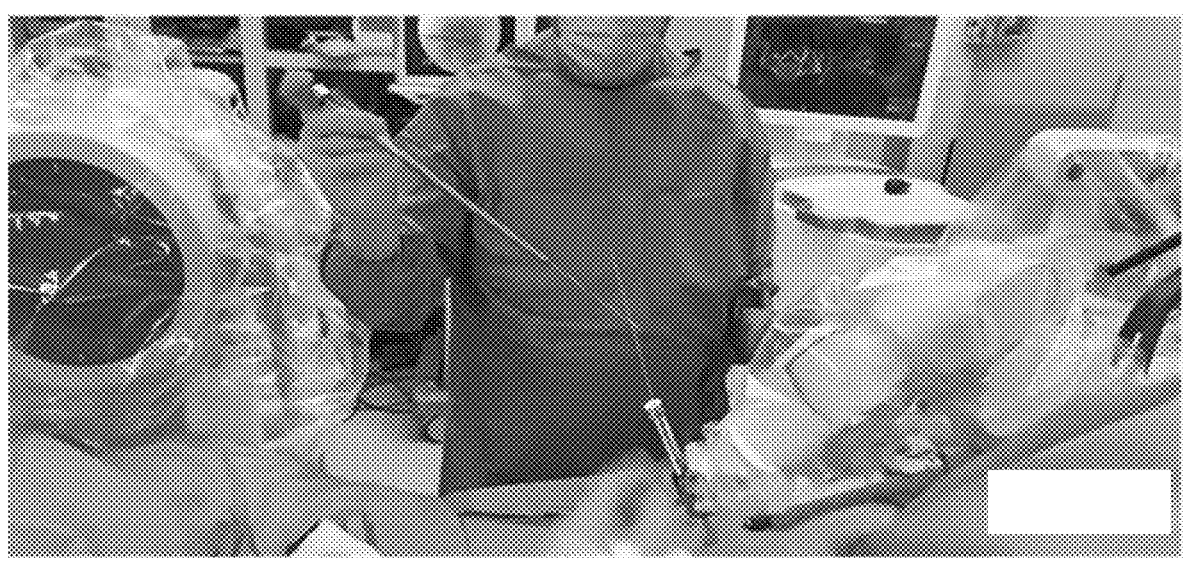
FIG. 11 illustrates placement of a K-wire into the pedicle in accordance with embodiments of the disclosure.
Figure 12:
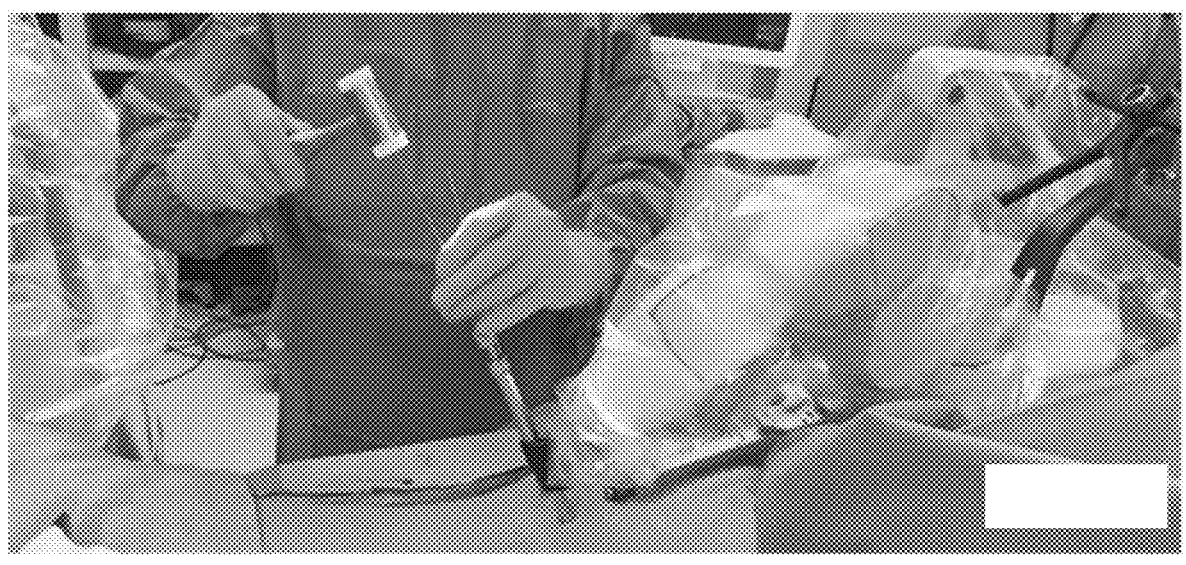
FIG. 12 illustrates the K-wire being tapped into position in the pedicle in accordance with embodiments of the disclosure.
Figure 13A:
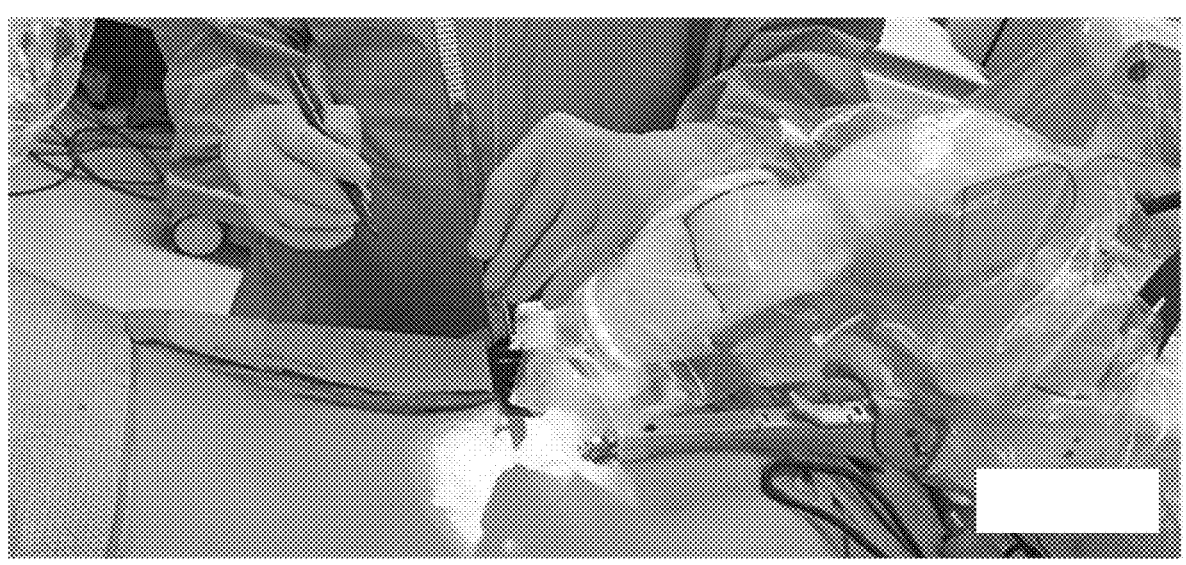
FIGS. 13A, 13B, 13C, 13D, 13E, and 13F illustrate placement of additional K-wires into additional pedicles in accordance with embodiments of the disclosure.
Figure 13B:
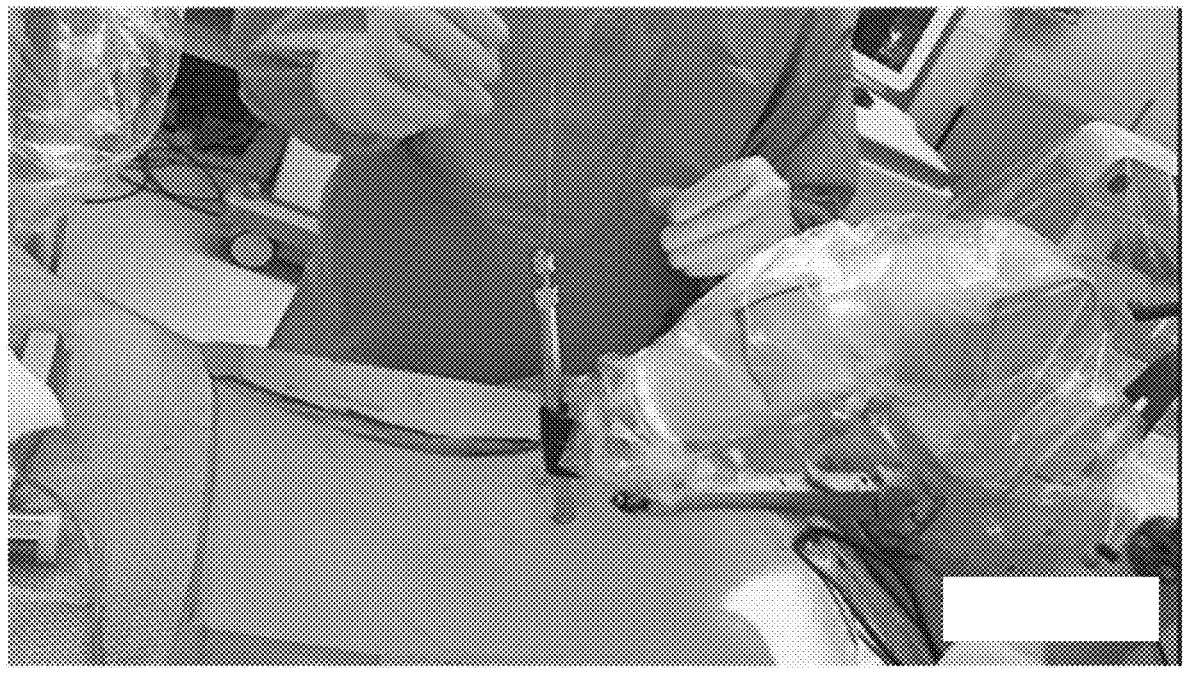
Figure 13C:
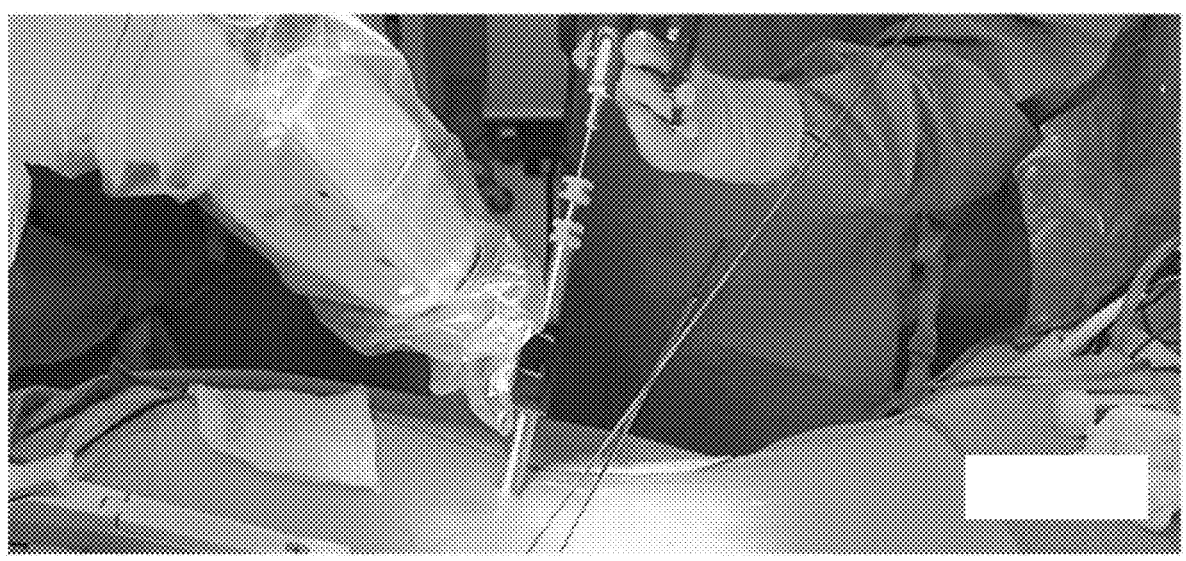
Figure 13D:
Figure 13E:
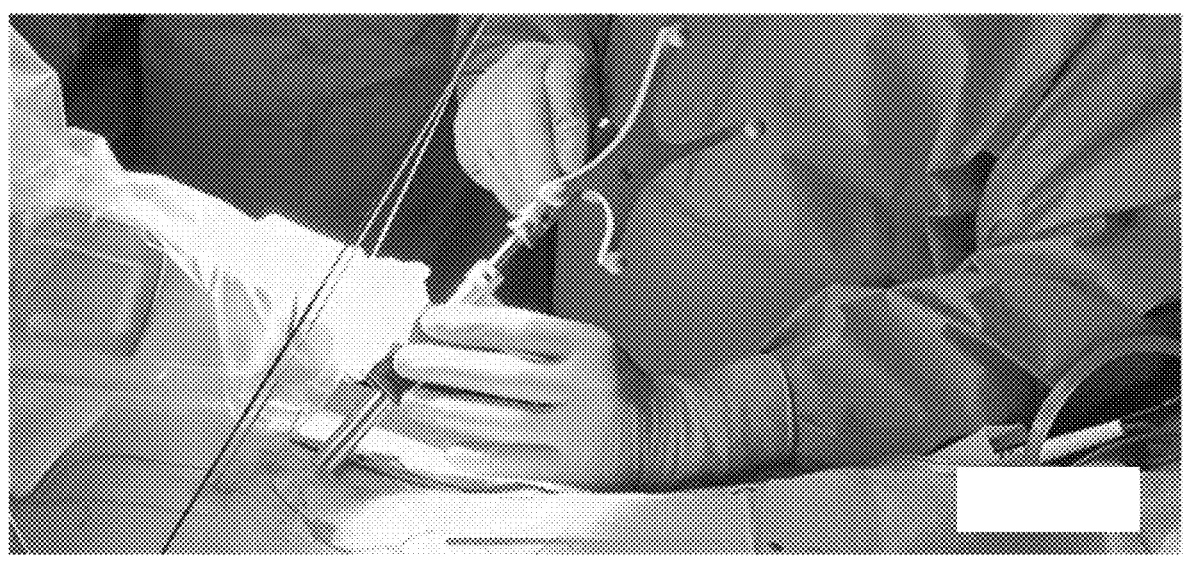
Figure 13F:
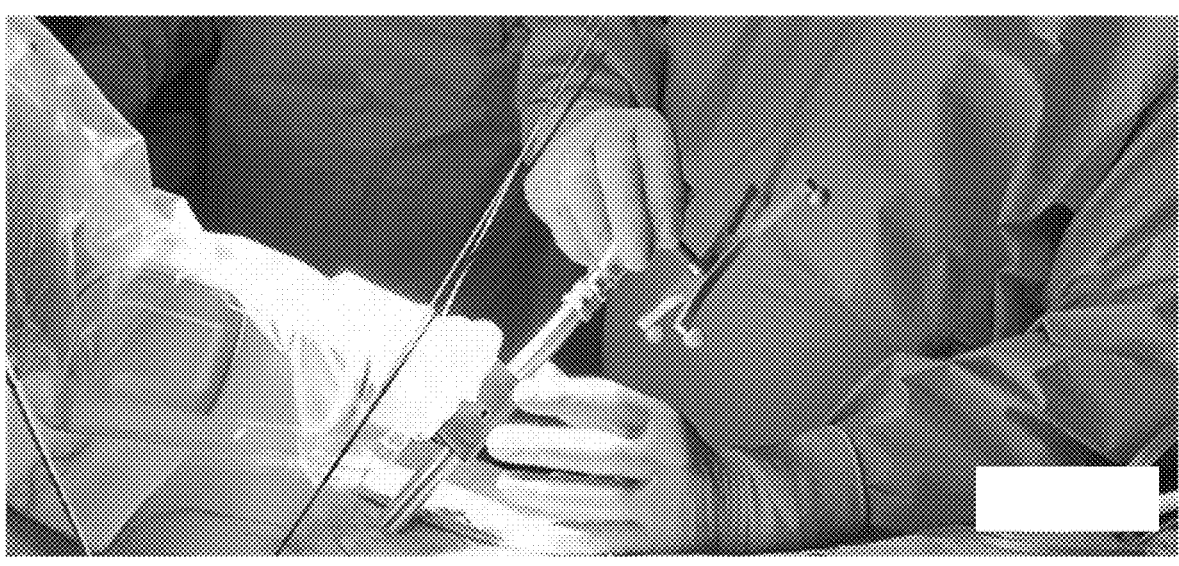
Figure 14A:
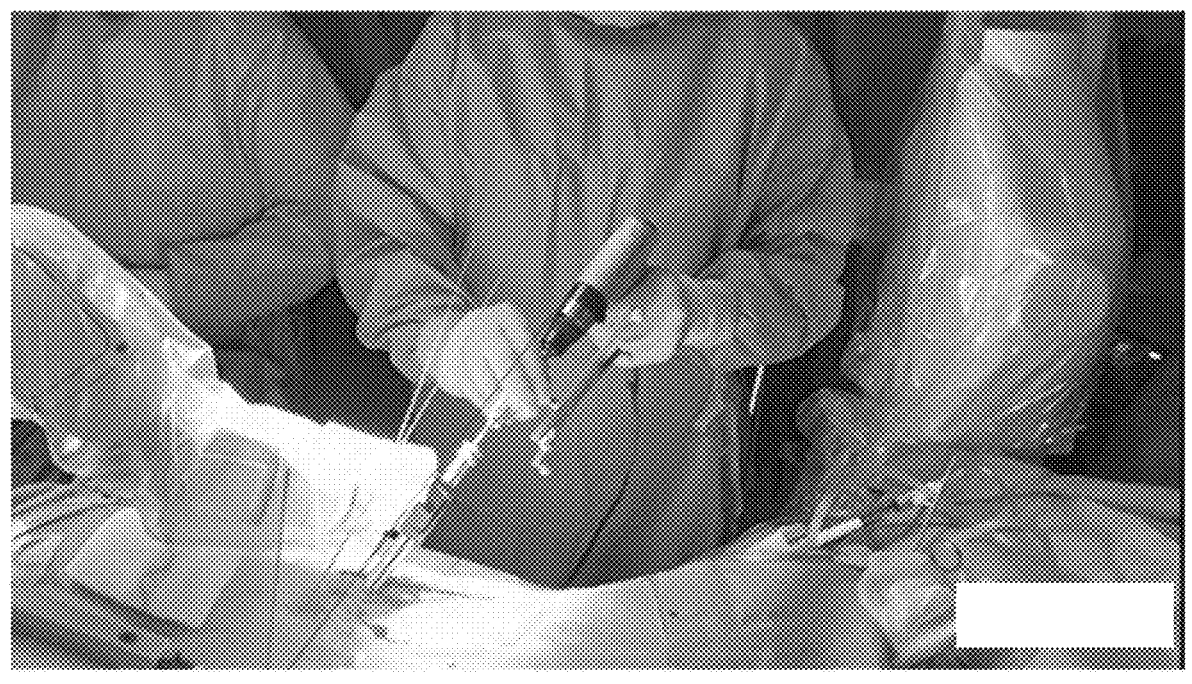
FIGS. 14A, 14B, 14C, 14D, and 14E illustrate introduction of a navigated drill into one of the pedicles in accordance with embodiments of the disclosure.
Figure 14B:
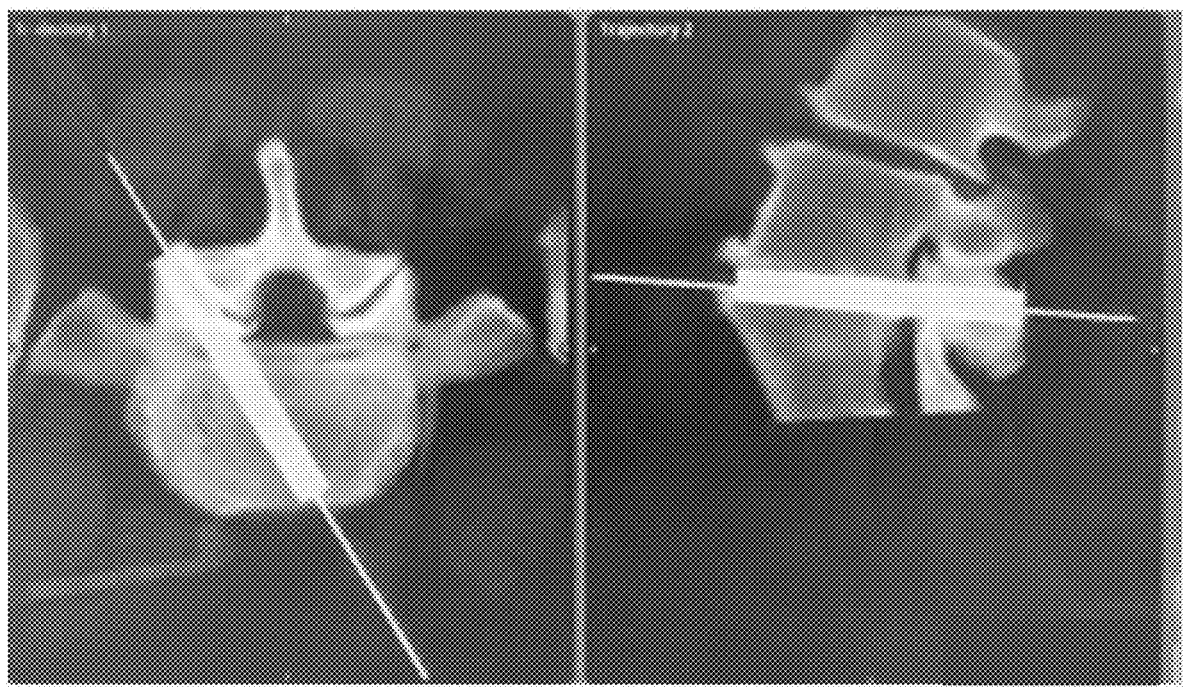
Figure 14C:
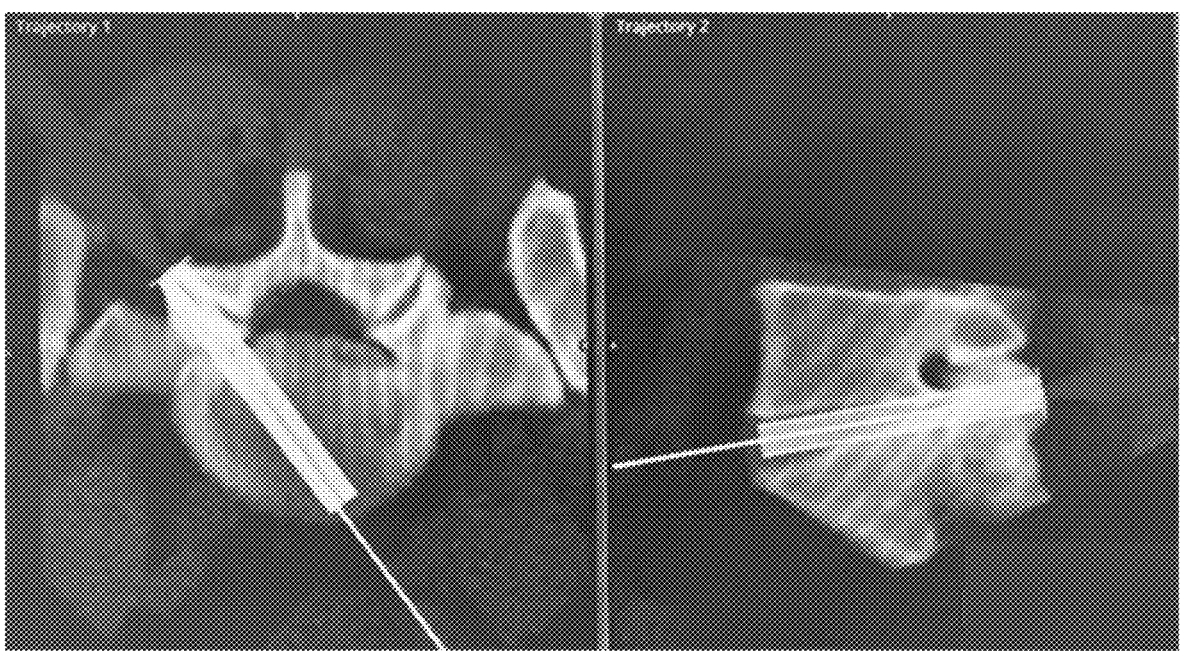
Figure 14D:
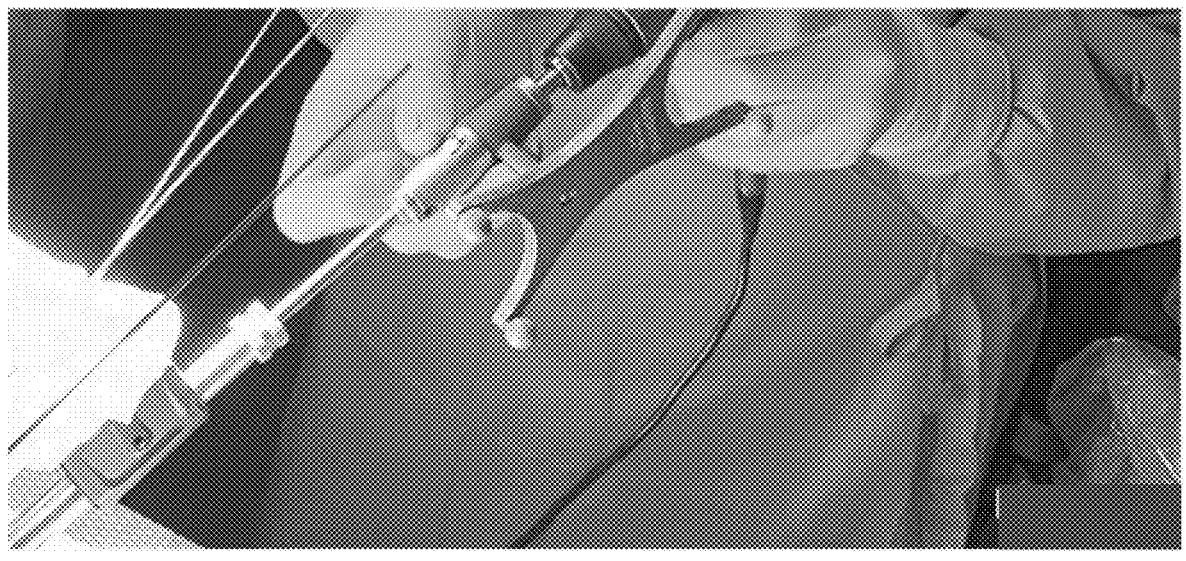
Figure 14E:
Figure 15A:
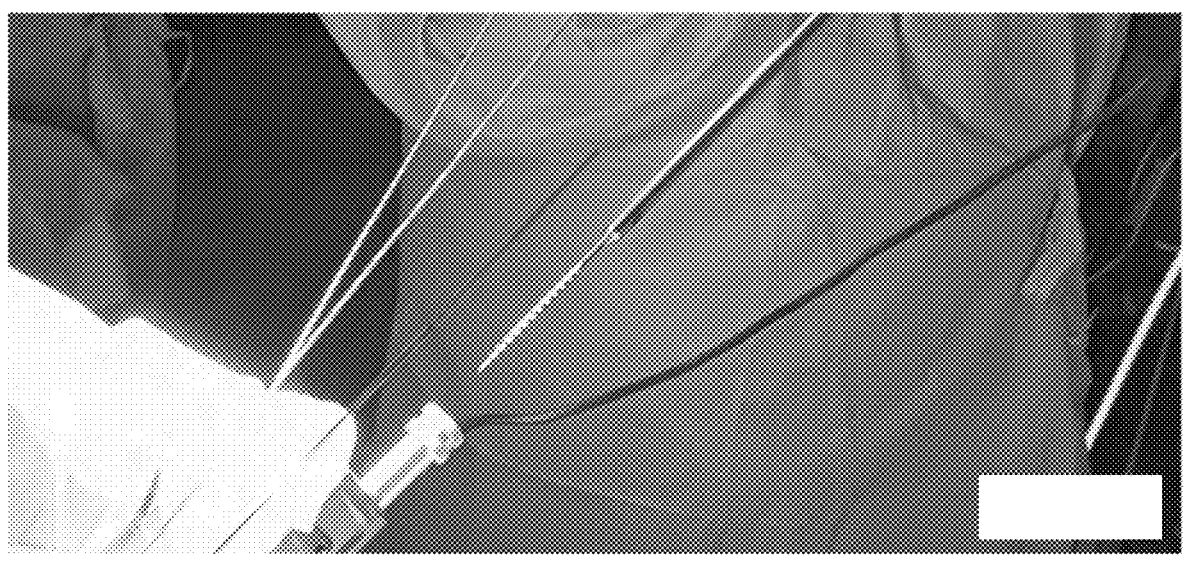
FIGS. 15A and 15B illustrate introduction of a navigated tap into one of the pedicles in accordance with embodiments of the disclosure.
Figure 15B:
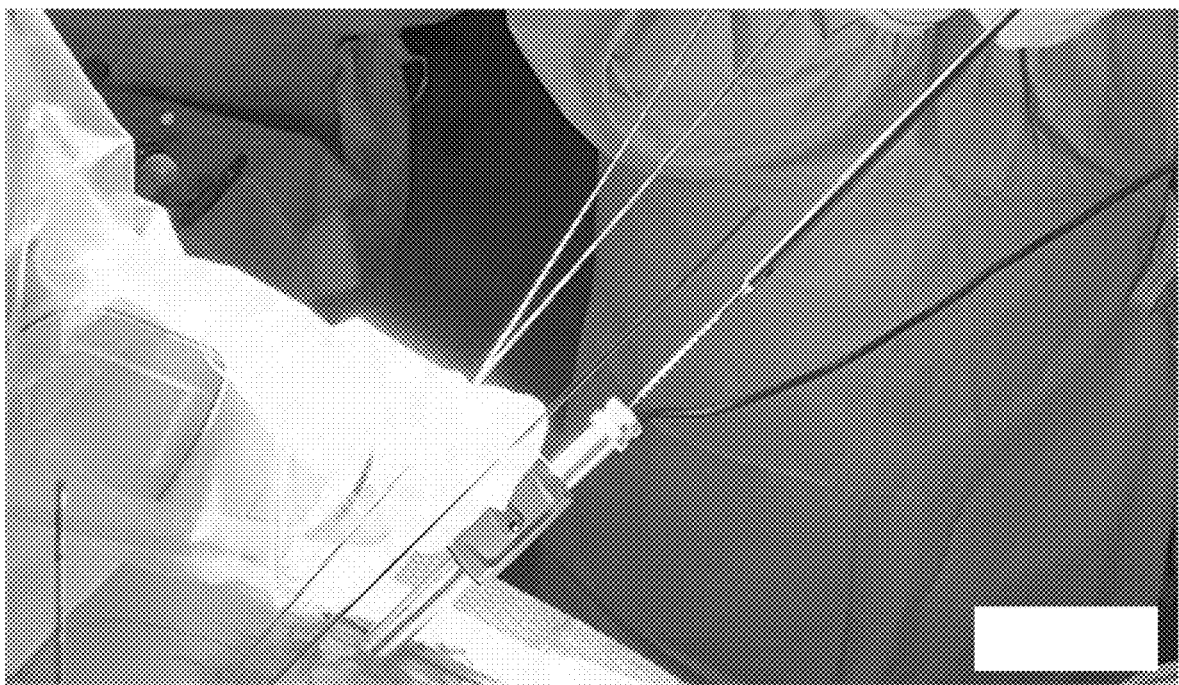
Figure 16A:
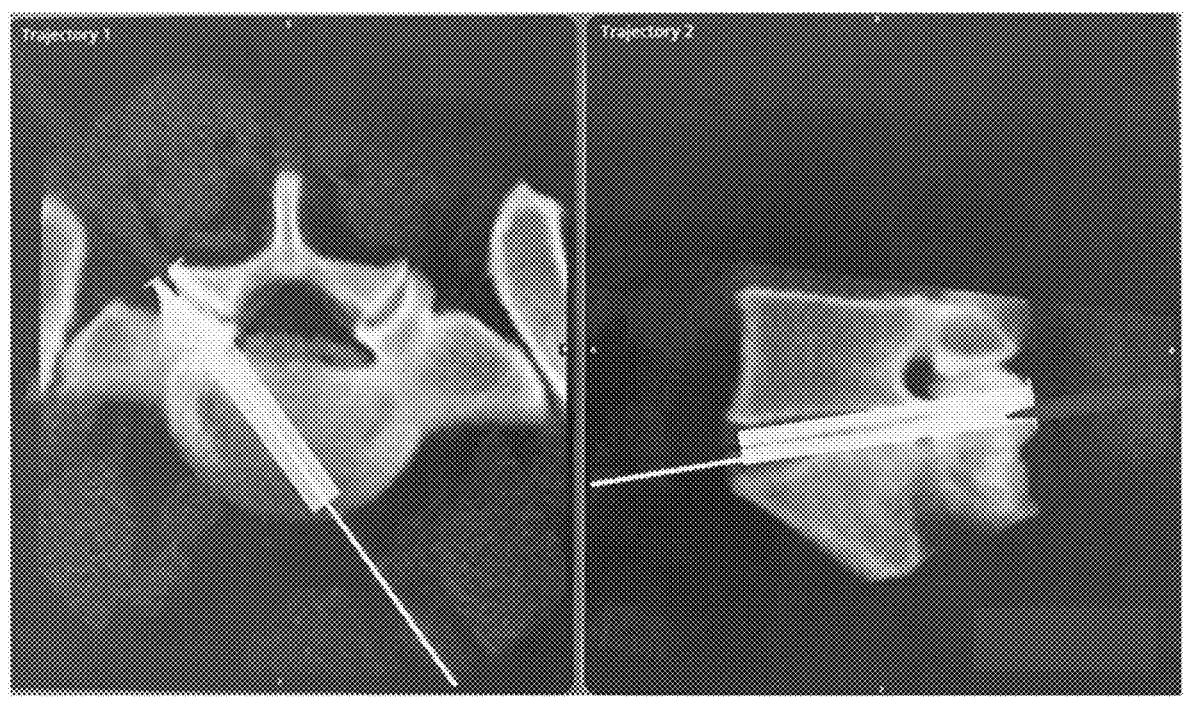
FIGS. 16A, 16B, 16C, and 16D illustrate the navigated tap being advanced through the middle aspect of the fact joint and into the posterior third of the disc space in accordance with embodiments of the disclosure.
Figure 16B:
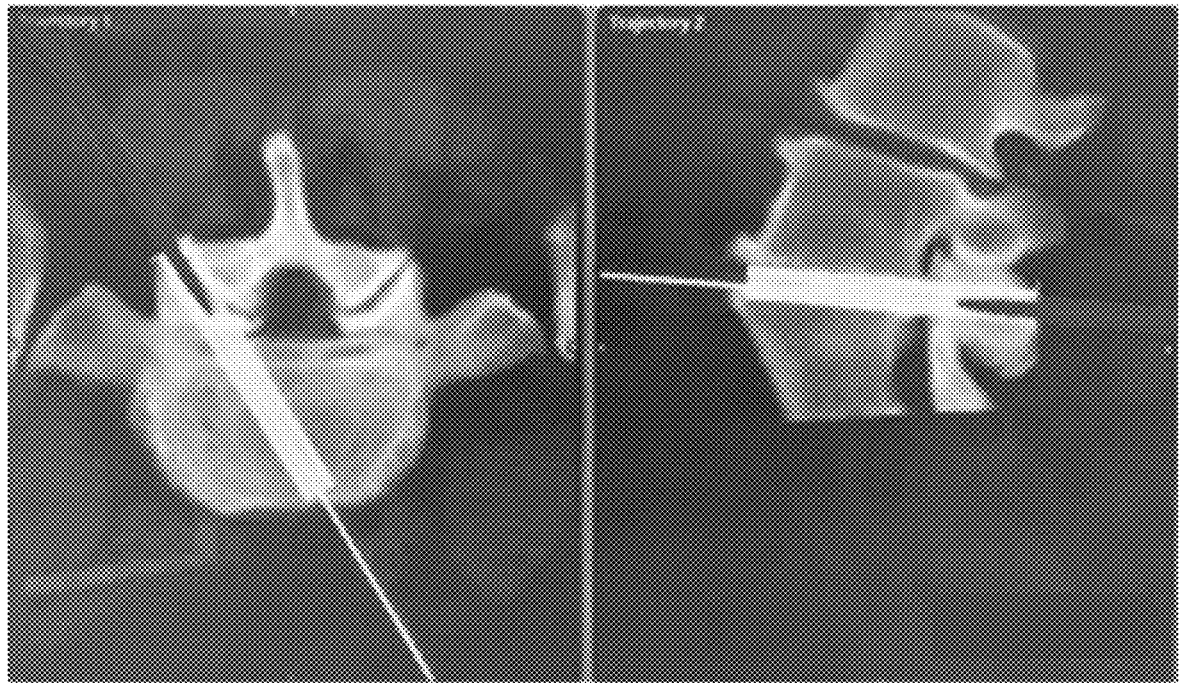
Figure 16C:
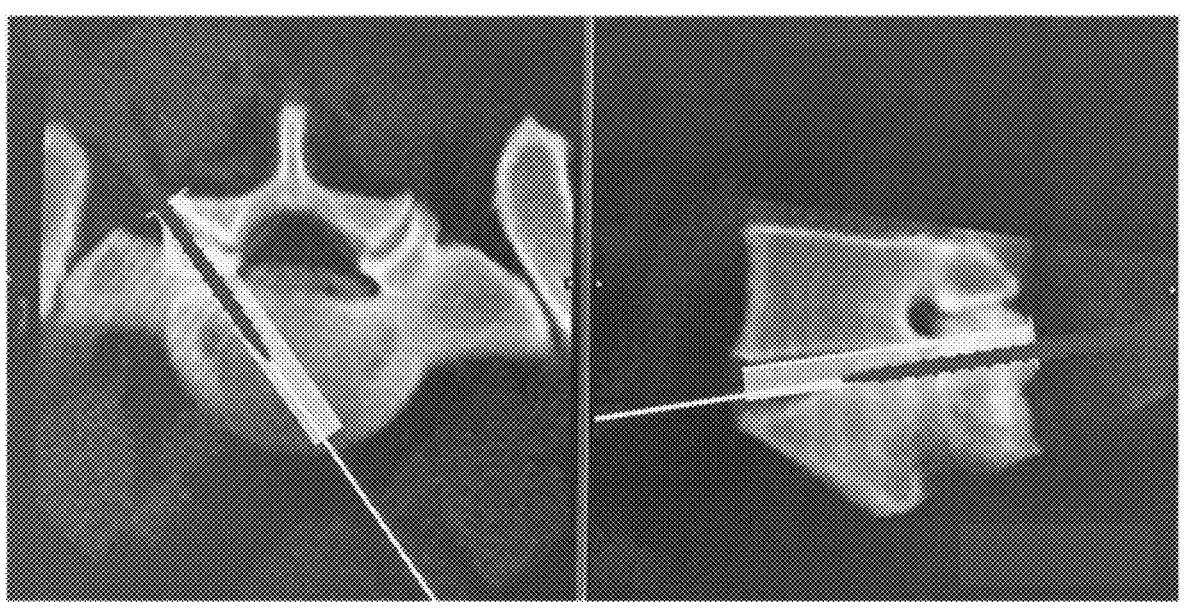
Figure 16D:
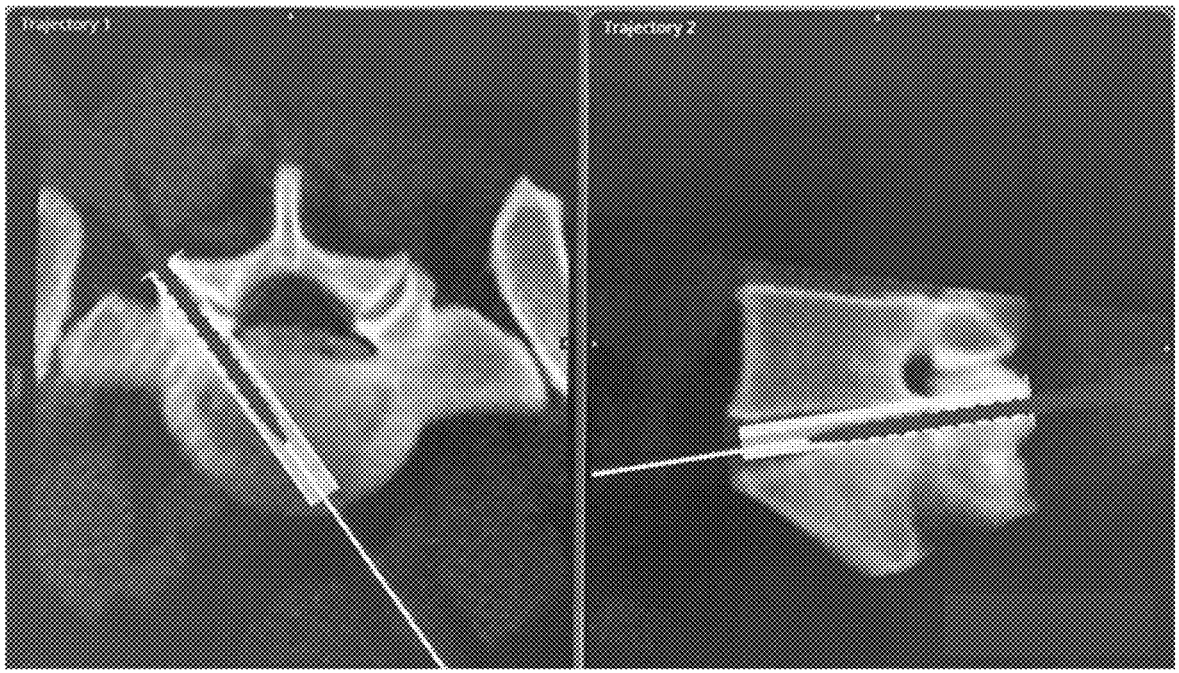
Figure 17A:
FIGS. 17A, 17B, and 17C illustrate placement of a K-wire and a first navigated dilator of a minimal access tube system in accordance with embodiments of the disclosure.
Figure 17B:
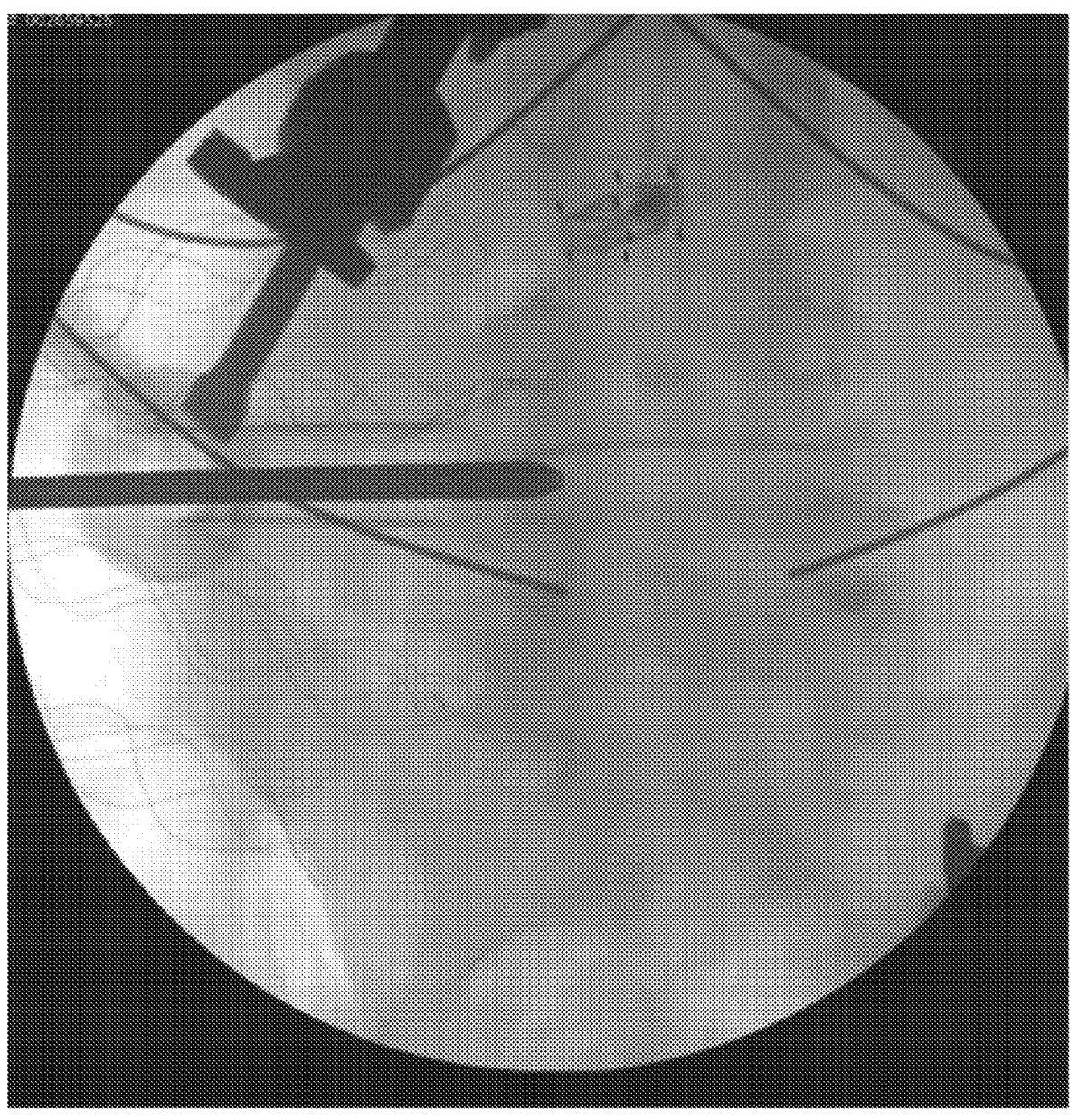
Figure 17C:
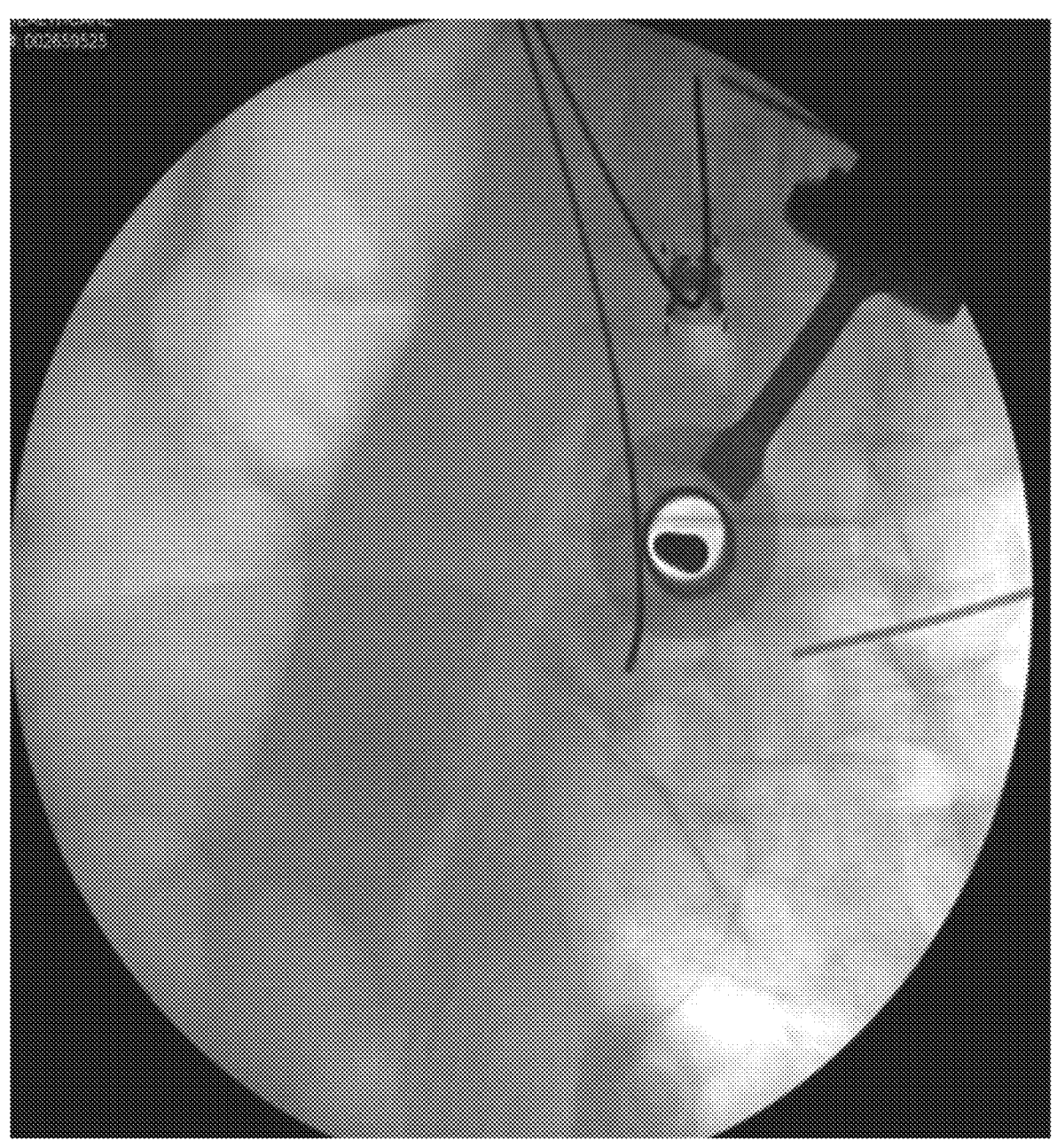
Figure 18A:
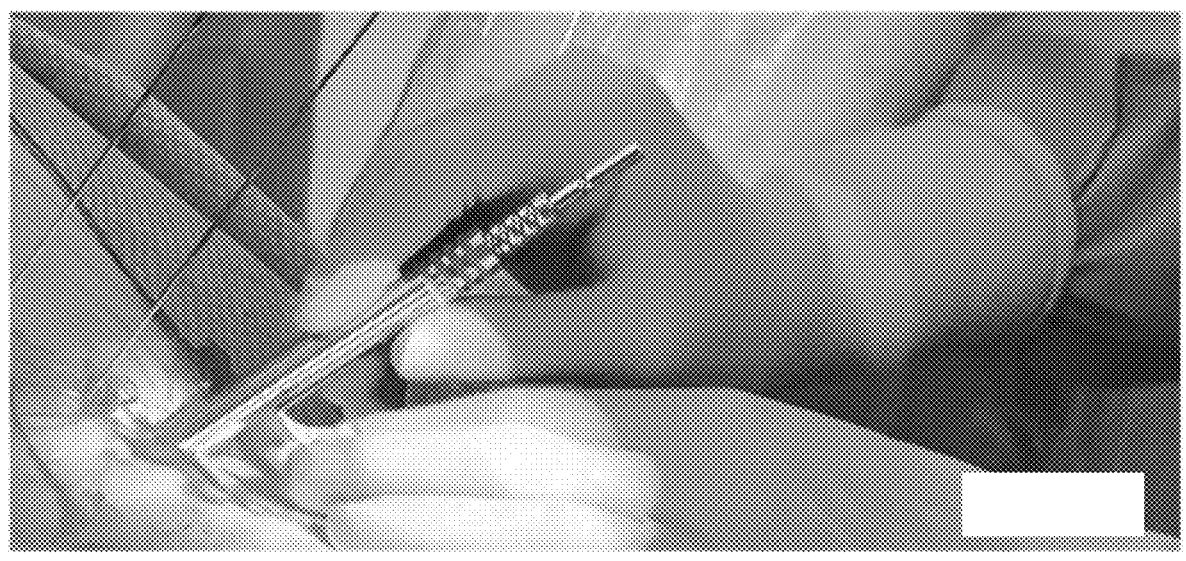
FIGS. 18A and 18B illustrate placement of larger dilators of the minimal access tube system in accordance with embodiments of the disclosure.
Figure 18B:
Figure 19A:
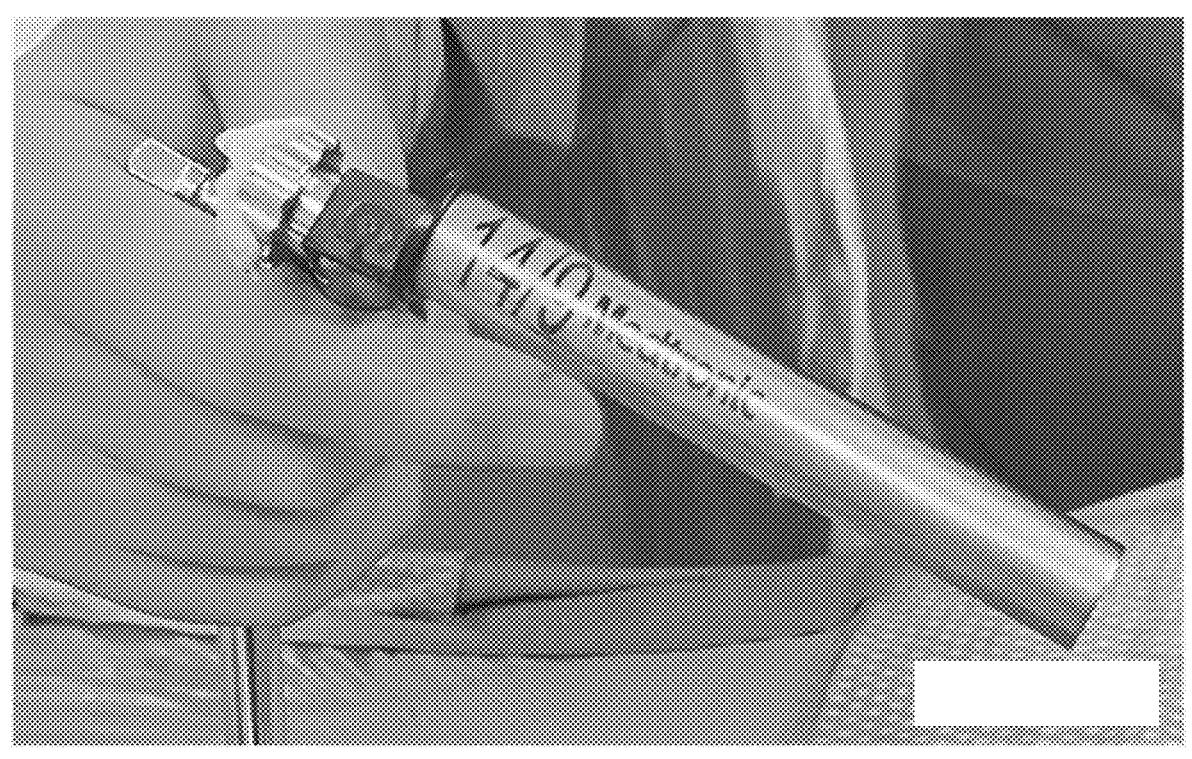
FIGS. 19A and 19B illustrate placement of a minimal access tube of the minimal access tube system in accordance with embodiments of the disclosure.
Figure 19B:
Figure 19C:
FIGS. 19C and 19D illustrate the minimal access tube being fixed in position to a Jackson table via a FlexArm in accordance with embodiments of the disclosure.
Figure 19D:
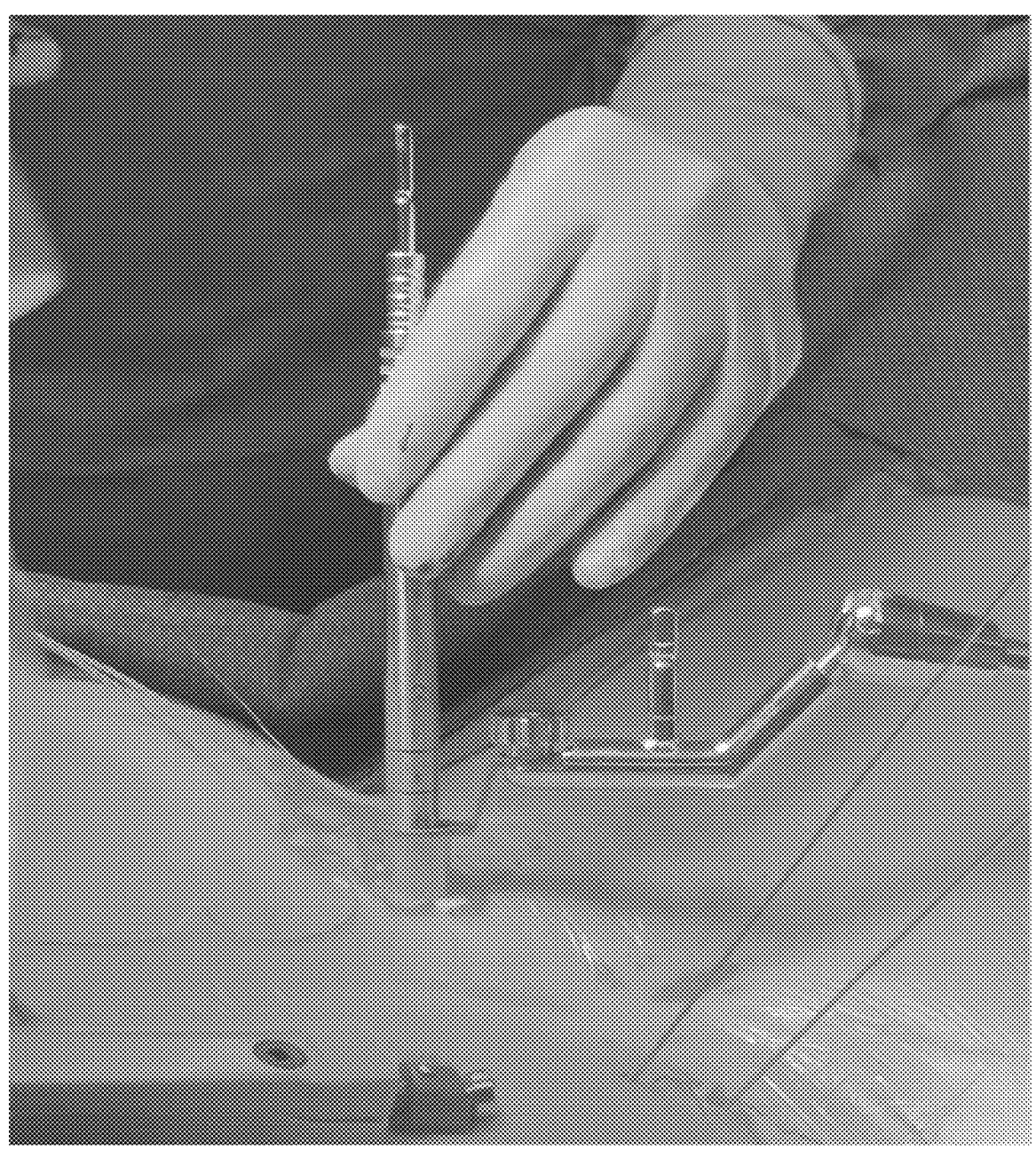
Figure 19E:
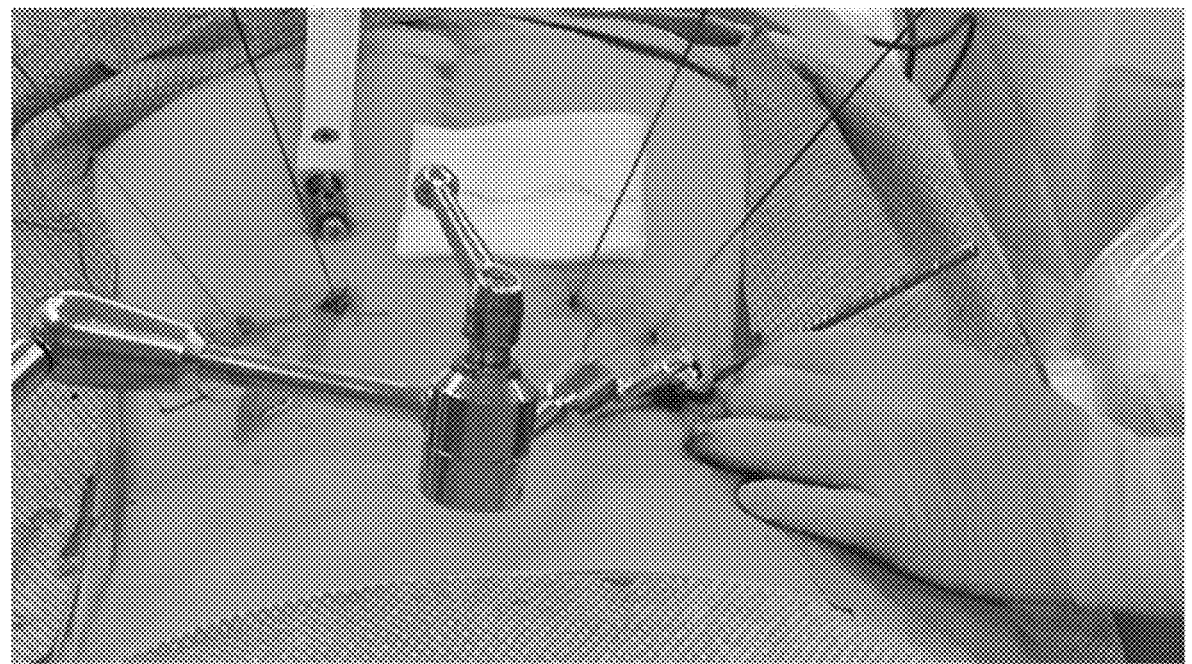
FIGS. 19E and 19F illustrate the larger dilators being removed in accordance with embodiments of the disclosure.
Figure 19F:
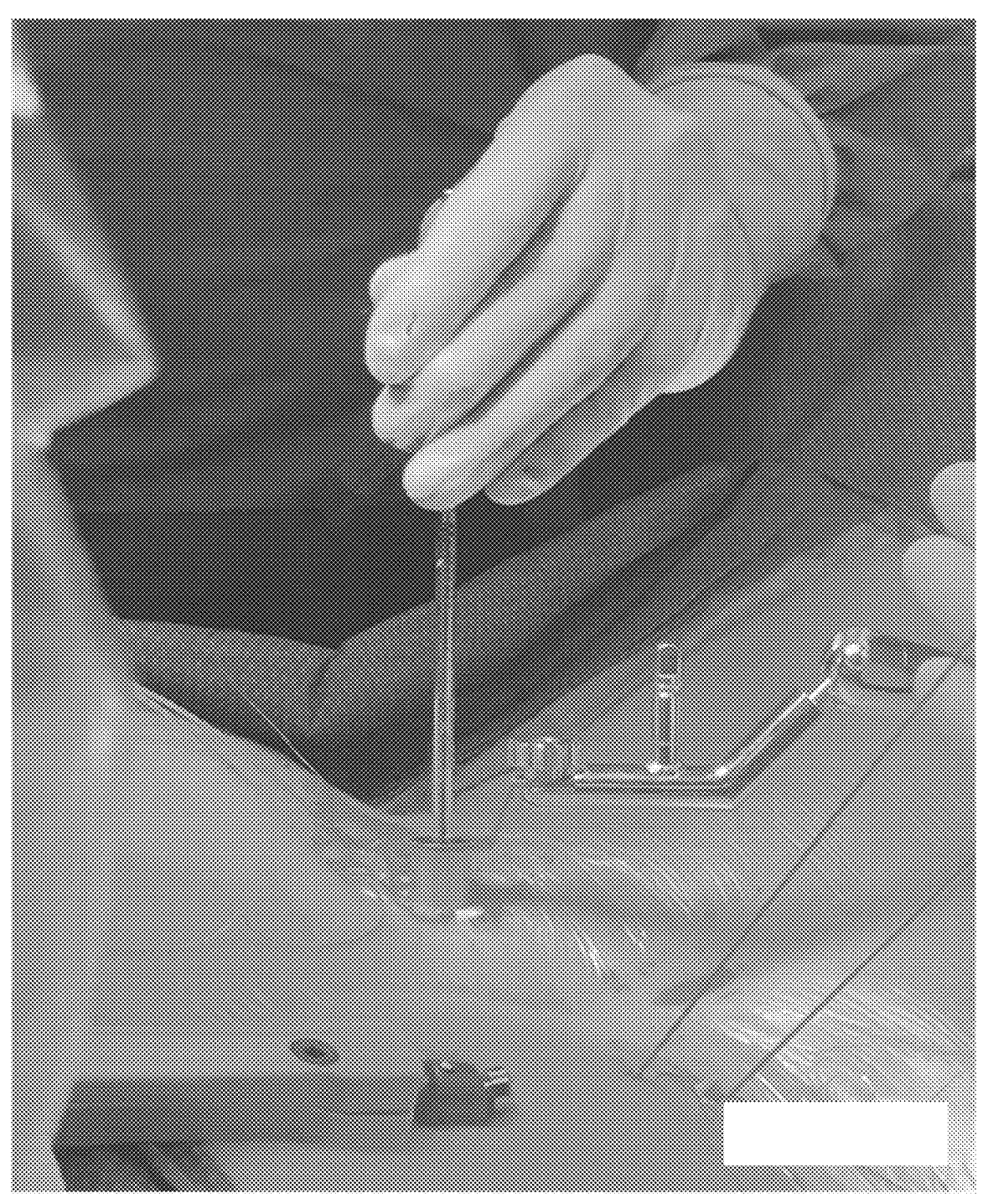

A navigated drill (FIG. 9) followed by a navigated 4 mm tap then may be placed into the pedicle (FIG. 10), followed by placement of a K-wire (FIG. 11). The K-wire may be lightly tapped into position (FIG. 12). The other K-wires then may be placed in a similar fashion on both sides (FIGS. 13A-F). The robotic arm guide then may be directed towards the target in the middle aspect of the facet joint, as described above, and following the trajectory created by the plan, as mentioned above. After infiltration with the local anesthetic and making the skin incision, the navigated one step dissector-dilator then may be advanced to the target. This may be followed by introducing a navigated drill (FIGS. 14A-E), followed by navigated taps, starting with a 4.5 mm tap (FIGS. 15A and 15B), followed by a 5.5 mm tap, a 6.5 mm tap, and finally a 7.5 mm tap. The taps may be watched with navigation to pass through the middle aspect of the facet joint as well as to enter the posterior third of the disc space (FIGS. 16A-D). This may be followed by placement of a K-wire, followed by placement of the first navigated dilator of a minimal access tube system (FIG. 17A). That dilator then may be advanced with a mallet towards the deeper portion of the facet joint so as to direct the following dilators and the metric tube in the correct accurate trajectory. Fluoroscopy in the AP, Lateral, and Oblique trajectories then may be utilized to make sure radiologically that there is no encroachment on the neural elements (FIGS. 17A-C). The larger dilators then may be placed (FIGS. 18A and 18B), after which an appropriate minimal access tube may be placed (FIGS. 19A and 19B). In some embodiments, larger tubes of 16 to 18 mm diameter may be used. In some embodiments, 14 mm diameter tubes (FIG. 19A) may be used, which may allow for excellent visualization with the intraoperative microscope, for minimal dissection of the paraspinal muscles, and for the introduction of all necessary instruments. In some embodiments, a radiolucent 13 mm diameter tube may be used. The tube then may be fixed in position to a Jackson table via a FlexArm (FIGS. 19C and 19D) to maintain the proper trajectory. The larger dilators may be removed first, followed by the smallest dilator (FIGS. 19E and 19F). The pedicle screw K-wires then may be deflected away using Ellis clamps so as not to interfere with further movements of the robotic arm guide or with movements of the microscope or other instruments (FIG. 20A).

Figure 20A:
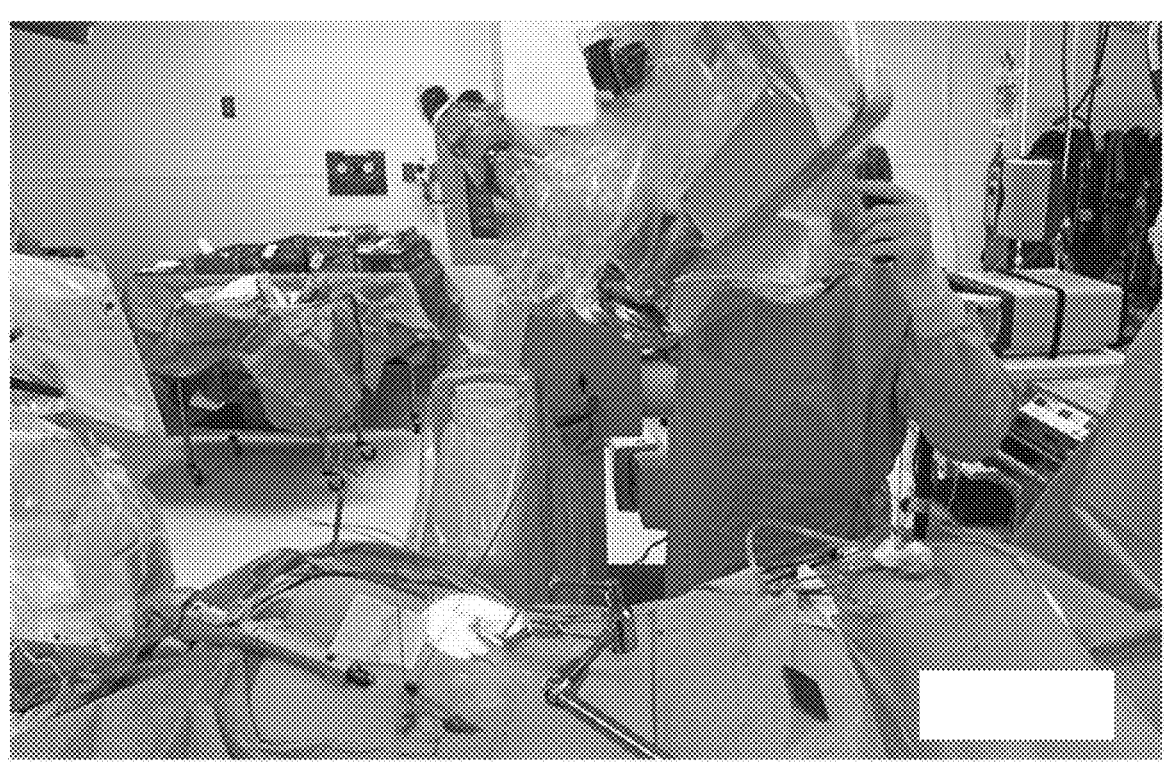
FIGS. 20A and 20B illustrate a microscope being introduced into the field to visualize the entry point area of the access corridor through the minimal access tube in accordance with embodiments of the disclosure.
Figure 20B:
Figure 21A:
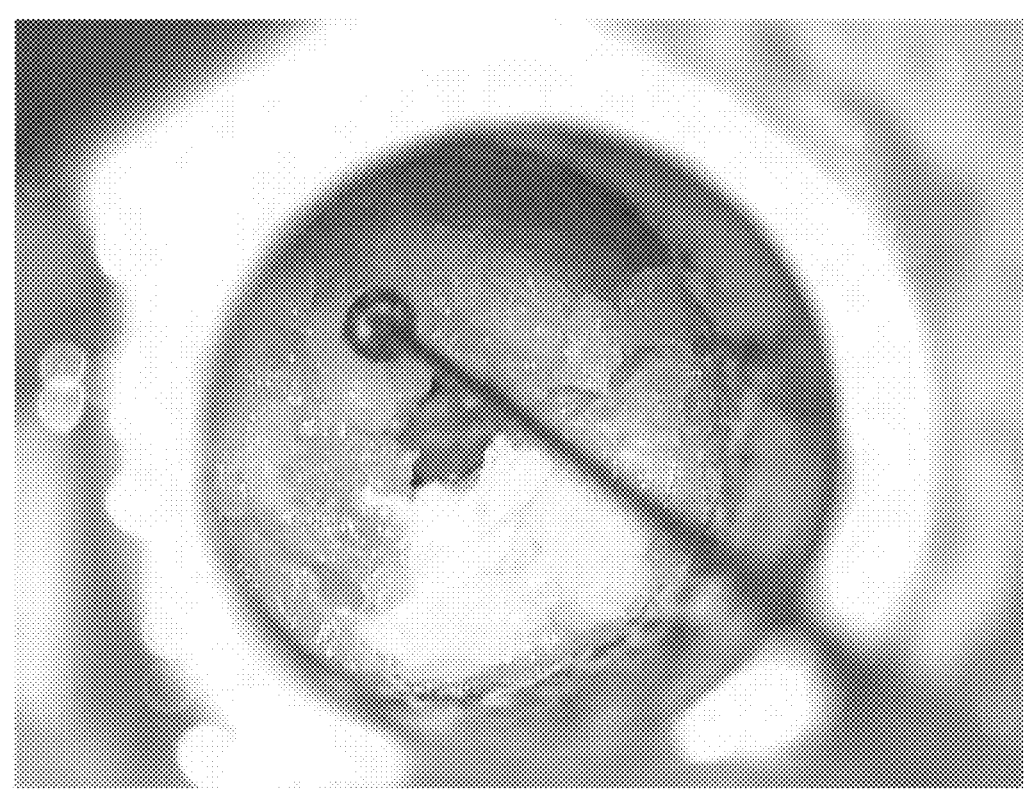
FIGS. 21A and 21B illustrate inspection of the access corridor using a dissector in accordance with embodiments of the disclosure.
Figure 21B:
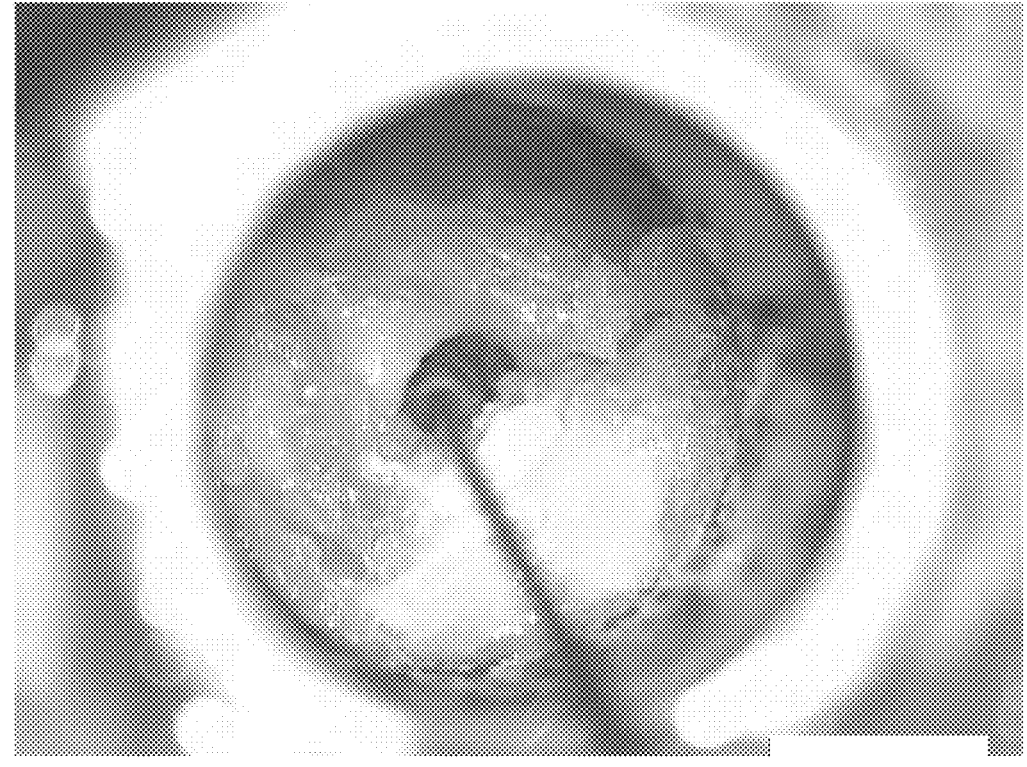
Figure 22A:
FIGS. 22A, 22B, and 22C illustrate positioning of the robotic arm guide towards the facet joint in accordance with embodiments of the disclosure.
Figure 22B:
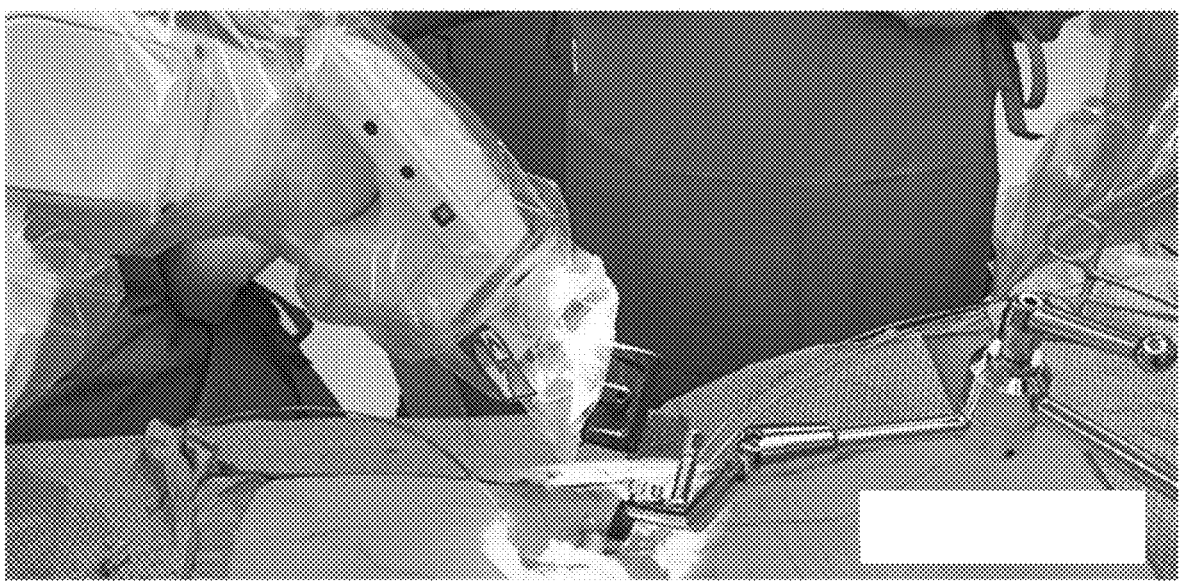
Figure 22C:
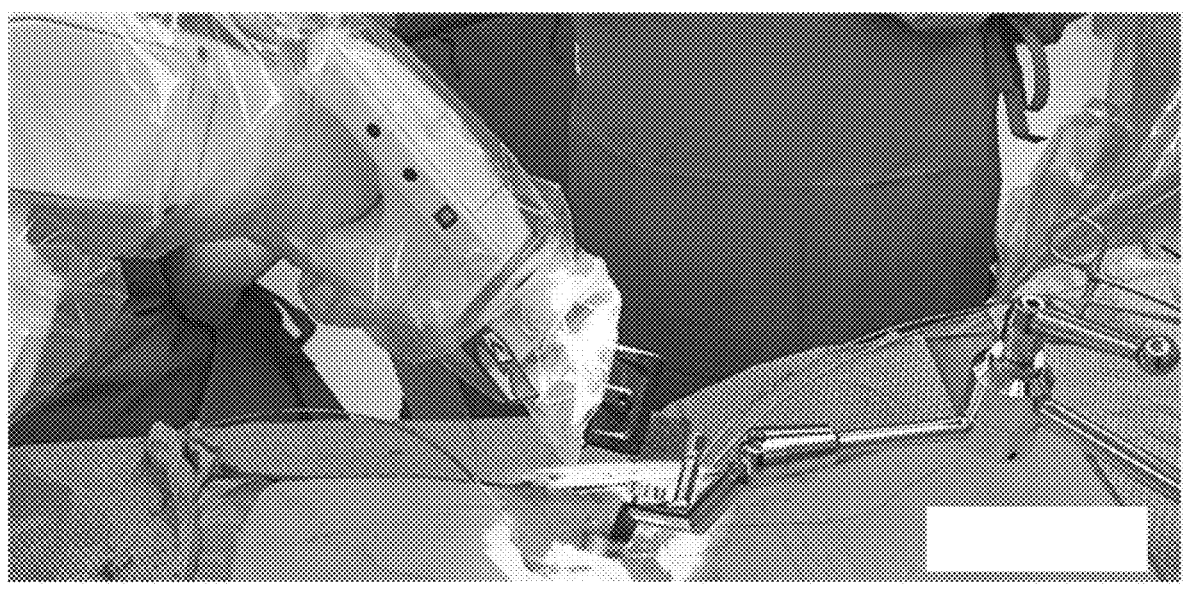
Figure 23A:
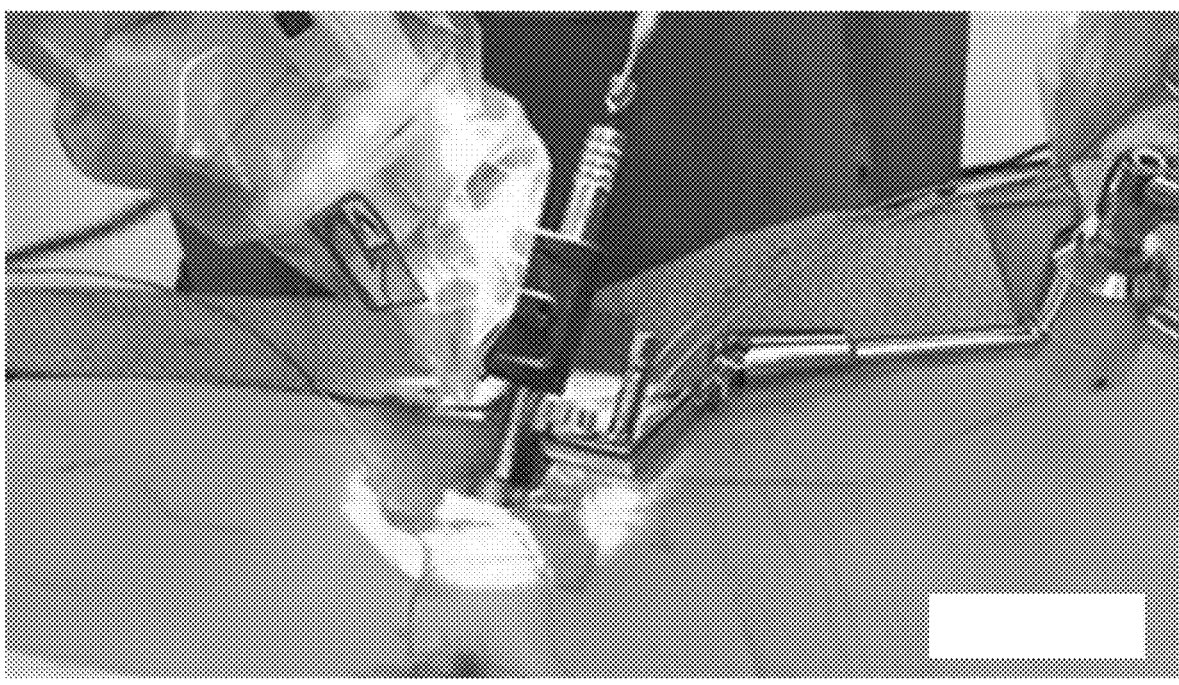
FIGS. 23A and 23B illustrate placement of a reducer dilator tube through the robotic arm guide and introduction of a drill with an acorn drill bit through the reducer dilator tube in accordance with embodiments of the disclosure.
Figure 23B:
Figure 24A:
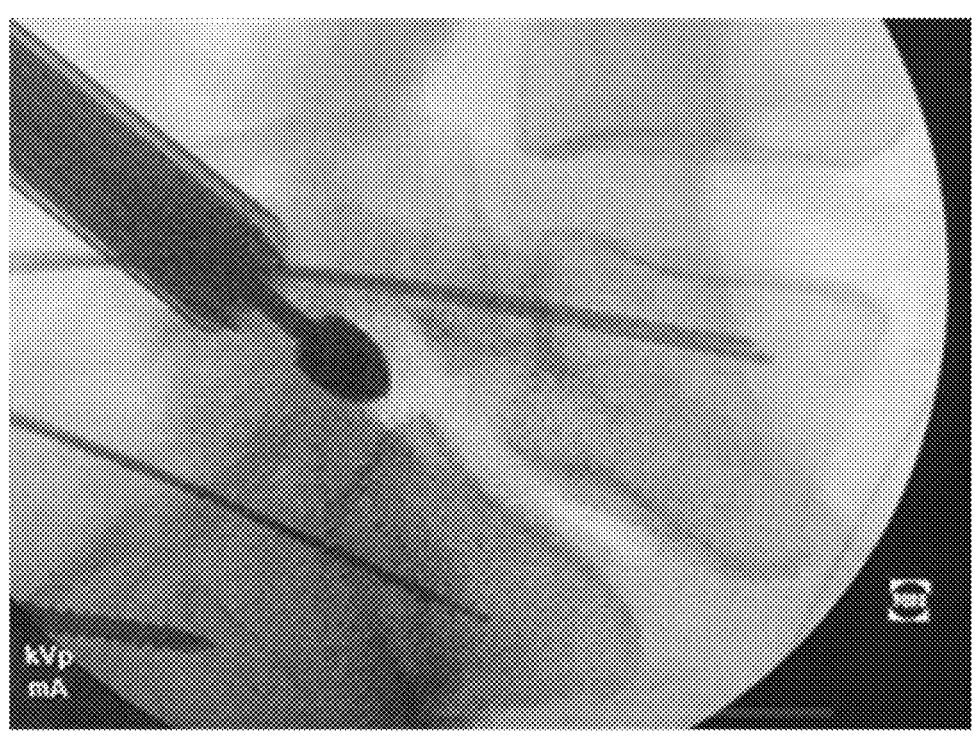
FIG. 24A illustrates the drill being used to drill into the facet joint in accordance with embodiments of the disclosure.

A microscope (or endoscope) then may be brought into the field from the left side of the patient beside the left shoulder to visualize the entry point area through the access tube (FIGS. 20A and 20B). The surgeon then may introduce an angled dissector or a ball-tip dissector through the 7.5 mm tapped area to feel the spirals created all around to ensure the accuracy of the approach and to make sure that the bony surroundings are not compromised (FIGS. 21A and 21B). The microscope then may be moved away, keeping the stand in its position, and the robotic arm guide then may be brought back again directed towards the facet target (FIGS. 22A-C). The surgeon then may introduce a 12 mm reducer dilator tube through the robotic arm guide and through the access tube to fine tune its trajectory (FIG. 23). Lateral fluoroscopy then may be employed from this point onwards. The C-arm stand may be brought in from the right side of the patient at shoulder level underneath the table and moved downwards to view the approach into the facet joint and the disc space. The Midas Rex drill with a 9 mm diameter Acorn drill bit then may be introduced through the 12 mm reducer tube directed towards the target (FIGS. 23A, 23B, 35A, and 35B), drilling into the facet joint under fluoroscopy (FIG. 24A). The 12 mm reducer tube and the robotic arm guide then may be set aside, and the microscope may be brought again into the field. The microscope may be raised upwards to allow for the instrumentation to be introduced while still visualizing the entry point.

Figure 24B:
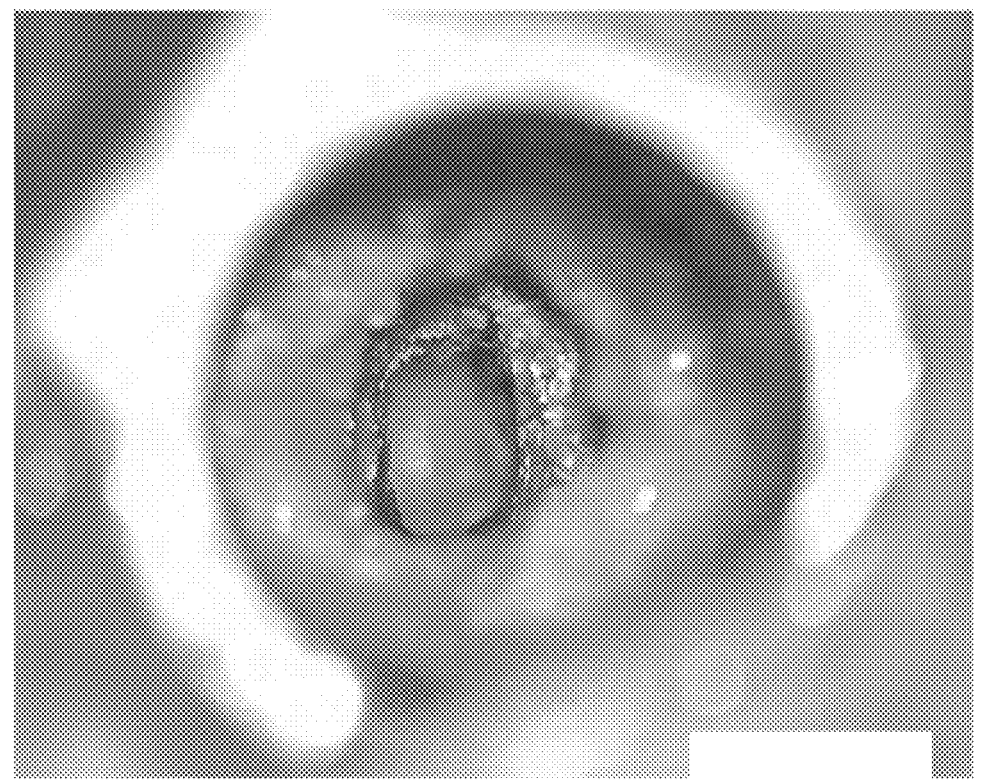
FIG. 24B illustrates an opening created by the drill in accordance with embodiments of the disclosure.
Figure 24C:
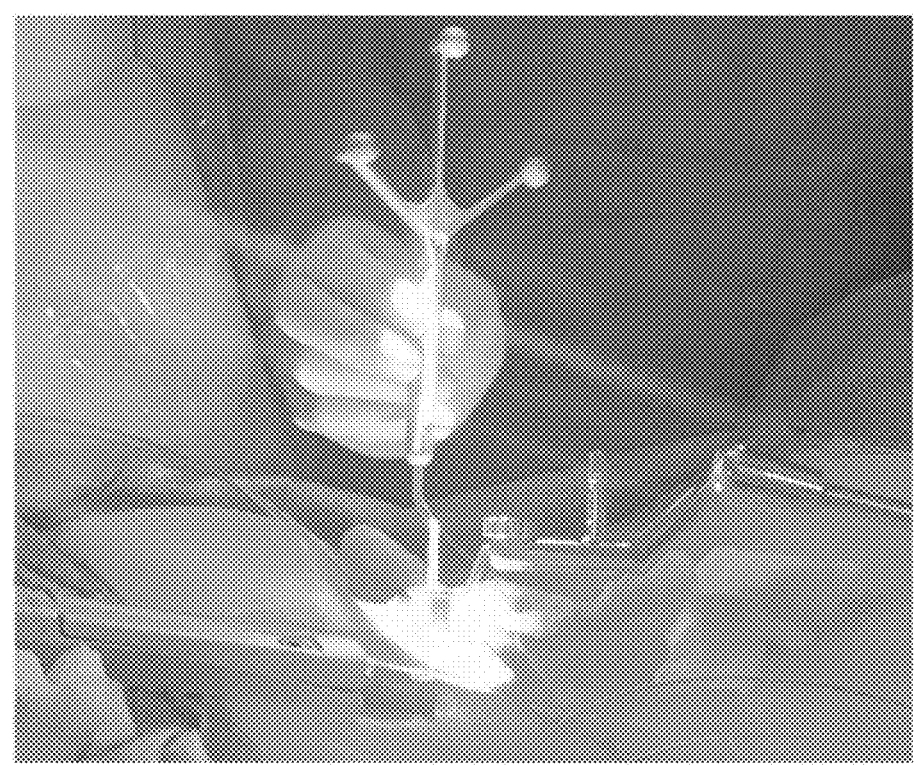
FIGS. 24C and 24D illustrate introduction of a navigated dissector into the opening to confirm the approach in accordance with embodiments of the disclosure.
Figure 24D:
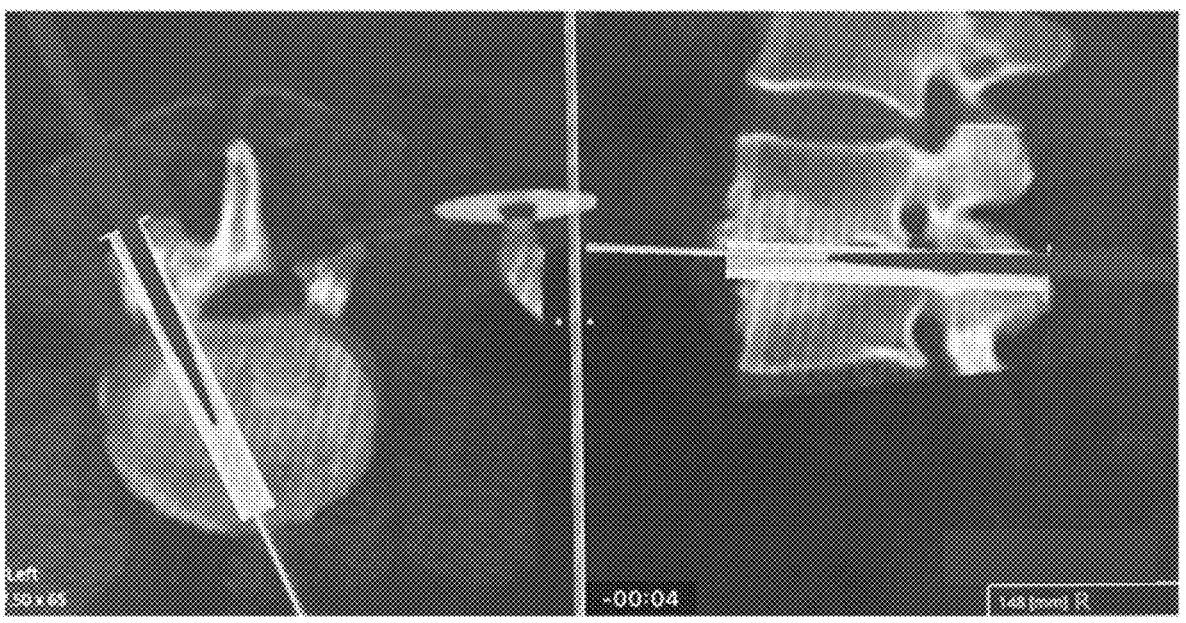
Figure 25A:
FIGS. 25A, 25B, 25C, and 25D illustrate sequential introduction of two distractors to open up the collapsed disc space in accordance with embodiments of the disclosure.
Figure 25B:
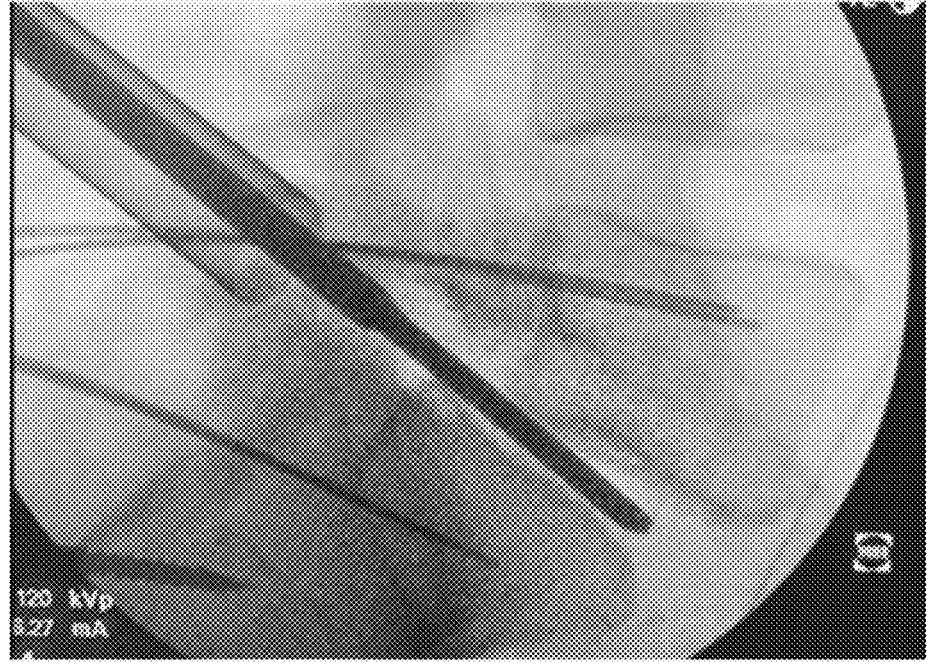
Figure 25C:
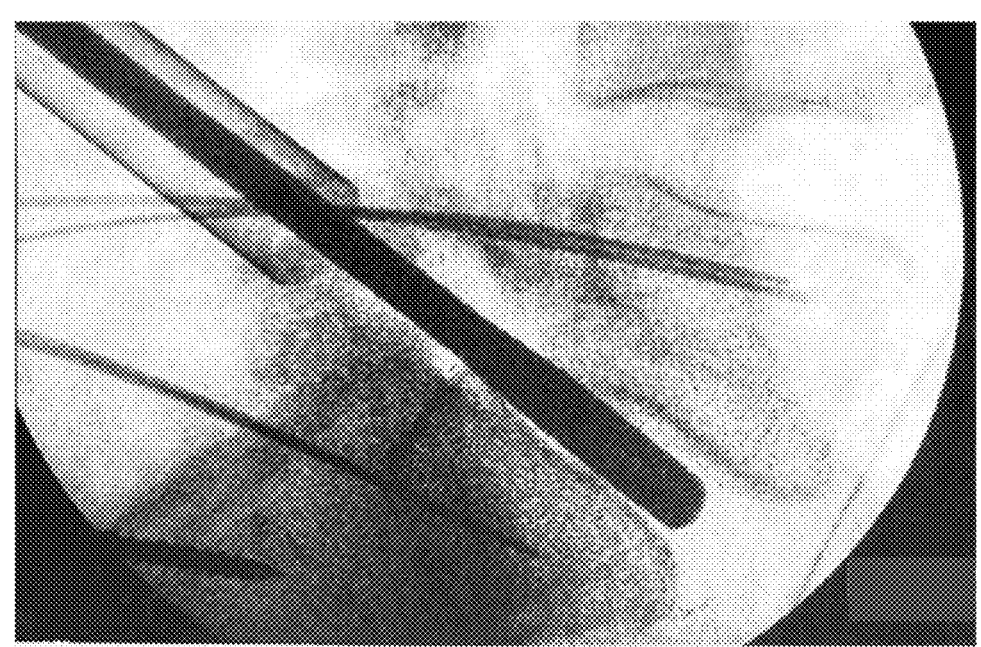
Figure 25D:
Figure 26:
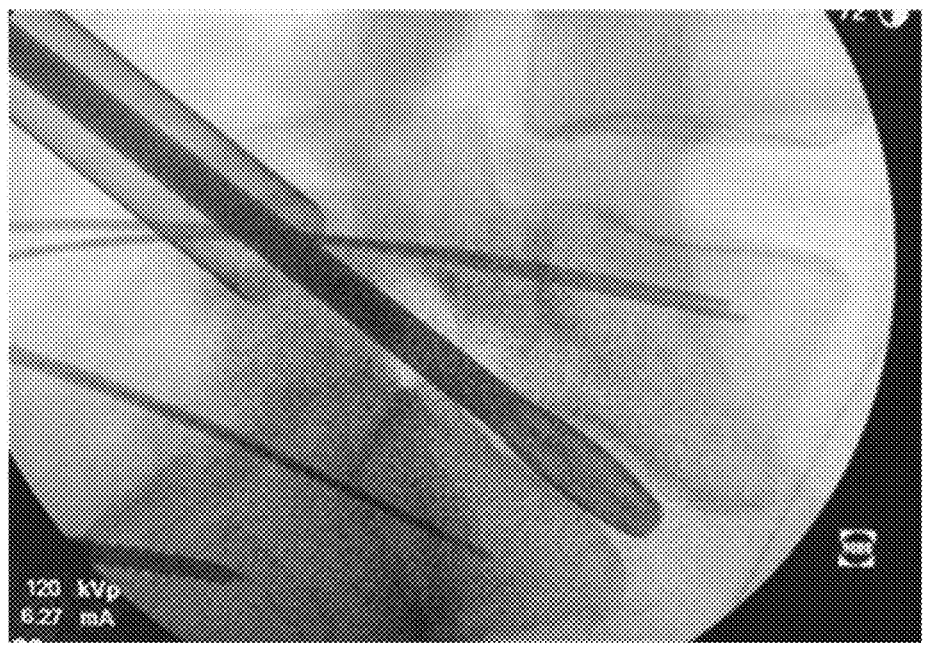
FIG. 26 illustrates placement of a shaver into the disc space in accordance with embodiments of the disclosure.
Figure 27:
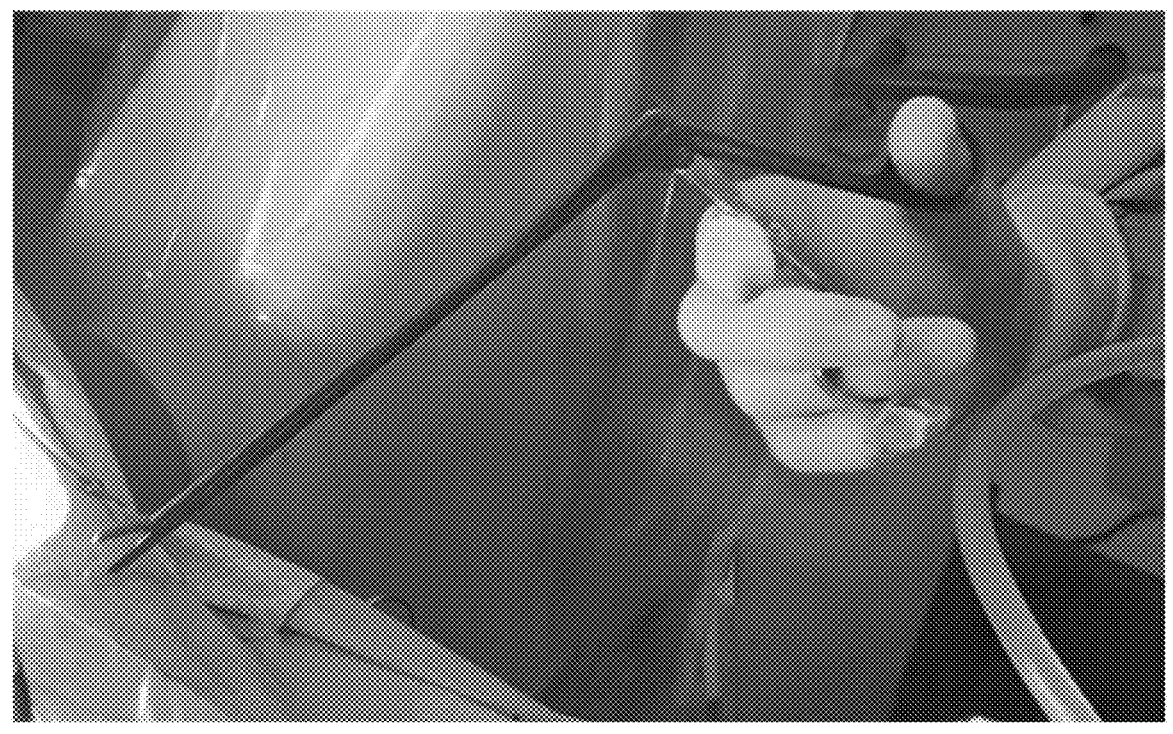
FIG. 27 illustrates introduction of a pituitary rongeur to remove the shaved off cartilaginous endplates and degenerated disc material in accordance with embodiments of the disclosure.
Figure 28A:
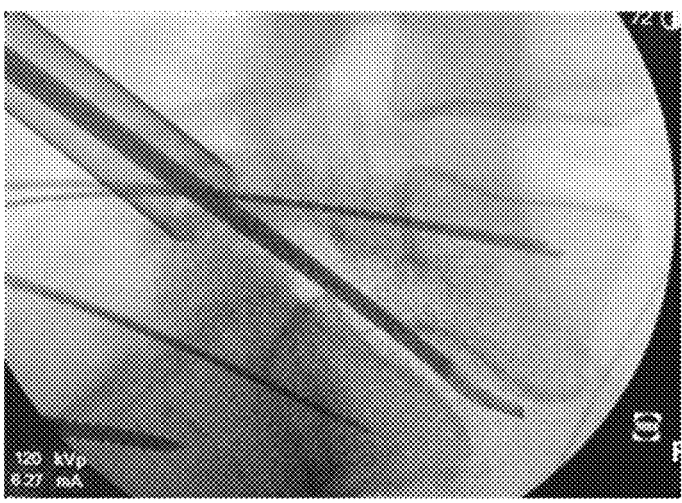
FIGS. 28A, 28B, 28C, 28D, and 28E illustrate placement of ring curettes to curette the remaining portions of the cartilaginous endplates in accordance with embodiments of the disclosure.
Figure 28B:
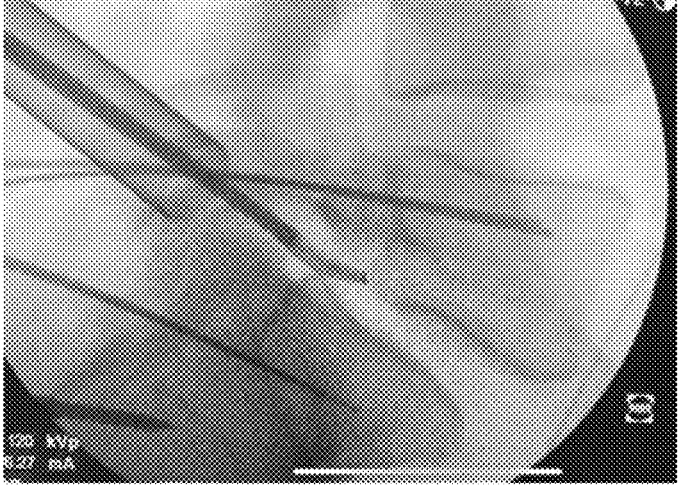
Figure 28C:
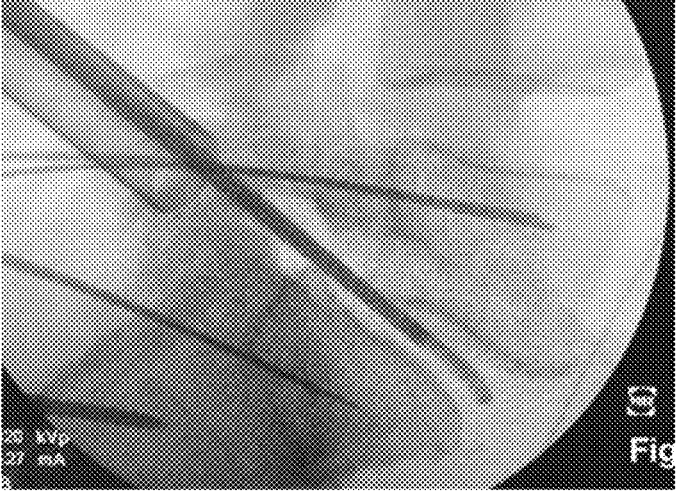
Figure 28D:
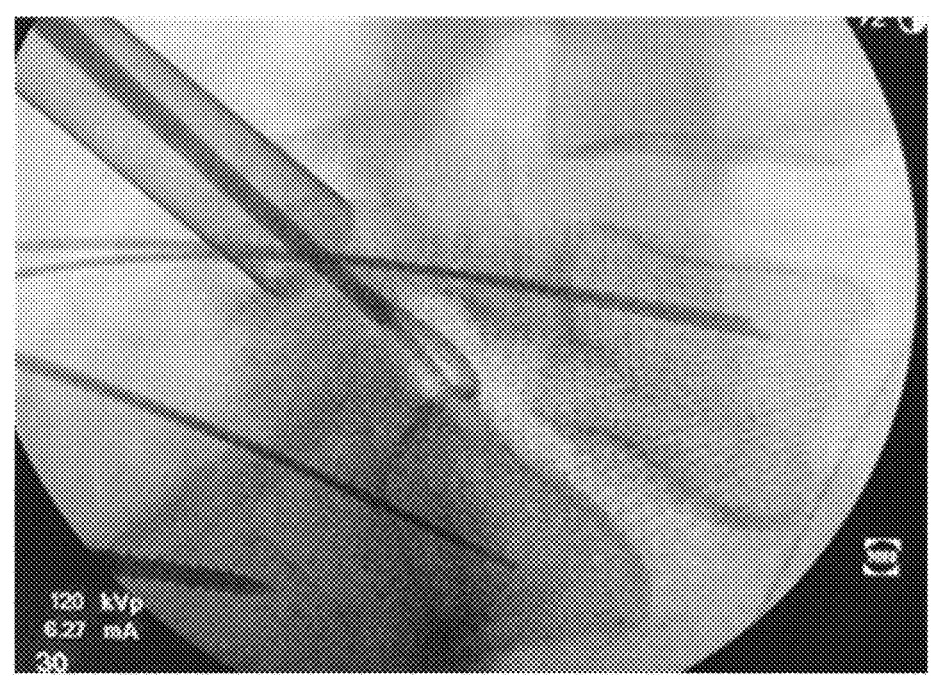
Figure 28E:
Figure 29A:
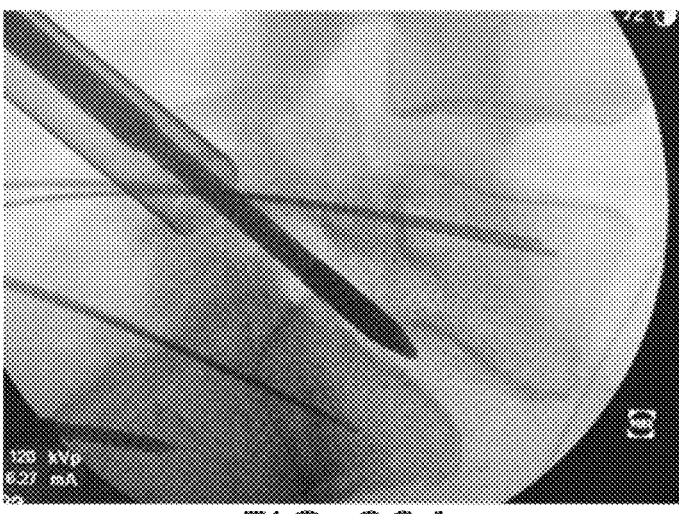
FIGS. 29A, 29B, and 29C illustrate placement of a wedge trial or sizing instrument into the disc space to determine a size of a cage to be used in accordance with embodiments of the disclosure.
Figure 29B:
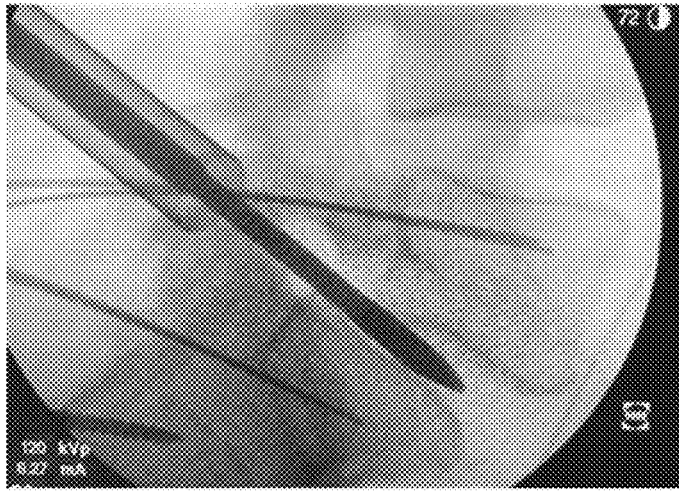
Figure 29C:
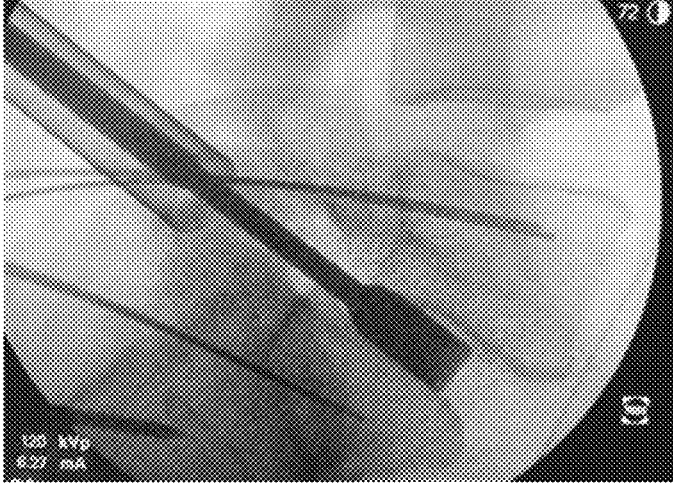
Figure 37:
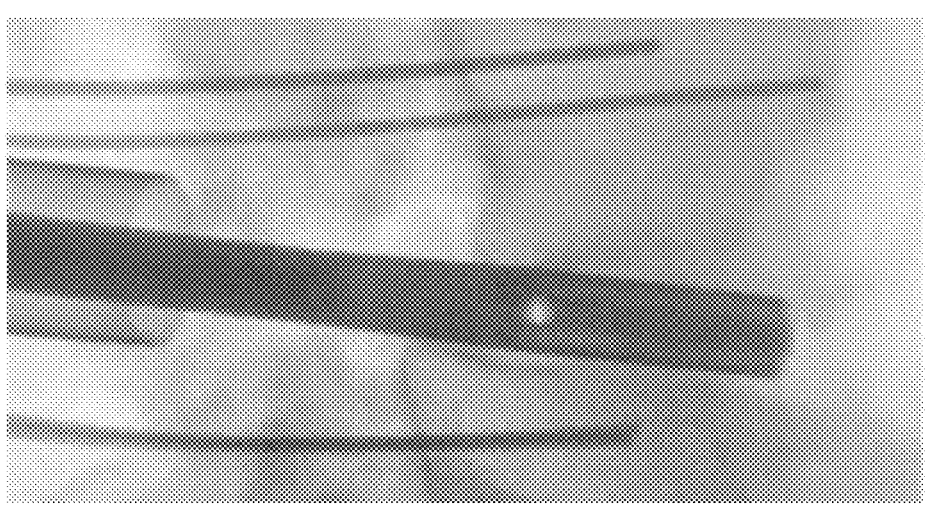
FIG. 37 illustrates placement of the shaver into the disc space in accordance with embodiments of the disclosure.
Figure 38A:
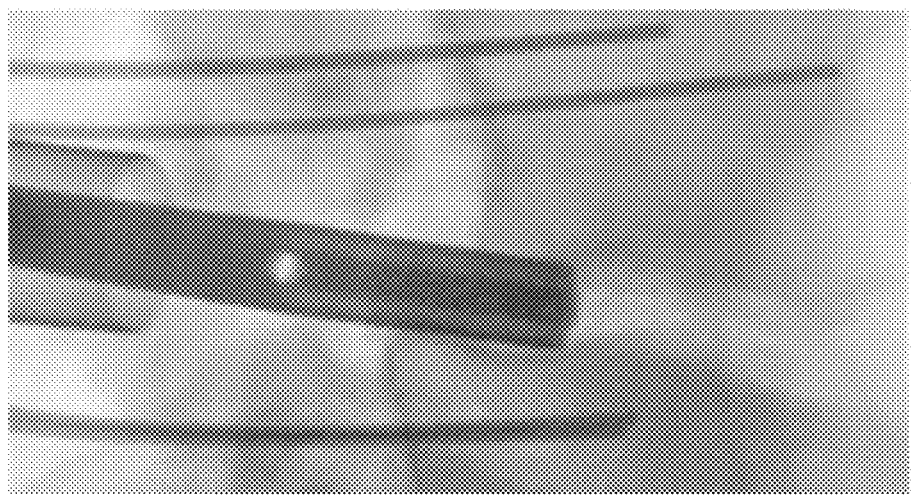
FIGS. 38A and 38B illustrate the shaver being used to shave the anterior-most portion of the disc space as well as the middle and posterior aspects of the disc space in accordance with embodiments of the disclosure.
Figure 38B:
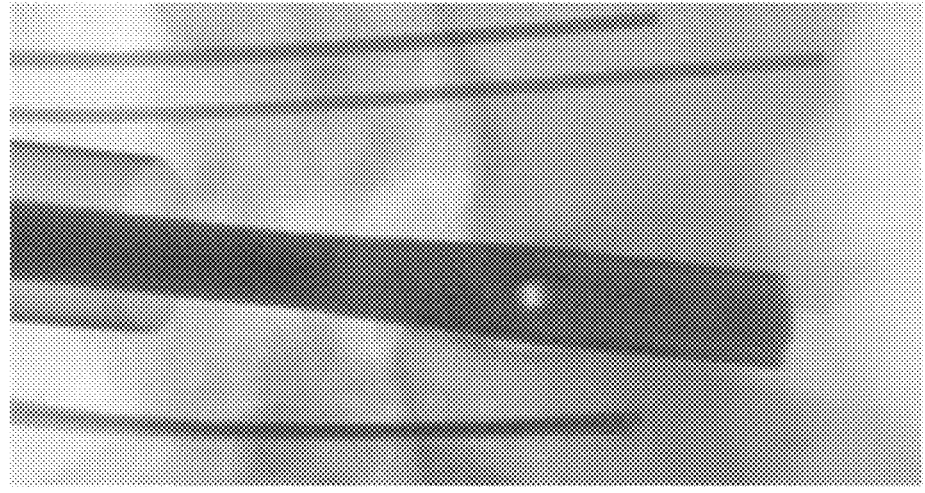
Figure 39A:
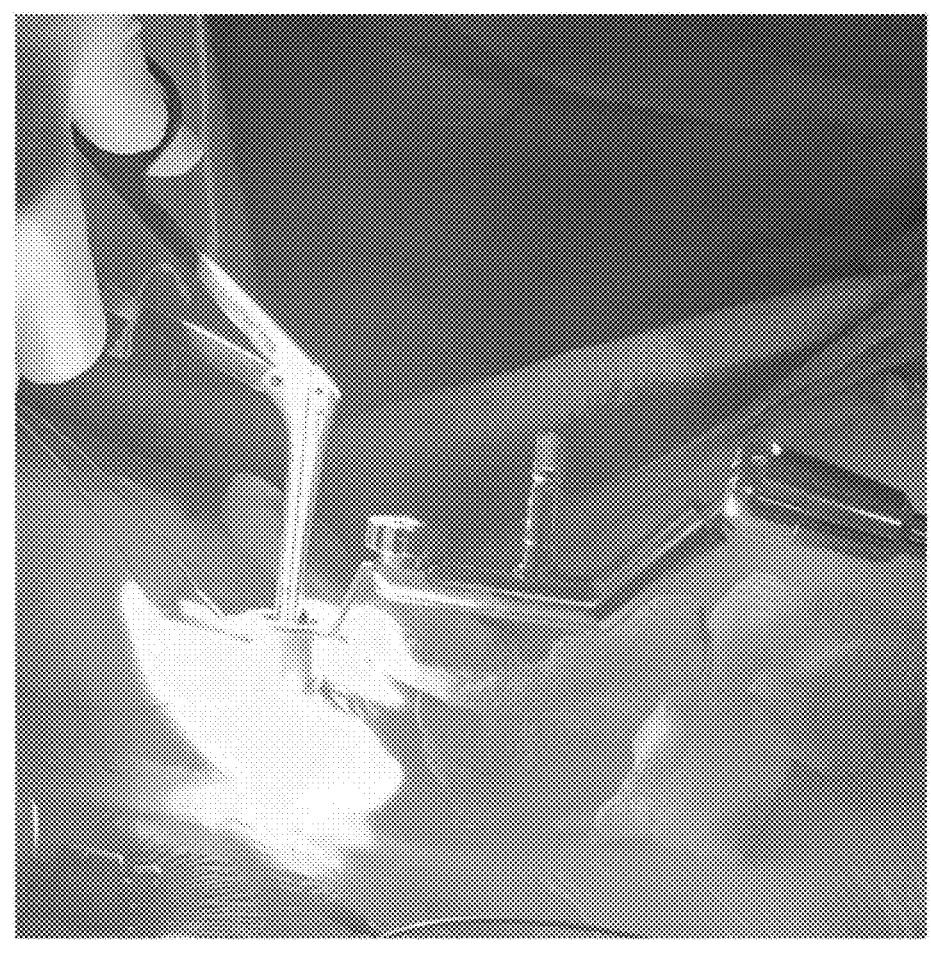
FIGS. 39A and 39B illustrate the pituitary rongeur being used to remove the shaved off cartilaginous endplates and degenerated disc material in accordance with embodiments of the disclosure.
Figure 39B:
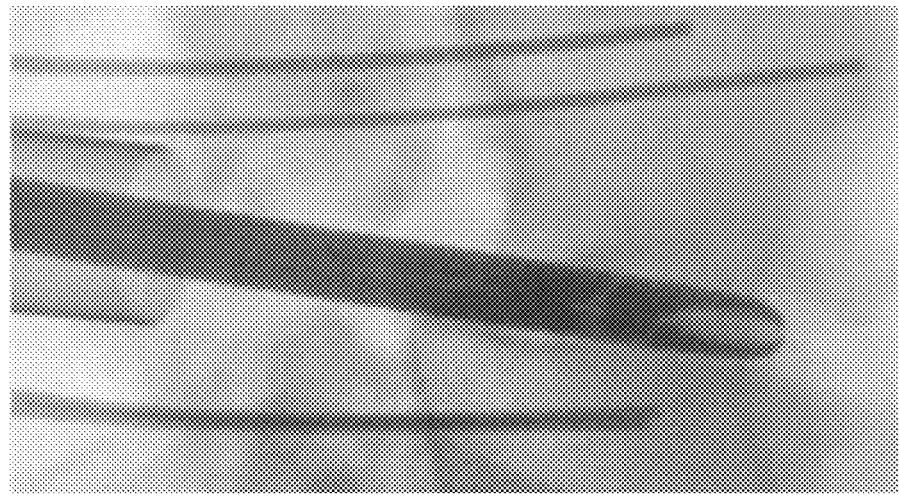
Figure 40A:
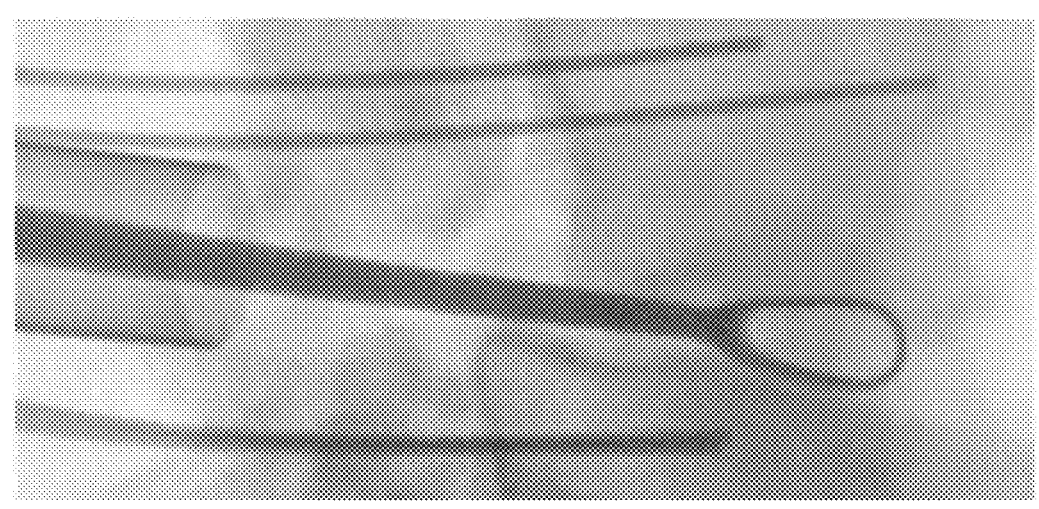
FIGS. 40A, 40B, and 40C illustrate the ring curettes being used to curette the remaining portions of the cartilaginous endplates in accordance with embodiments of the disclosure.
Figure 40B:
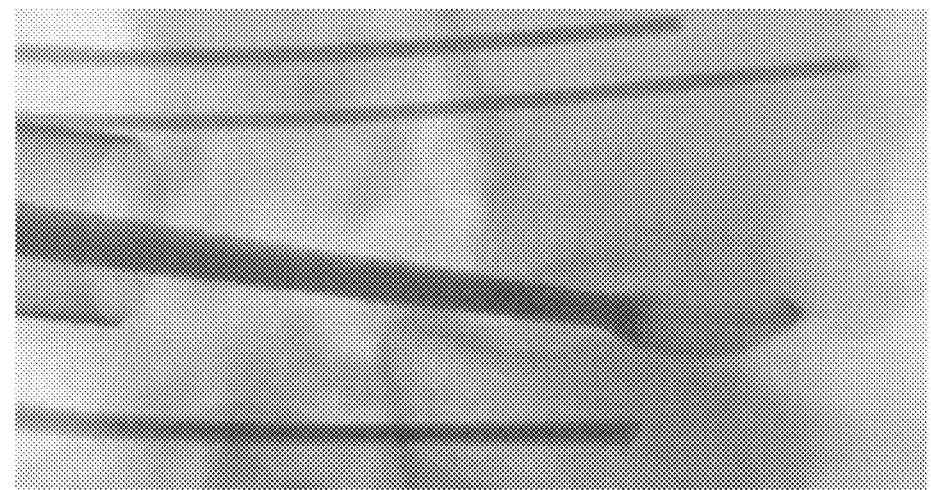
Figure 40C:
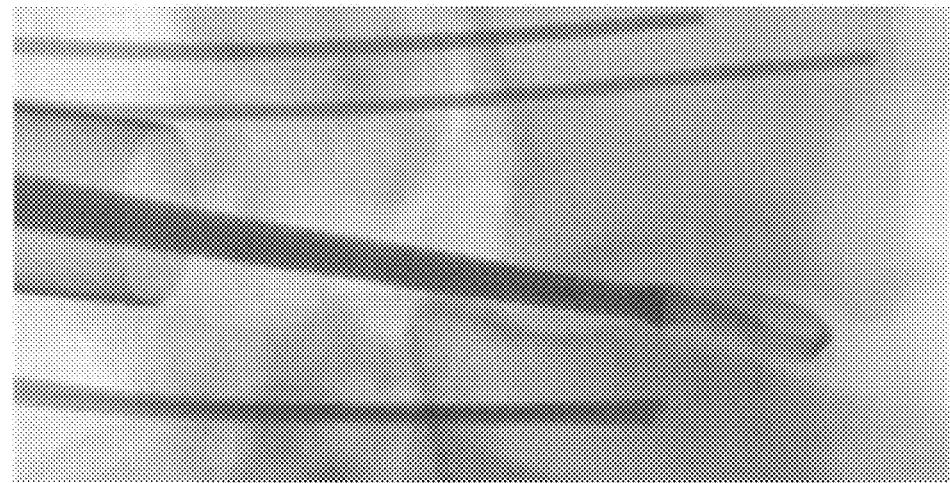
Figure 41:
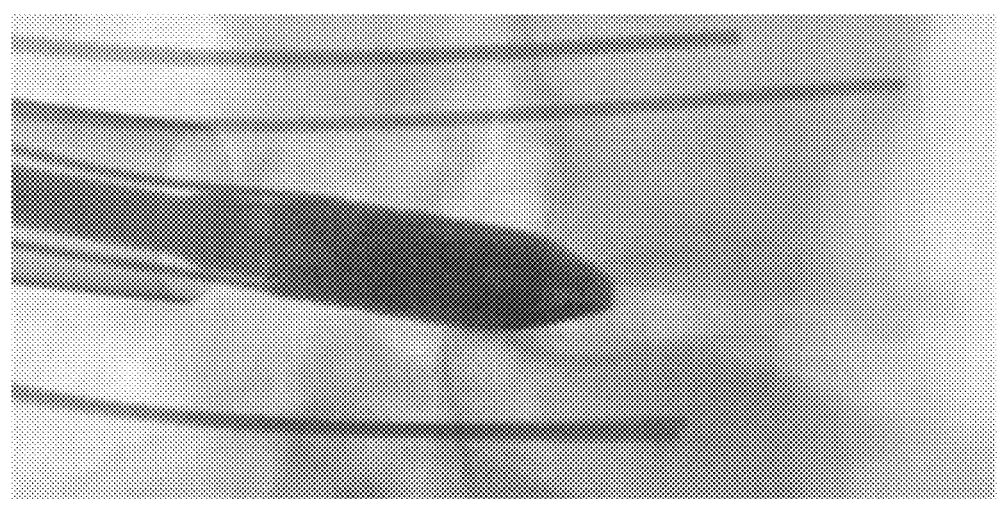
FIGS. 41, 42, and 43 illustrate the wedge trial or sizing instrument being used to determine a size of a cage to be used in accordance with embodiments of the disclosure.
Figure 42:
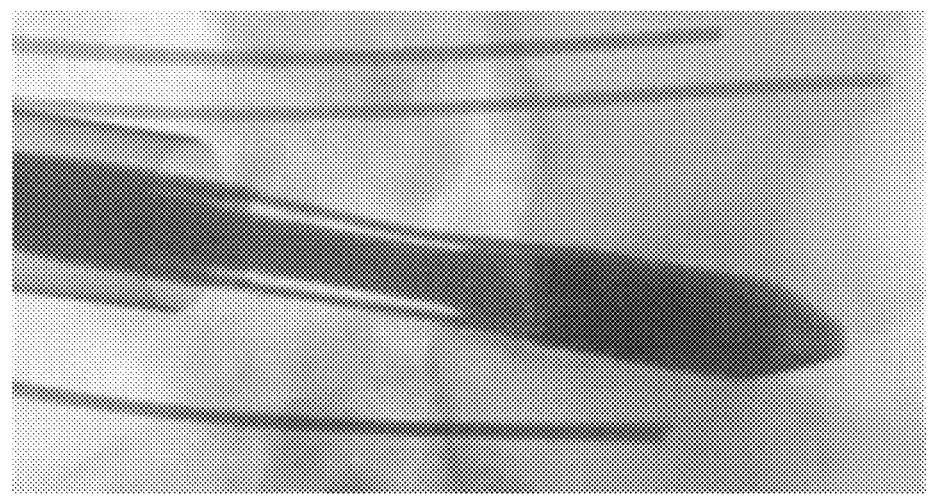
Figure 43:
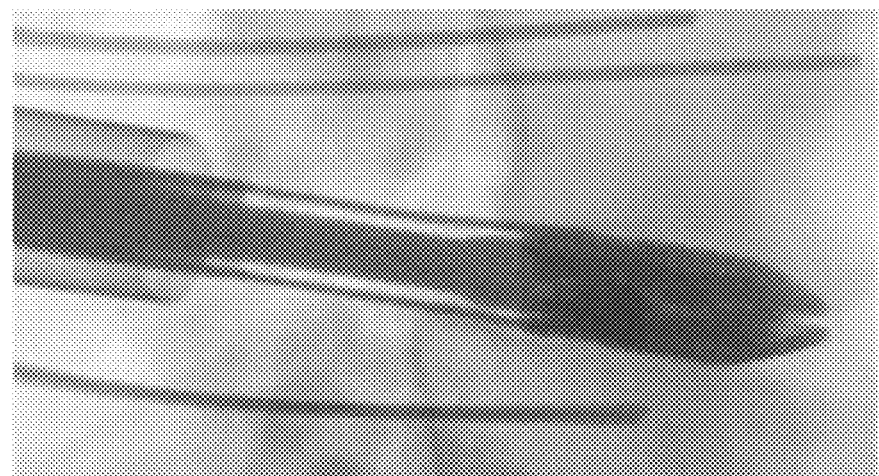
Figure 44A:
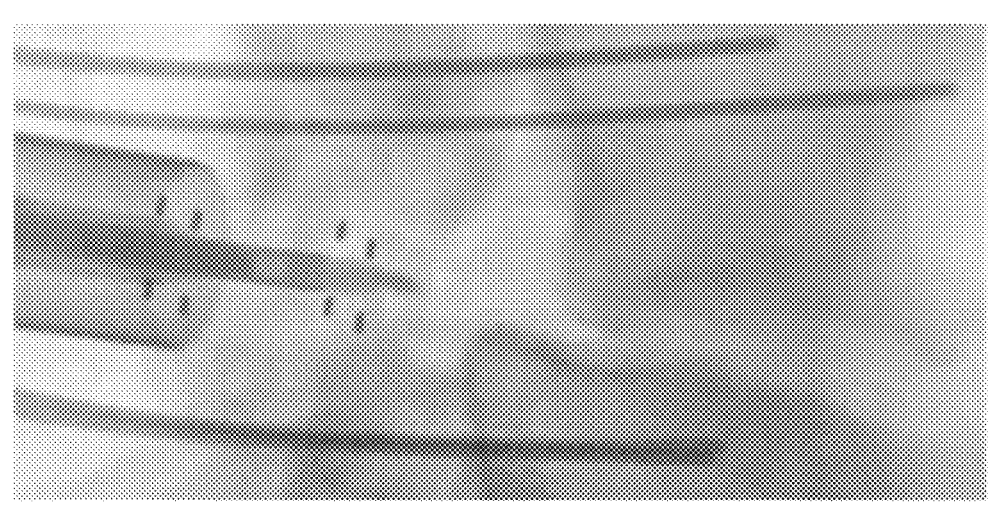
FIGS. 44A, 44B, 44C, and 44D illustrate placement of the expandable cage into the disc space in accordance with embodiments of the disclosure.
Figure 44B:
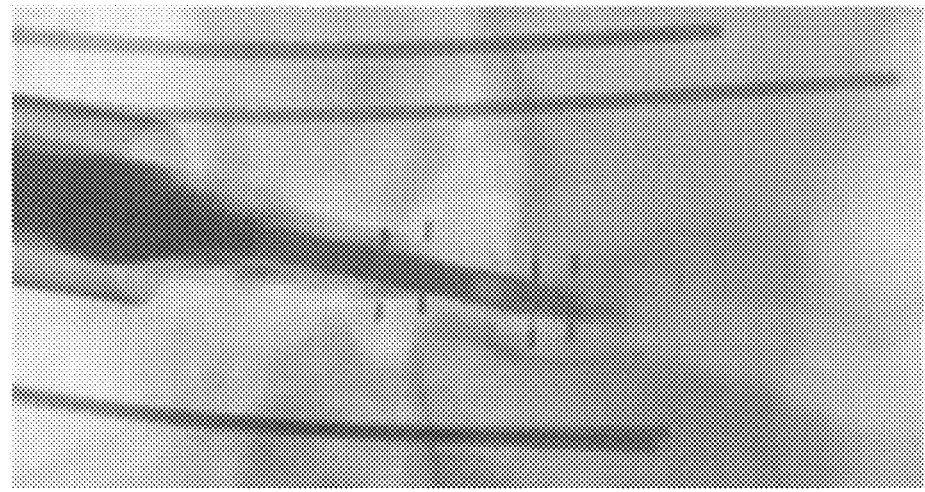
Figure 44C:
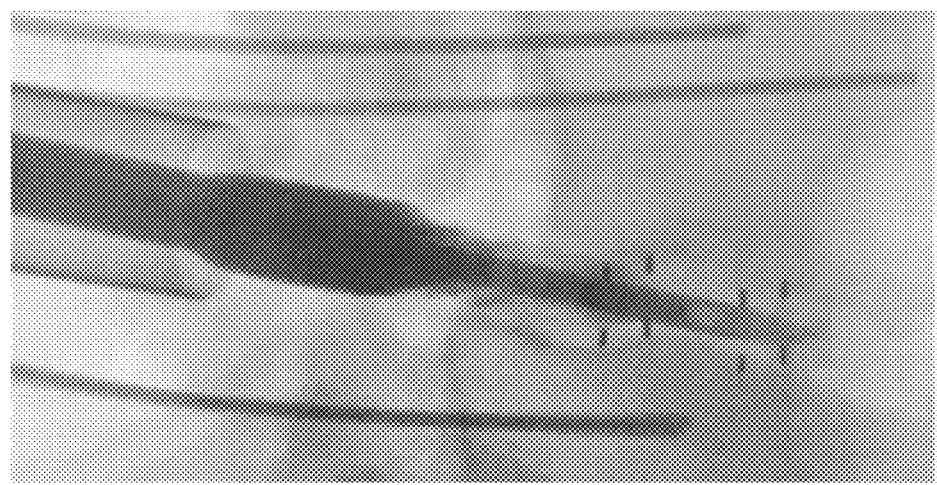
Figure 44D:
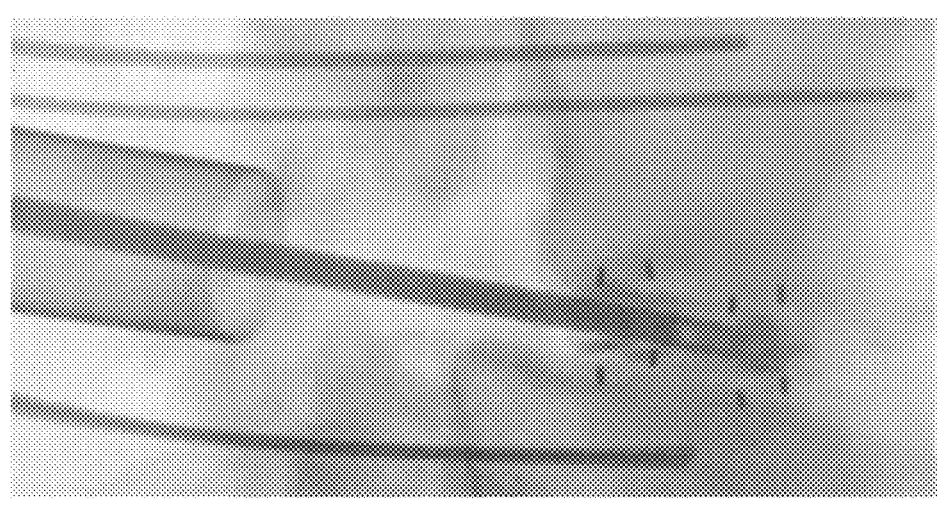
Figure 45:
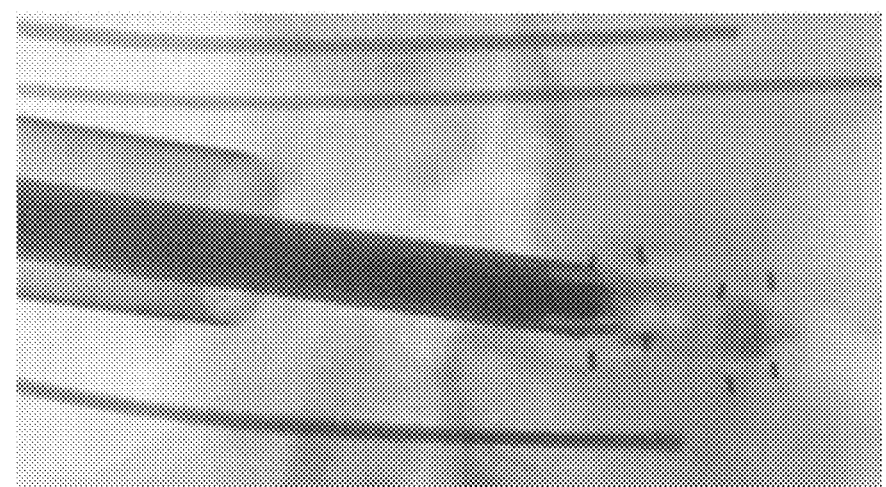
FIG. 45 illustrates expansion of the expandable cage within the disc space and filling of the expanded cage with graft material in accordance with embodiments of the disclosure.

Through the opening created by the Midas Rex (FIG. 24B), the surgeon then may introduce a navigated dissector (FIG. 24C) which may be visualized on the navigation screen confirming the accuracy of the approach (FIG. 24D). The surgeon then may sequentially introduce 6 mm and 7 mm distractors to open up the collapsed disc space (FIGS. 25A-D, 36A, and 36B), followed by placement of an 8 mm shaver (FIGS. 26 and 37). The surgeon may shave the anterior-most portion of the interspace as well as the middle and posterior aspects of the interspace (FIGS. 38A and 38B). Depending on the size of the cage used, the surgeon may also introduce 9 mm and 10 mm shavers only in the area of the facet joint to allow for placement of the cage. Larger size shavers may also need to be used inside the interspace depending on the disc height, however care should be taken not to violate the bony endplates. An expandable shaver may also be utilized. A pituitary rongeur then may be introduced under fluoroscopy to remove the shaved off cartilaginous endplates and degenerated disc material (FIGS. 27, 39A, and 39B), followed by placement of ring curettes to curette the remaining portions of the cartilaginous endplates (FIGS. 28A-E and 40A-C). This may be an advantageous step to ensure successful bony fusion. The pituitary rongeur may be used again to remove all curetted material.

Figure 30A:
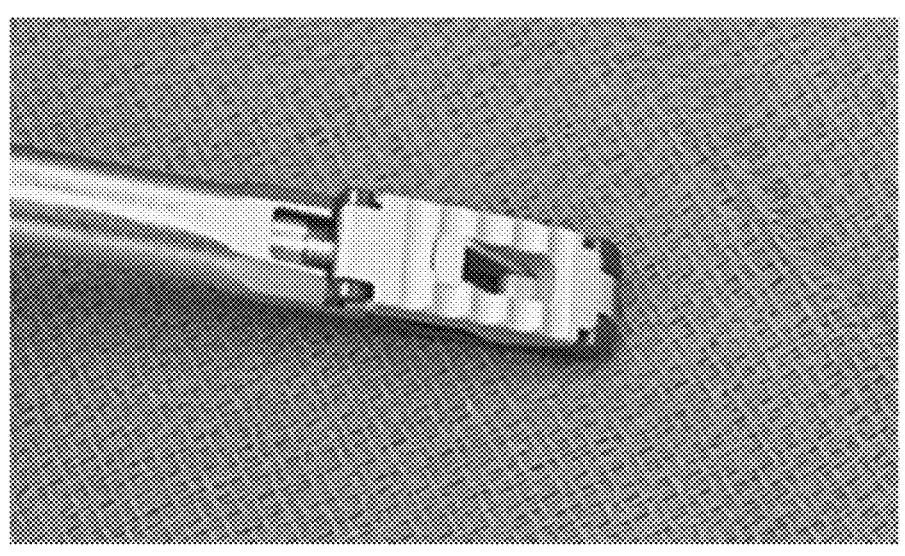
FIGS. 30A and 30B illustrate an expandable cage as may be used in accordance with embodiments of the disclosure.
Figure 30B:
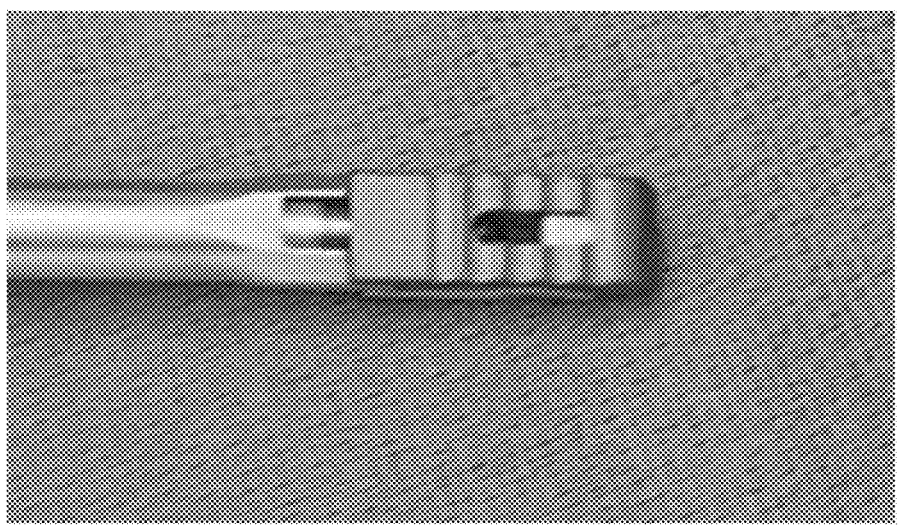
Figure 31A:
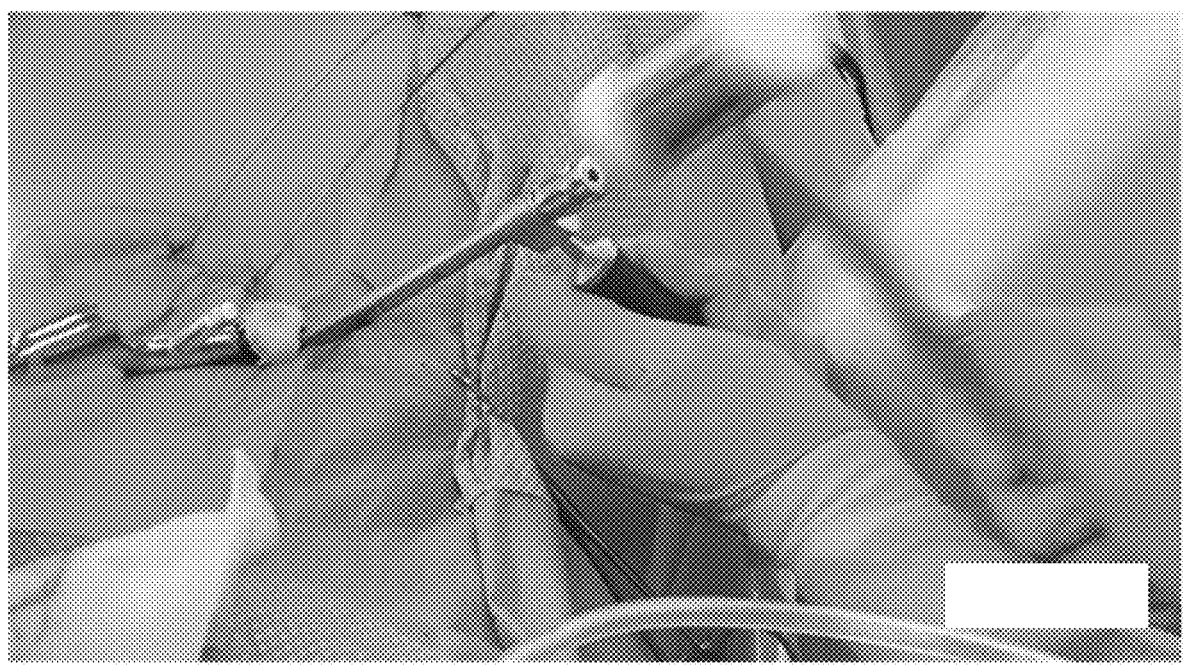
FIGS. 31A, 31B, 31C, and 31D illustrate placement of the expandable cage into the disc space in accordance with embodiments of the disclosure.
Figure 31B:
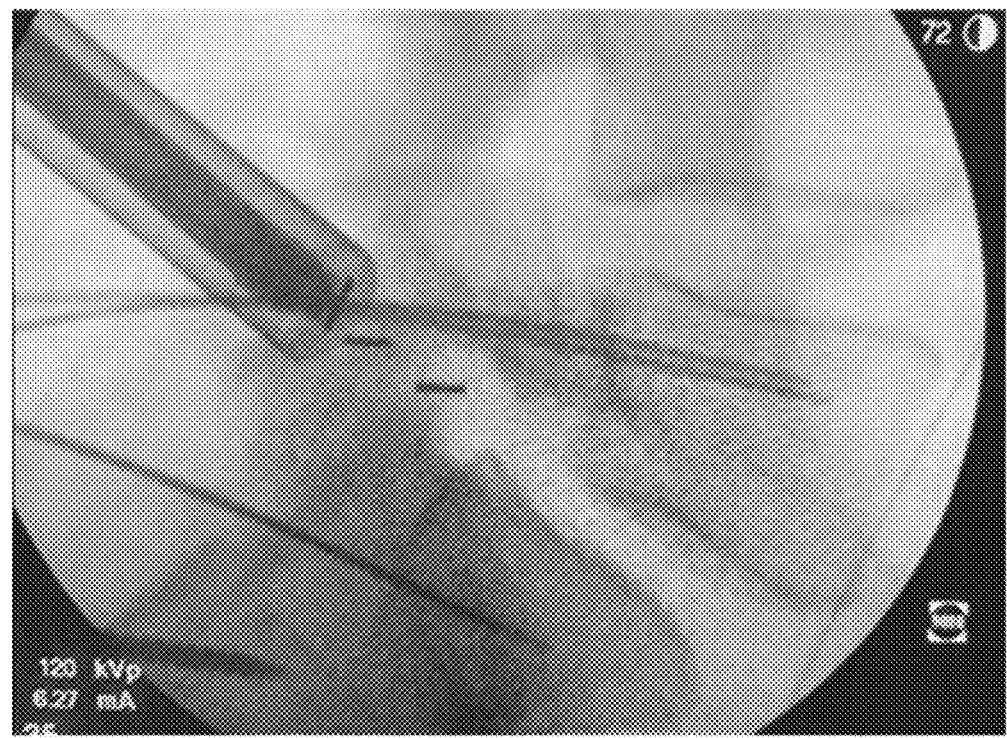
Figure 31C:
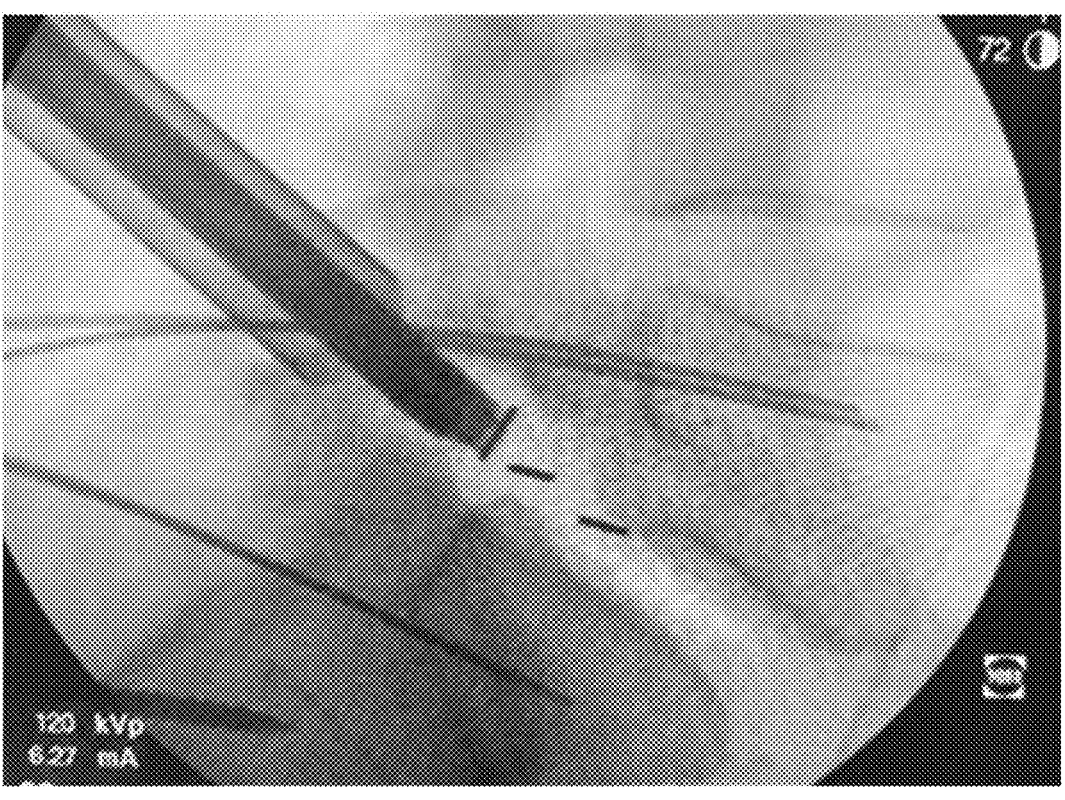
Figure 31D:
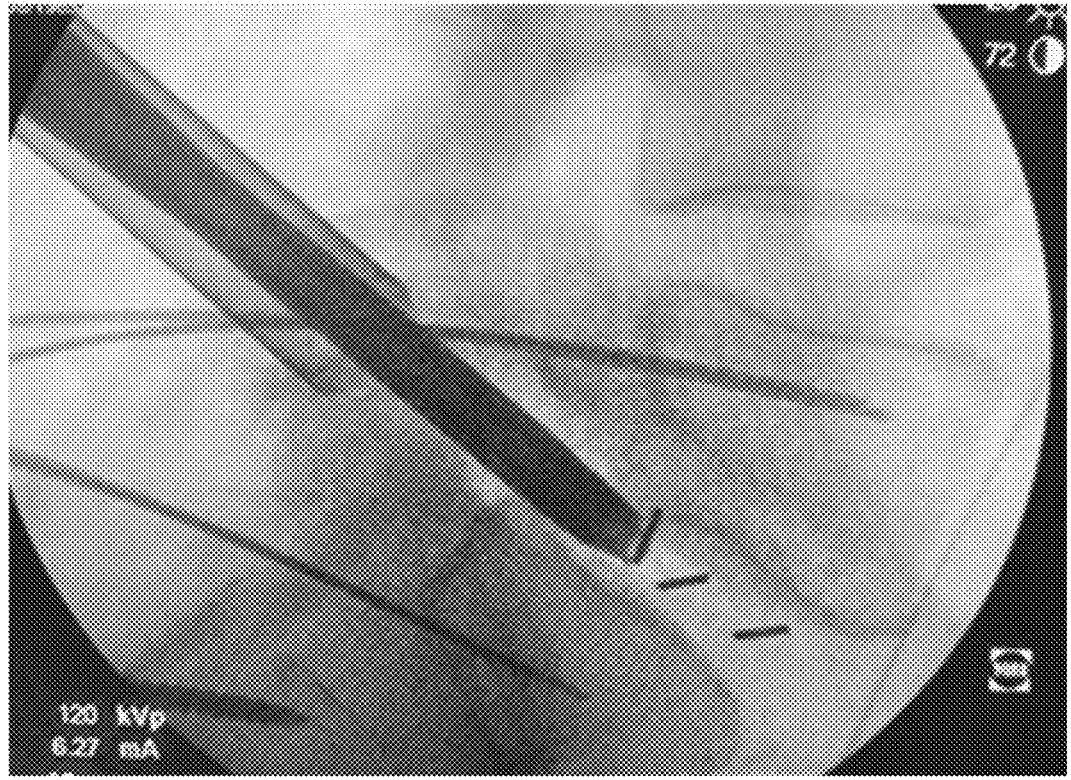
Figure 32A:
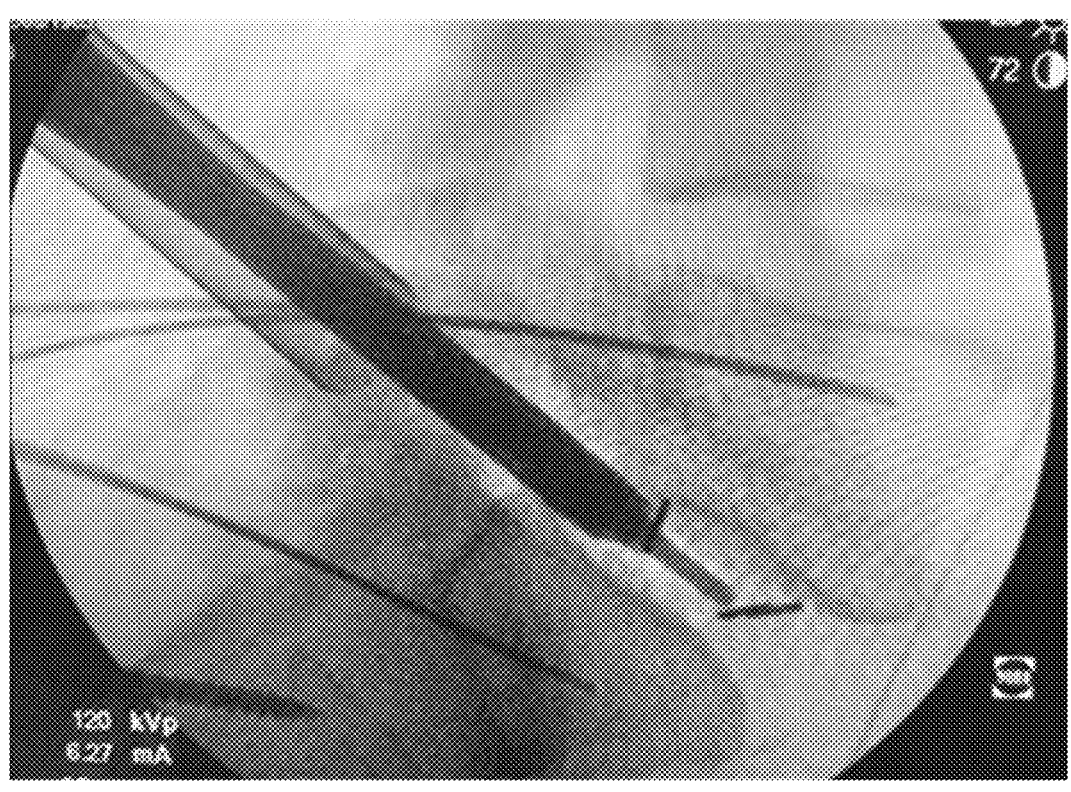
FIGS. 32A, 32B, 32C, 32D, and 32E illustrate expansion of the expandable cage within the disc space and filling of the expanded cage with graft material in accordance with embodiments of the disclosure.
Figure 32B:
Figure 32C:
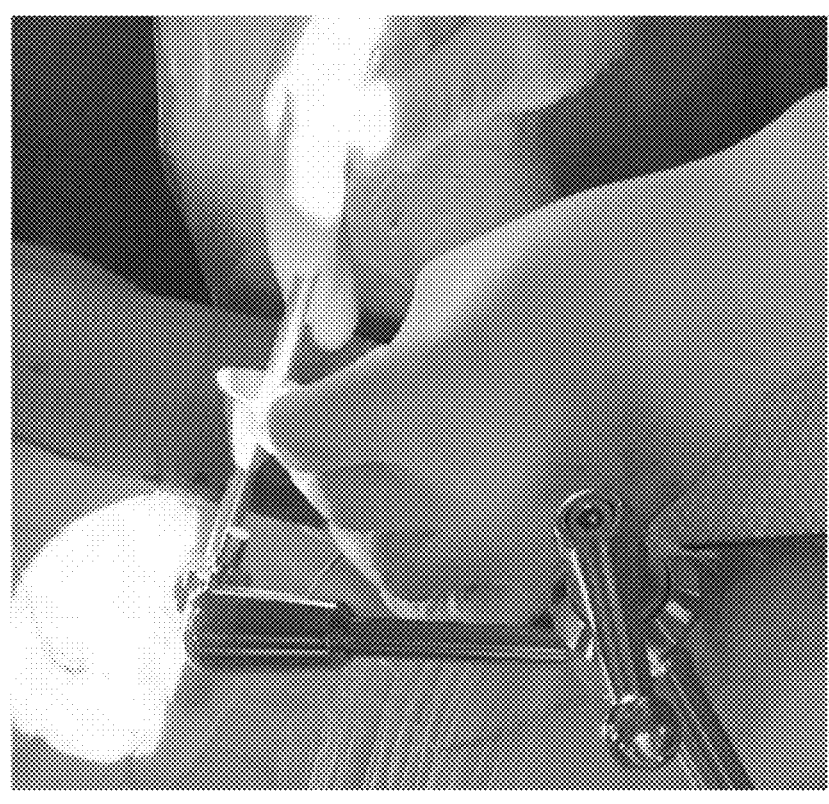
Figure 32D:
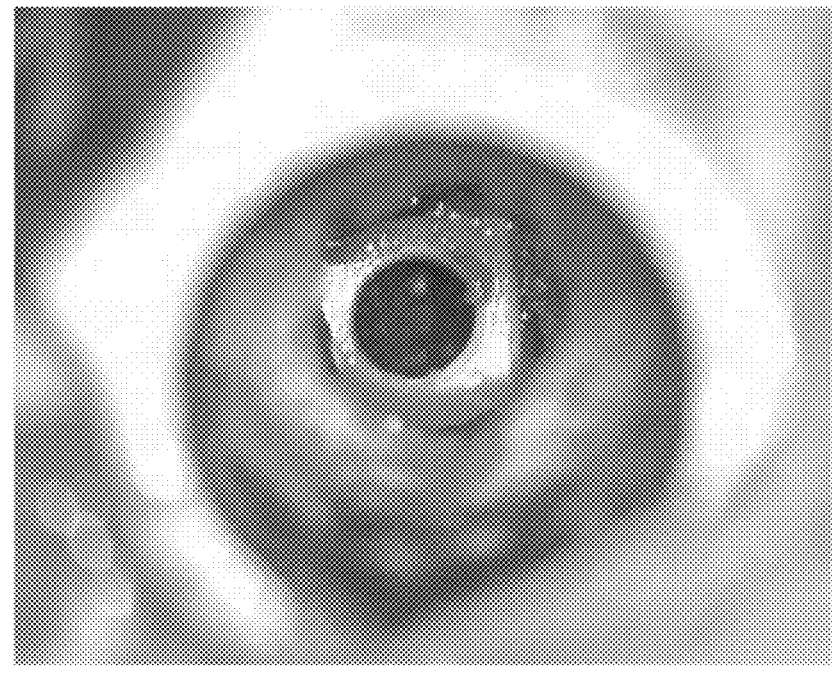
Figure 32E:
Figure 33A:
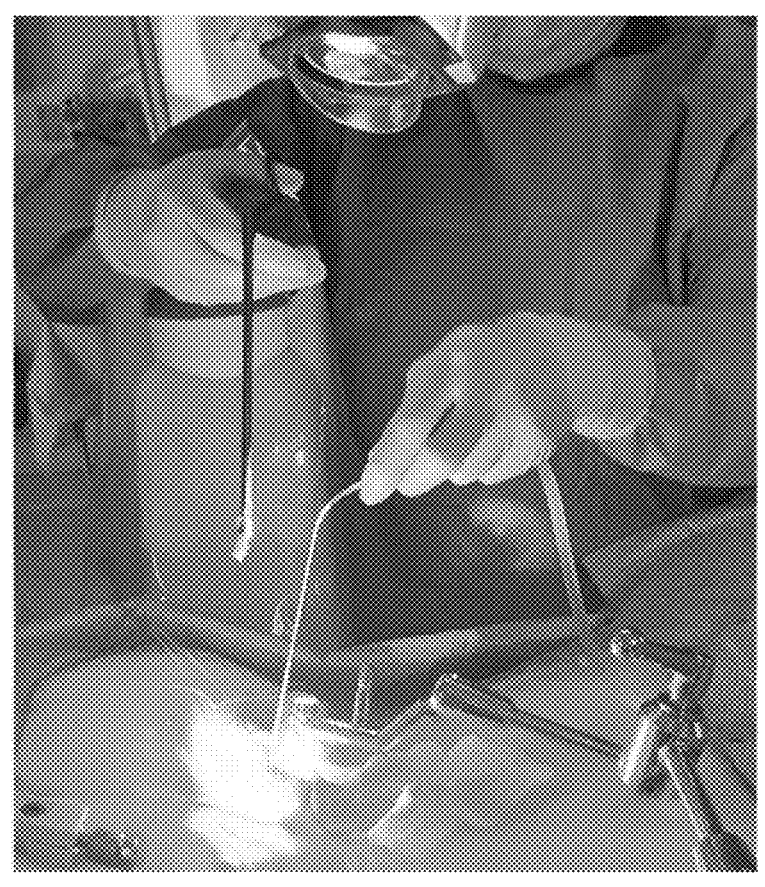
FIGS. 33A and 33B illustrate placement of additional graft material behind the expanded cage up to the entry point of the facet joint in accordance with embodiments of the disclosure.
Figure 33B:
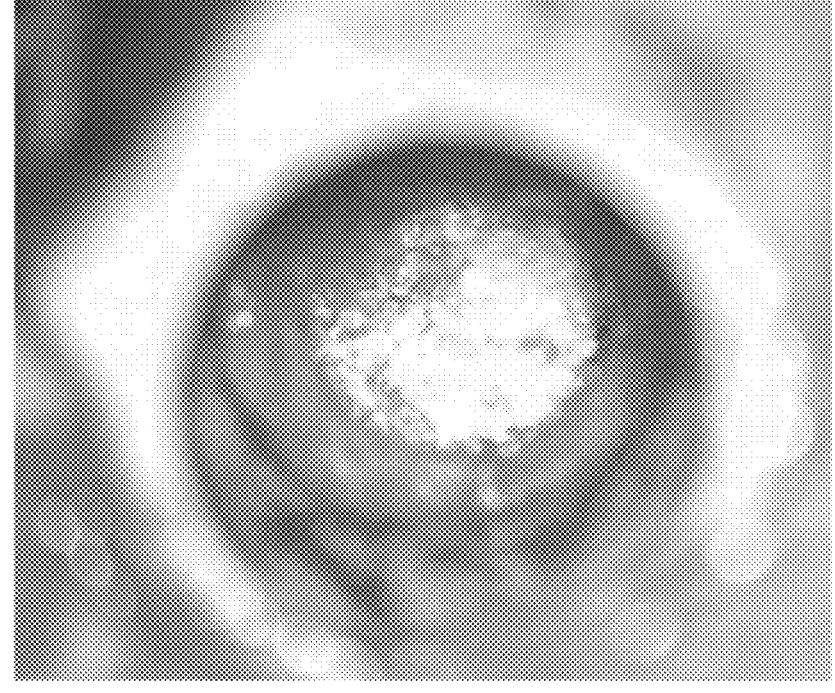
Figure 34A:
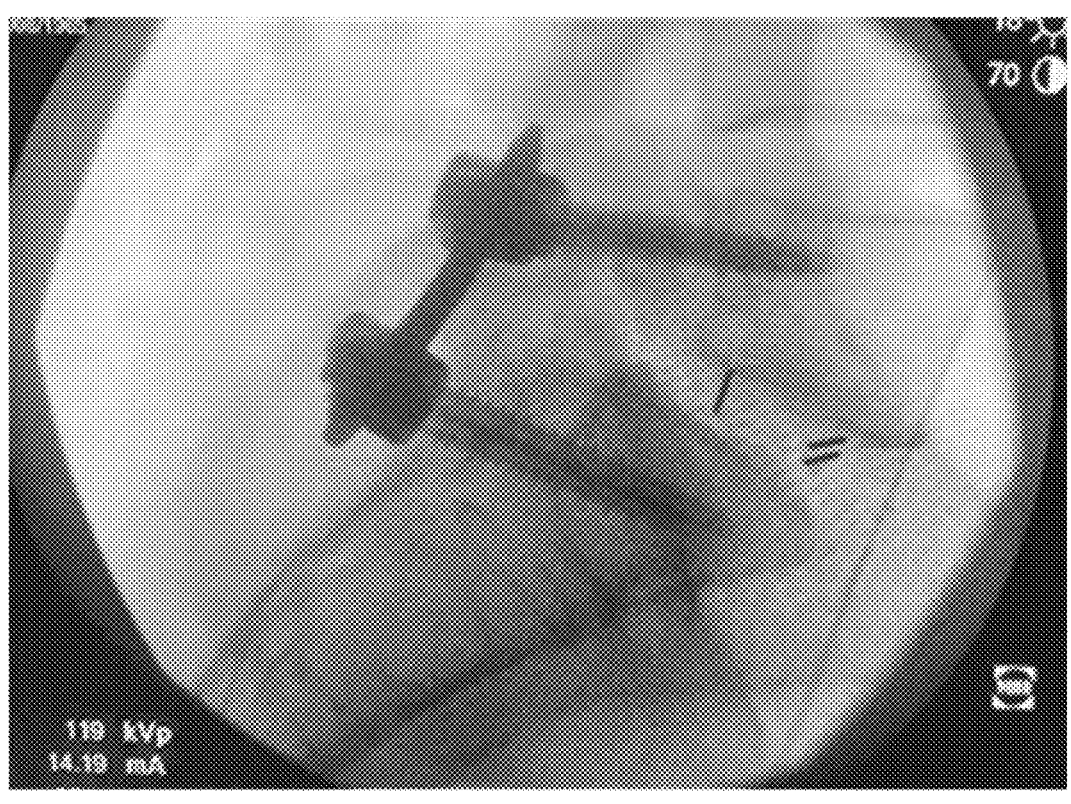
FIGS. 34A and 34B illustrate placement of pedicle screws and rods in accordance with embodiments of the disclosure.
Figure 34B:
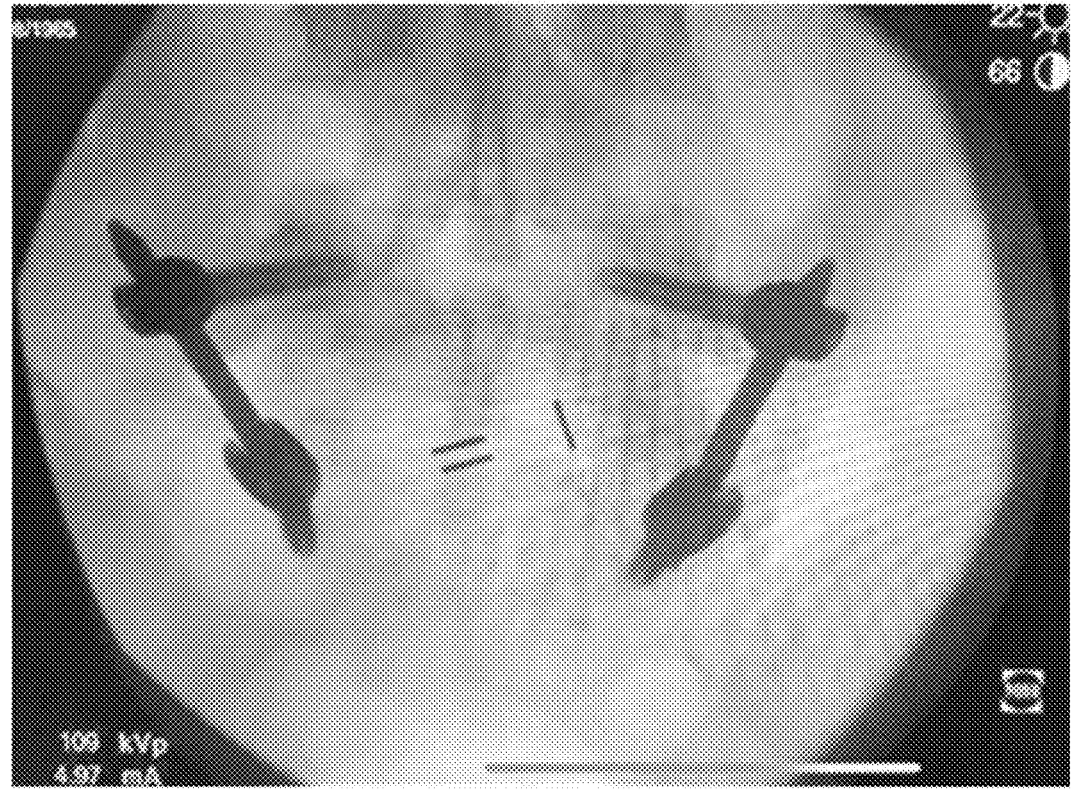
Figure 35A:
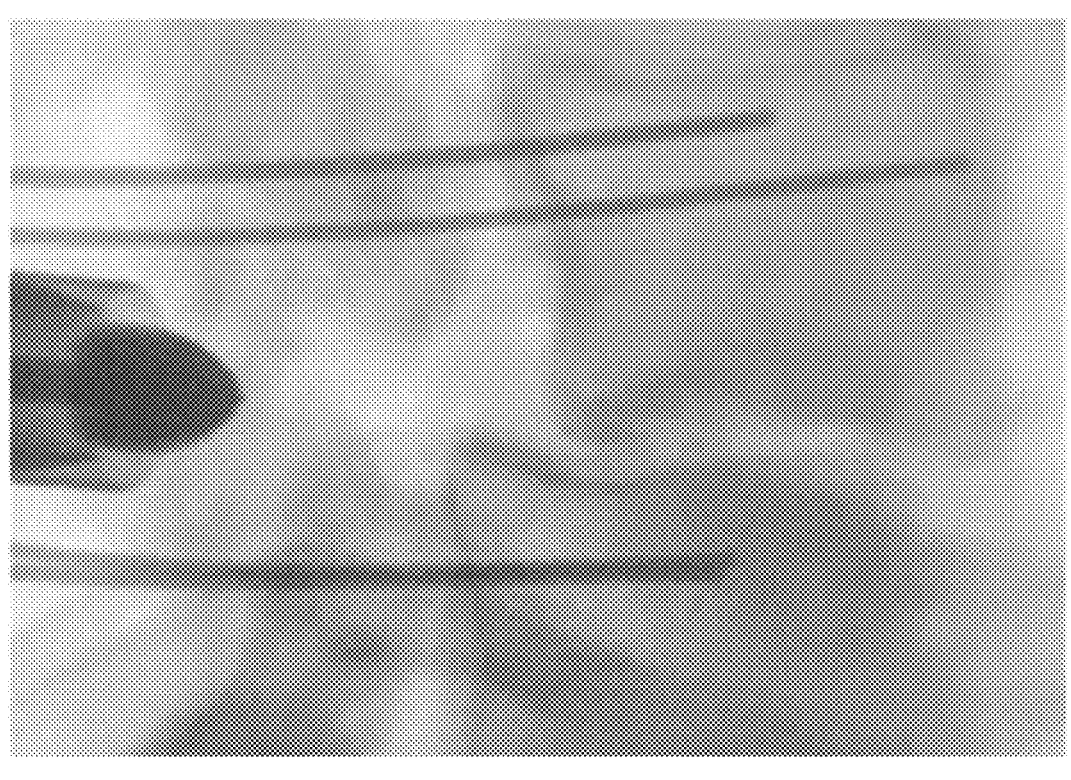
FIGS. 35A and 35B illustrate introduction of the drill with the acorn drill bit through the reducer dilator tube in accordance with embodiments of the disclosure.
Figure 35B:
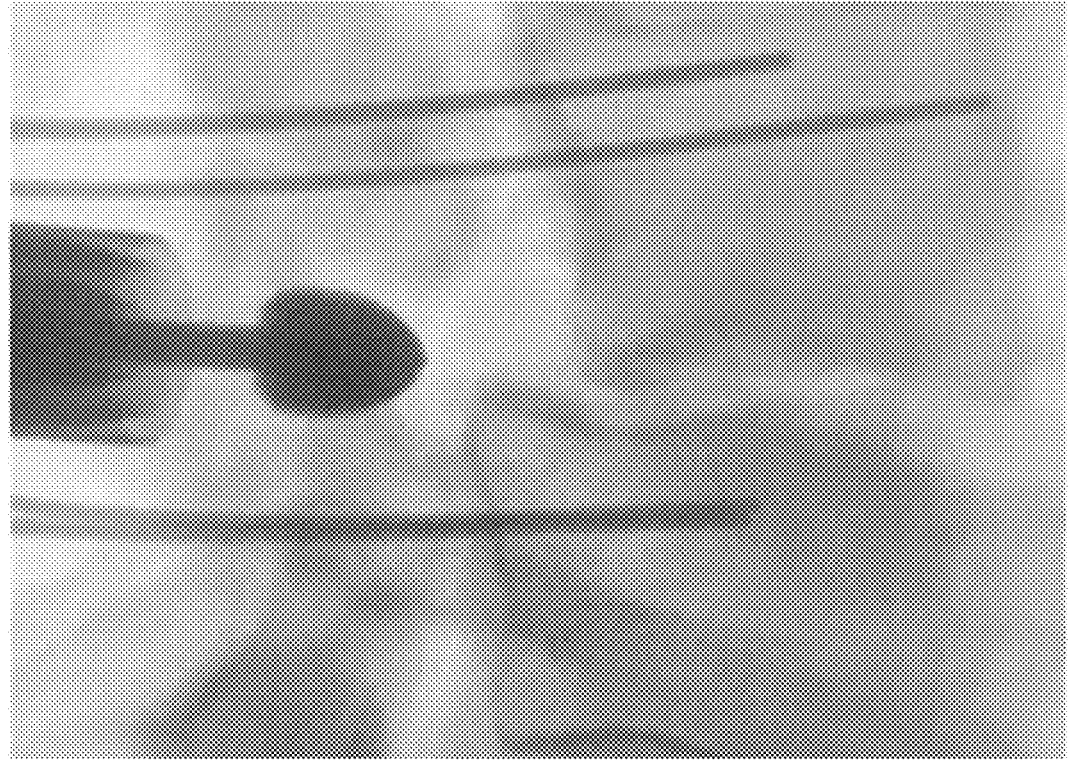
Figure 36A:
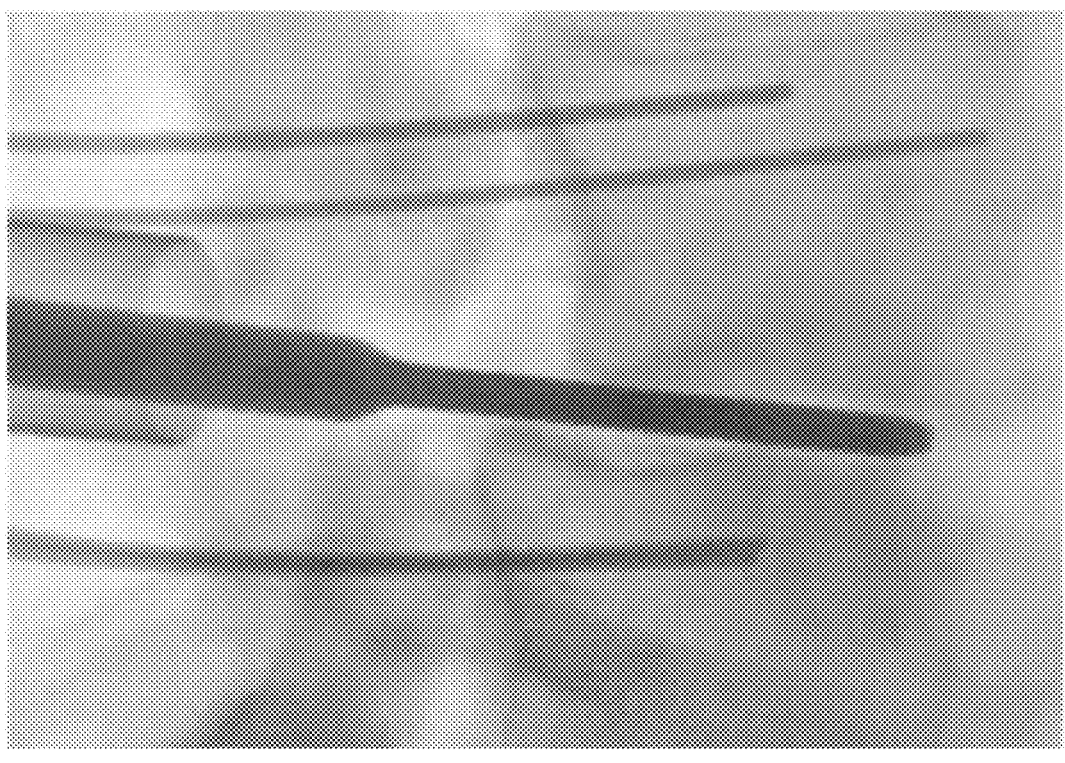
FIGS. 36A and 36B illustrate sequential introduction of the distractors to open up the collapsed disc space in accordance with embodiments of the disclosure.
Figure 36B:
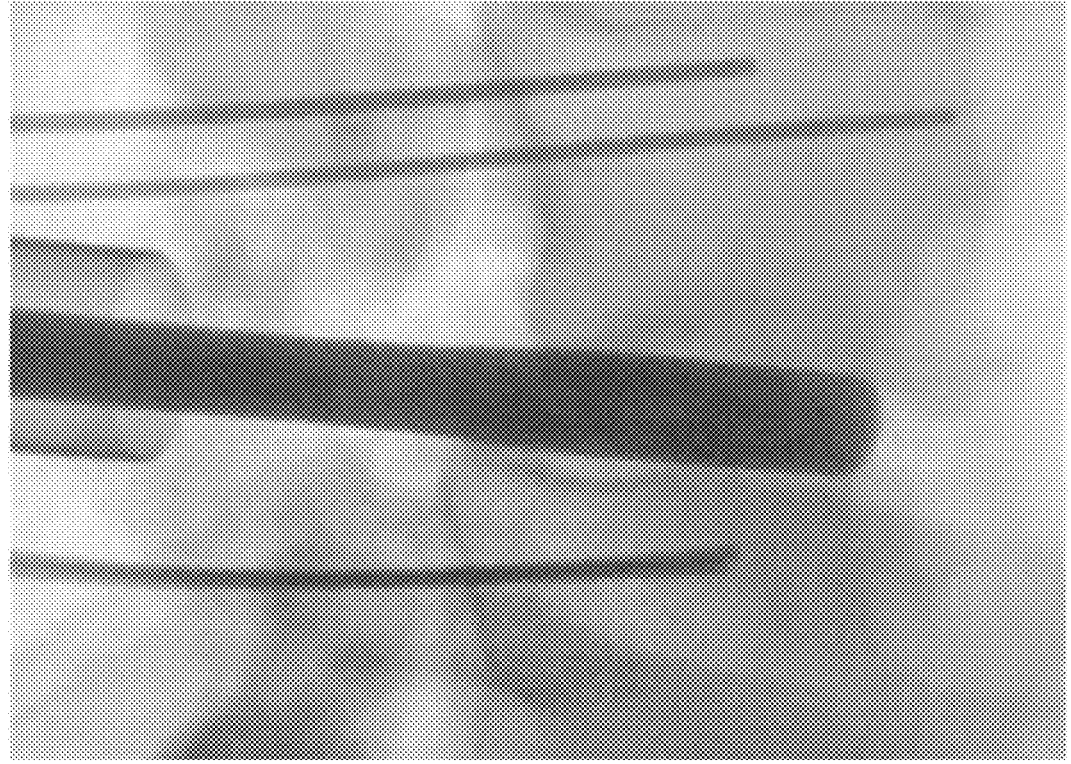
Figure 46:
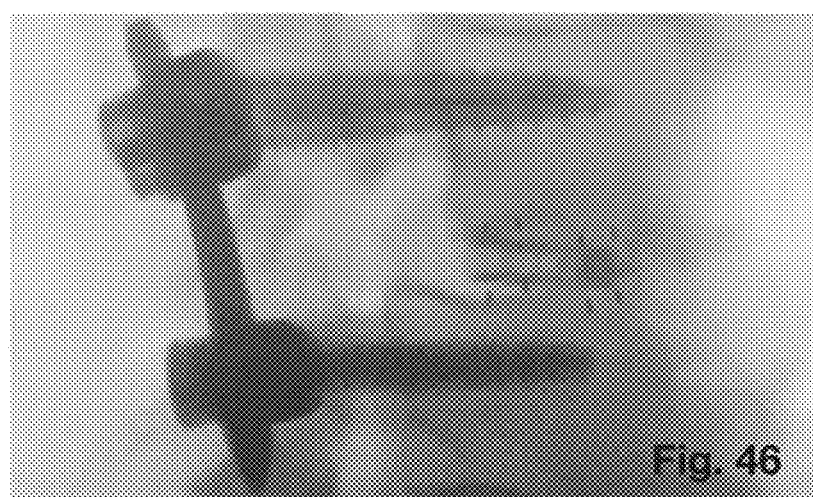
FIG. 46 illustrates placement of pedicle screws and rods in accordance with embodiments of the disclosure.

The next step may be to use a wedge trial or sizing instrument inside the disc space to determine the exact size of the cage to be used (FIGS. 29A-C, 41, 42, 43). The surgeon may use different sizes of expandable PEEK and titanium cages (FIGS. 30A and 30B). The present approach may allow for placement of 7×7 mm cages up to 10×10 mm cages upon entry into the interspace, with the ability to expand up to 15 mm in height and 11 mm in width, with lordosis ranging from 0 to 12 degrees. Before placement of the cage, the surgeon may introduce graft material, such as Mastergraft blocks, inside the interspace way anteriorly. The cage may be advanced into the interspace after being pre-filled with graft material, such as Grafton (FIGS. 31A-D and 44A-D). After expansion of the cage within the interspace (FIGS. 32A, 32D, and 45), the cage then may be filled again with Grafton (FIGS. 32B, 32C, 32E, and 45). Z-LIF plus then may be executed at this stage in patients with severe spinal stenosis with the use of a diamond drill under direct microscopic or endoscopic vision. The surgeon may also elect at this stage to excise the ligamentum flavum and/or directly decompress the distal nerve root as indicated. Mastergraft then may be placed behind the cage all the way up to the entry point of the facet joint, achieving interbody fusion behind the cage as well as facet fusion (FIGS. 33A and 33B). The latter step may be eliminated if the nerve root itself is exposed subsequent to the decompression so as not to cause any chance of the resultant facet fusion causing any compression or irritation of the nerve root. The access tube then may be removed. The surgeon then may be place pedicle screws, such as Solera Sextant percutaneous pedicle screws, and percutaneous rods around the pedicle screw wires introduced previously as outlined above (FIGS. 34A, 34B, 46).

Figure 47A:
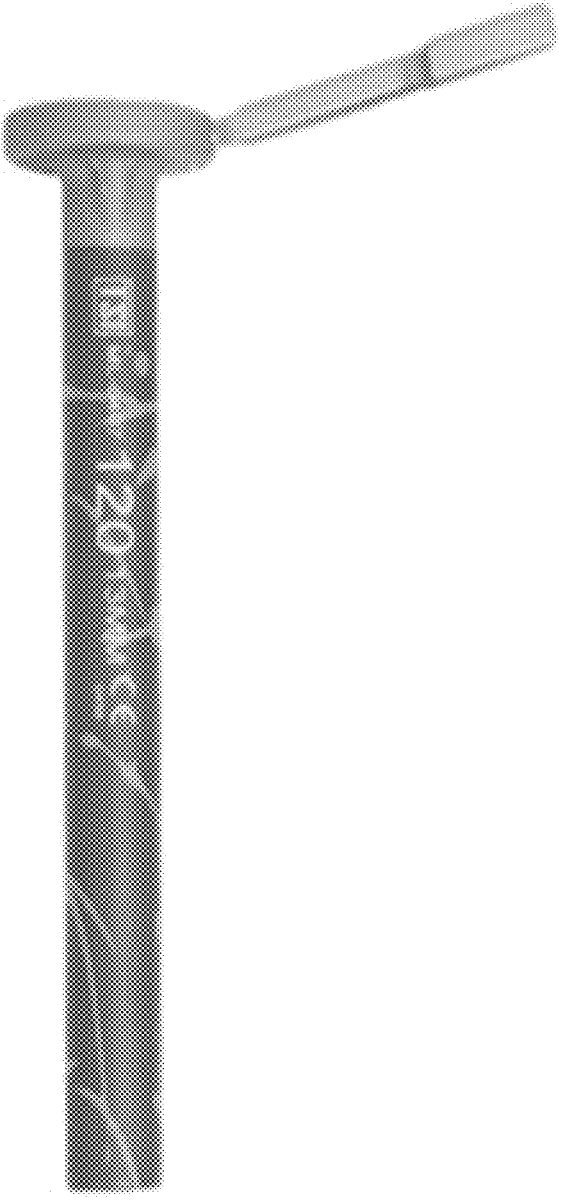
FIG. 47A illustrates a Phantom ML minimal access tube as may be used in accordance with embodiments of the disclosure.

As mentioned above, different minimal access tubes of different sizes may be used for the present technique. In some embodiments, a 13 mm diameter radiolucent Phantom ML tube (FIG. 47A may be used. This is the smallest diameter tube currently in the market that is large enough to allow for placement of the desired rectangular and cylindrical expandable cages. It is at the same time small enough to prevent any muscle creep from the paraspinal muscles. Additionally, it is radiolucent and thus allows for fluoroscopic images to be obtained even through the tube itself. Further, it is the smallest tube available that allows for excellent microscopic visualization as well as endoscopic visualization. It has its own side lights for enhanced visualization. This tube also has its own reducer dilator tube that allows for an exact fit for the Midas Rex 9 mm Acorn drill bit attachment.

Figure 47B:
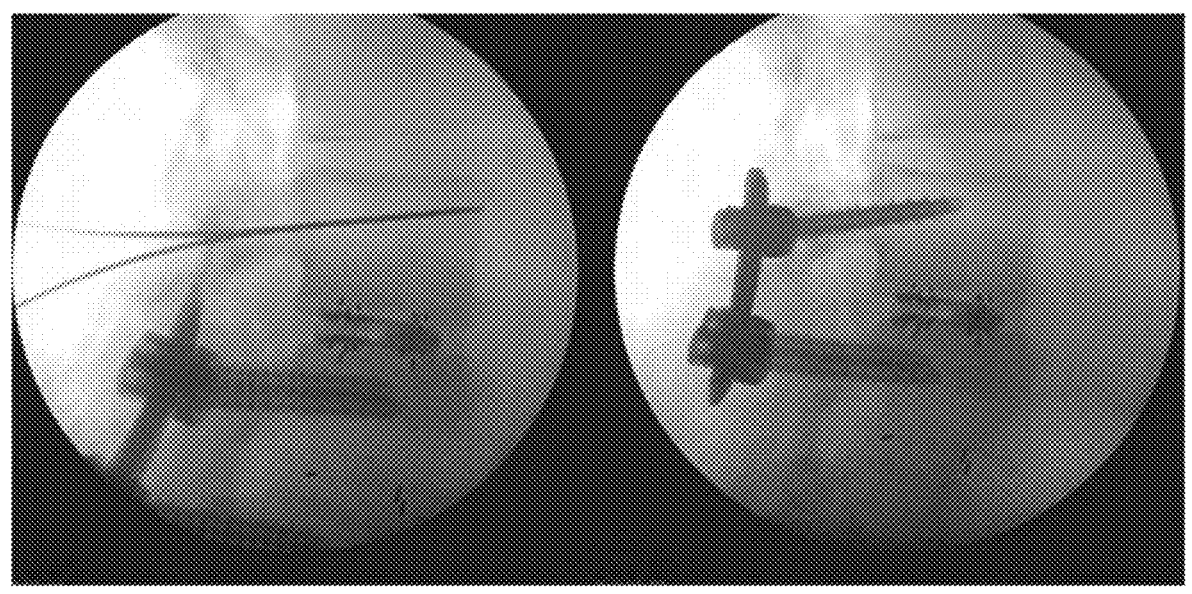
FIGS. 47B and 47C illustrate placement of Flare Hawk expandable cages, pedicle screws, and rods in accordance with embodiments of the disclosure.
Figure 47C:
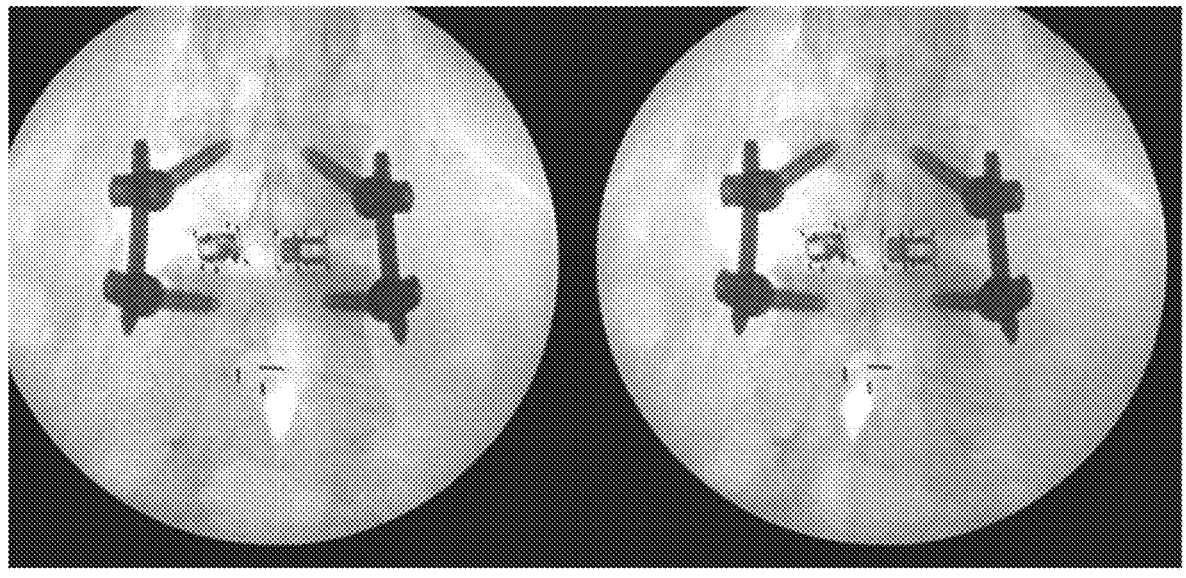
Figure 47D:
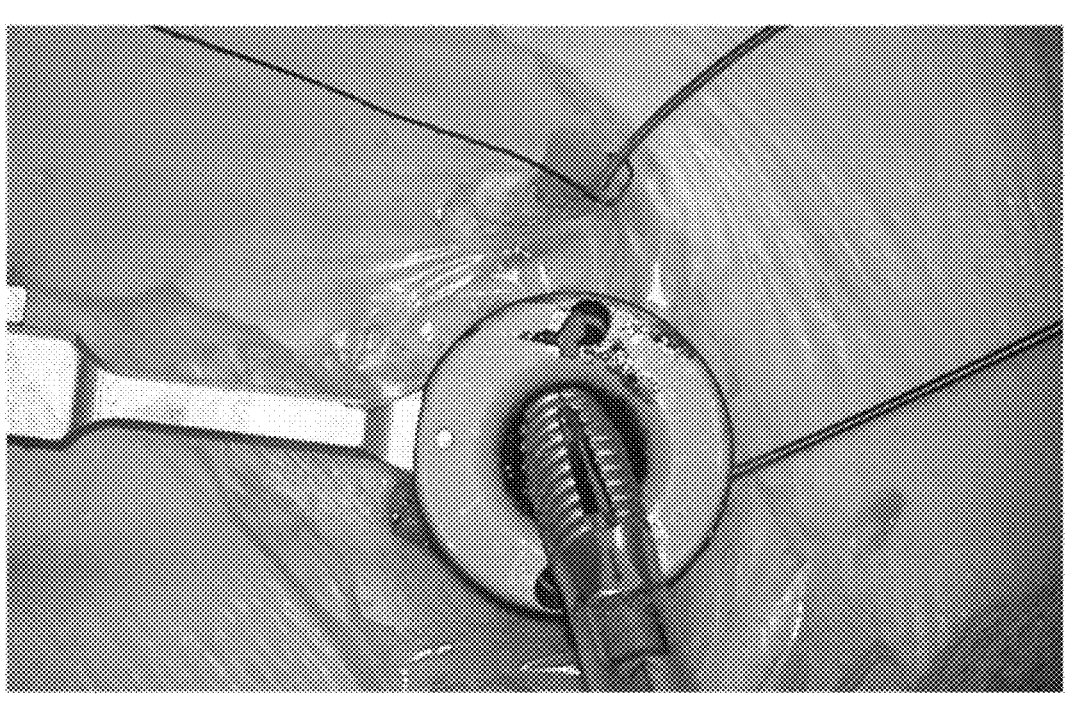
FIGS. 47D, 47E, 47F, 47G, 47H, and 47I illustrate placement of VariLift expandable cages, pedicle screws, and rods in accordance with embodiments of the disclosure.
Figure 47E:
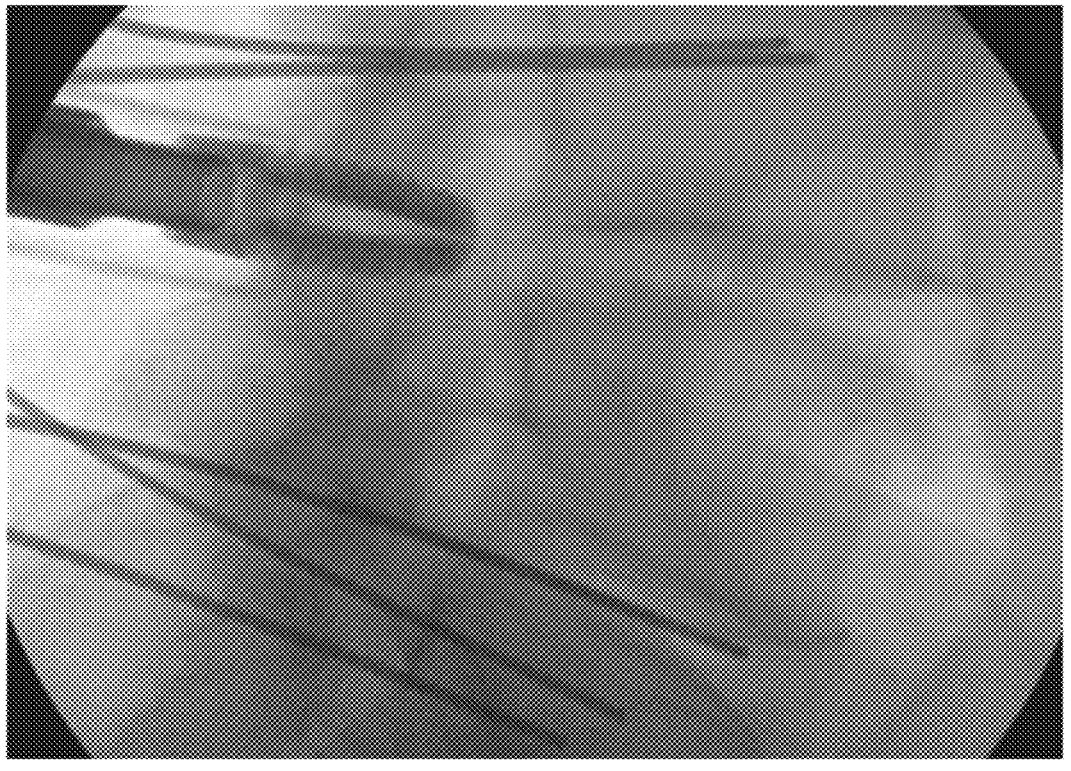
Figure 47F:
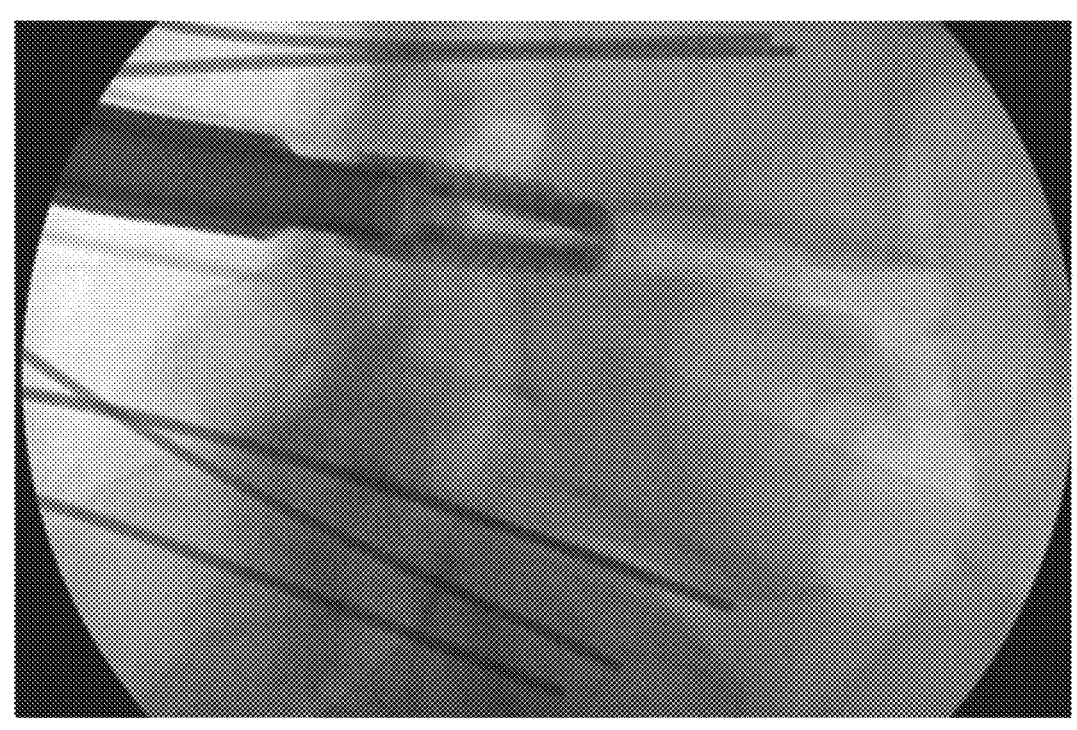
Figure 47G:
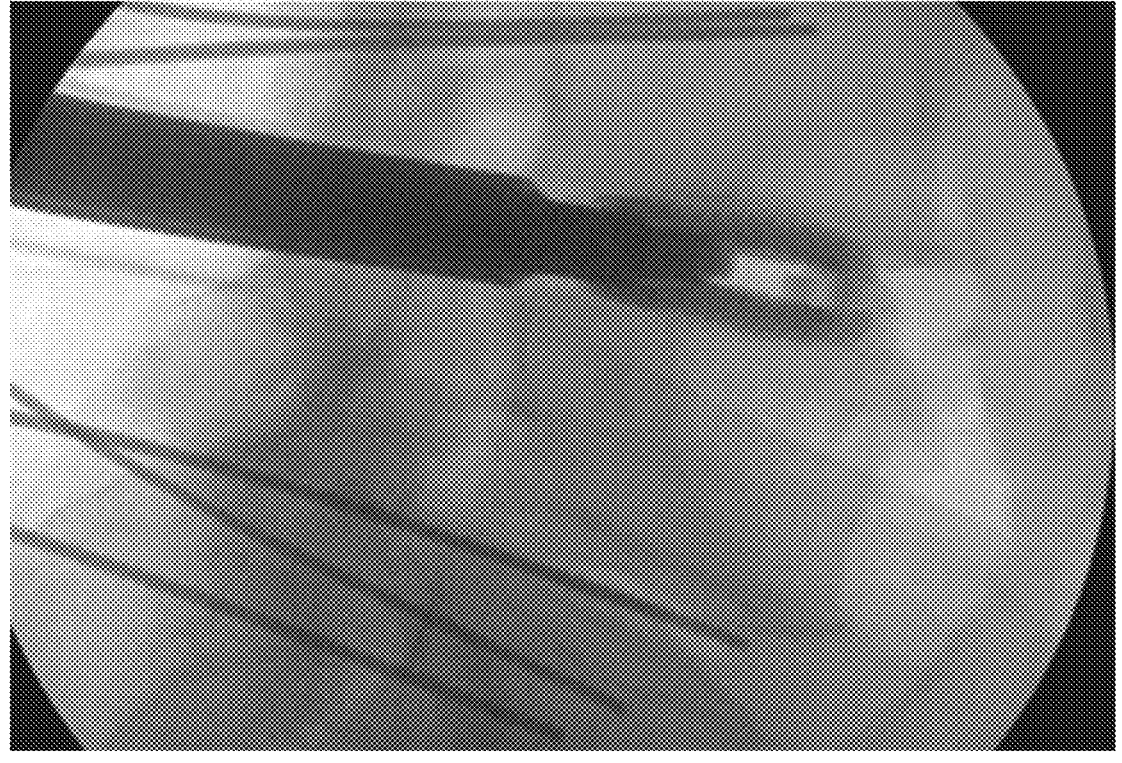
Figure 47H:
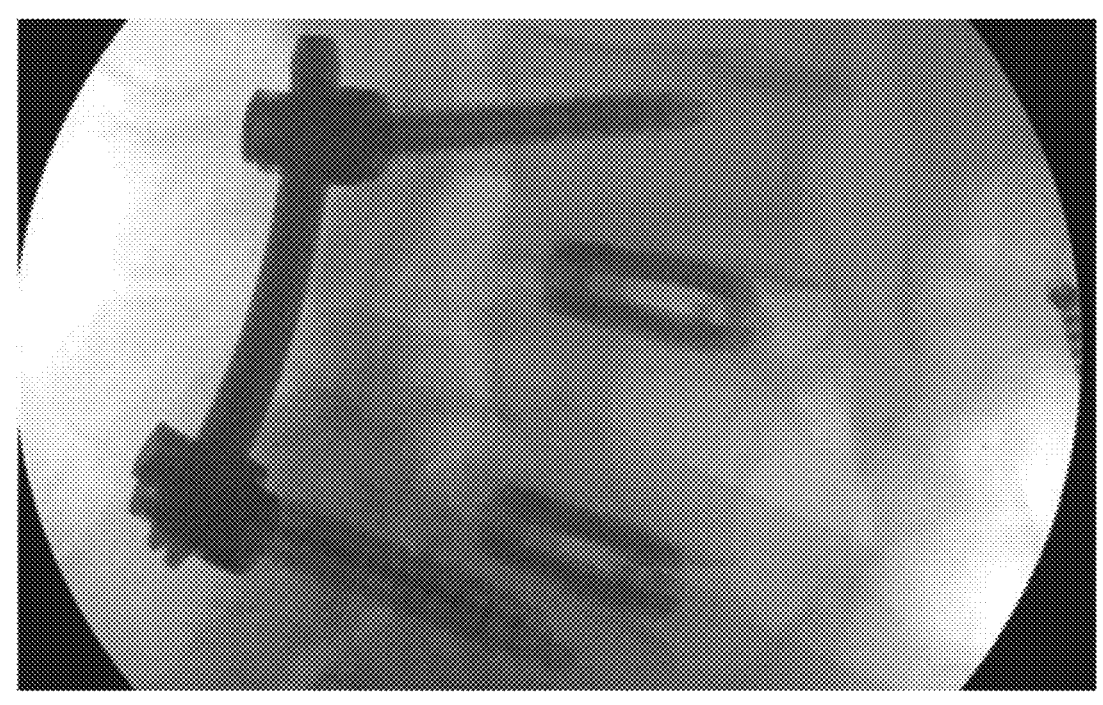
Figure 47I:
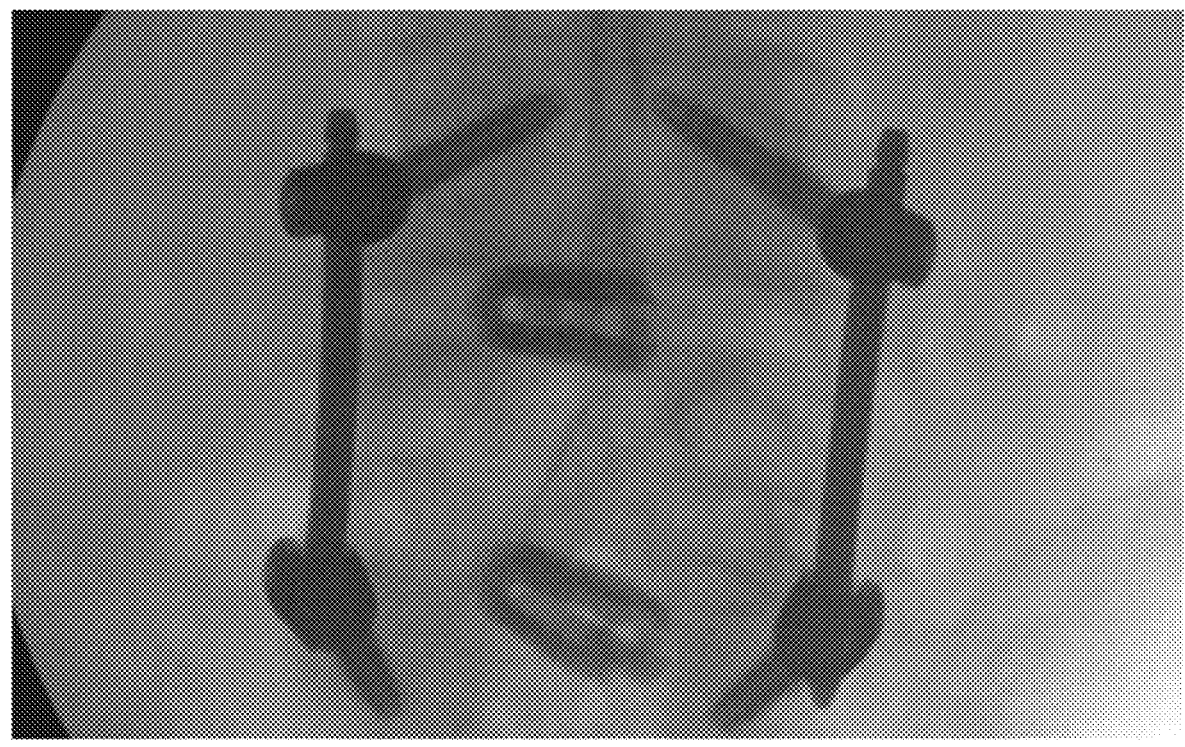
Figure 47J:
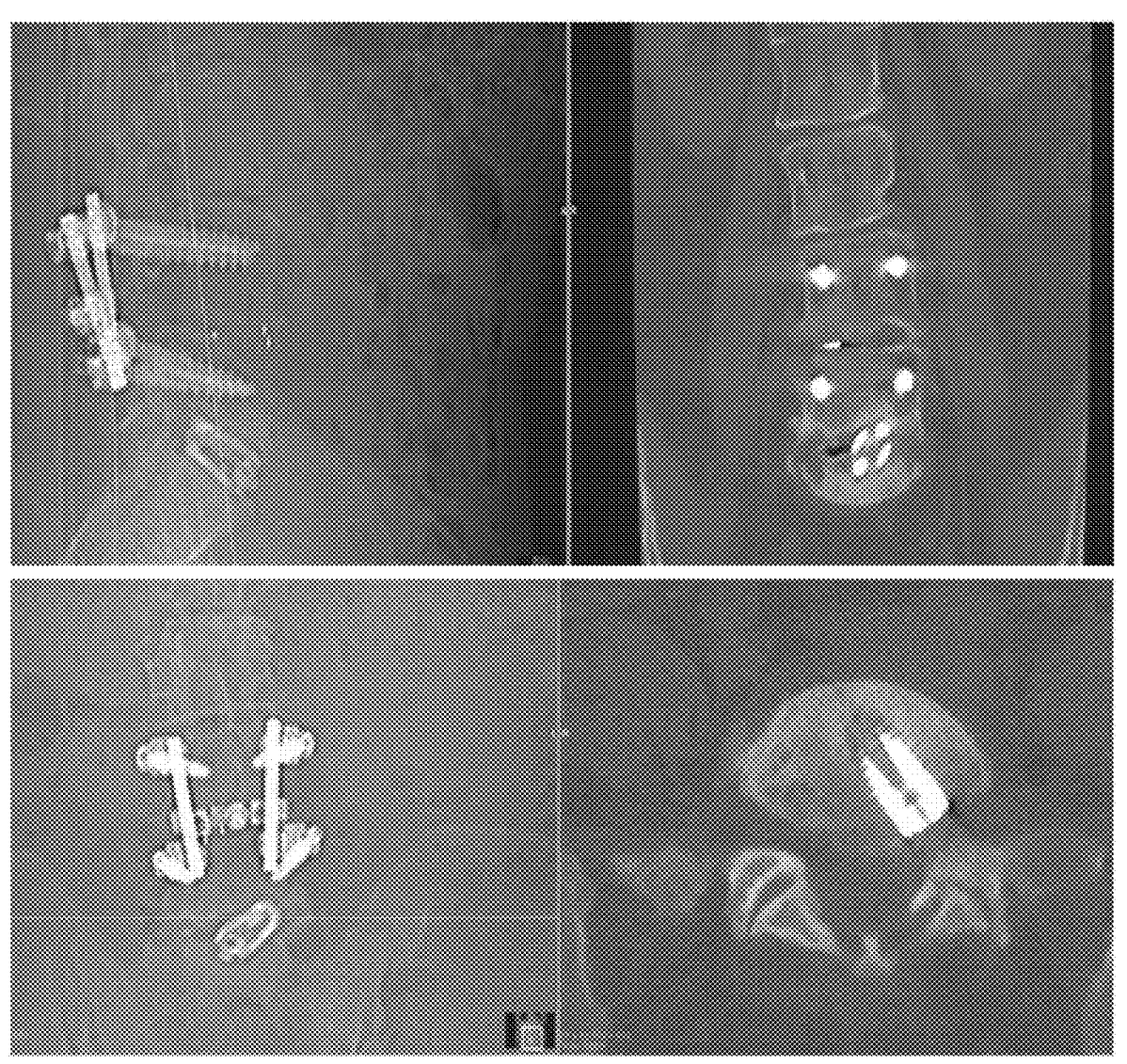
FIGS. 47J and 47K illustrate placement of VariLift expandable cages in a stand-alone fashion in accordance with embodiments of the disclosure.
Figure 47K:
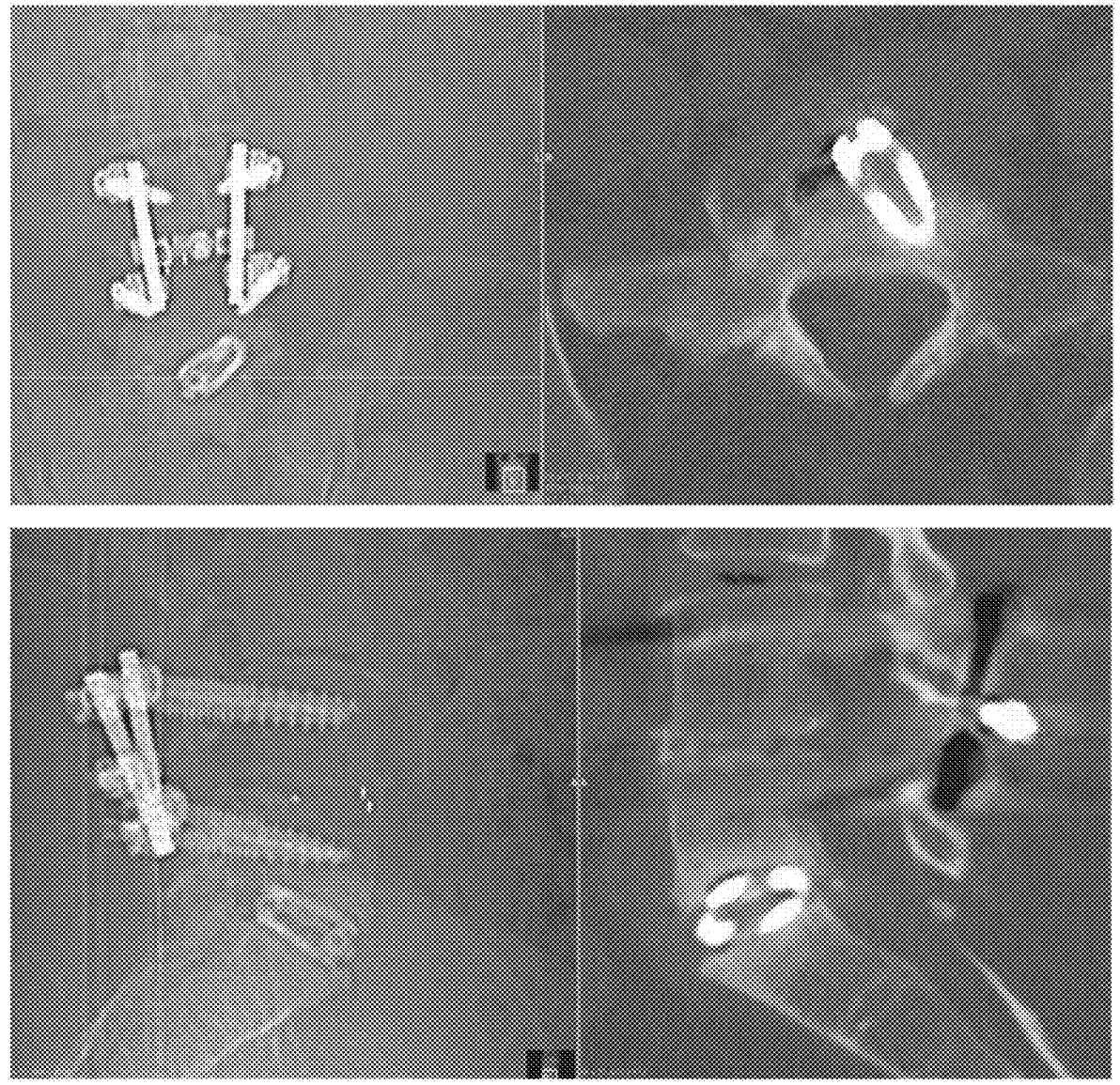

Various different sizes and types of cages may be used for the present technique. Expandable rectangular and cylindrical cages that are small enough to pass through a 10 mm diameter opening in the mid-facet region may be advantageous for safety and function. In some embodiments, a 7×7 mm expandable rectangular cage may be used. For example, the 7×7 mm Flare Hawk cage, which expands well in height and width and can maintain lordosis, may be used. The Flare Hawk cage has been used successfully as a single cage crossing the midline at L4-5 and L5-S1 as well as bilaterally at L3-4 (FIGS. 47B and 47C). In some embodiments, the 10 mm expandable titanium VariLift cage may be used. It also expands in height and width and can maintain lordosis. The VariLift cage has been used successfully, mostly with pedicle screws (FIGS. 47D-I) as well as in a stand-alone fashion (FIGS. 47J and 47K).

Various systems of pedicle screws and rods may be used in conjunction with the Z-LIF procedure. In some embodiments, the Sextant pedicle screw system may be used. It is minimally invasive and also easy to remove using the minimal access tubes.

Discussion

Figure 48:
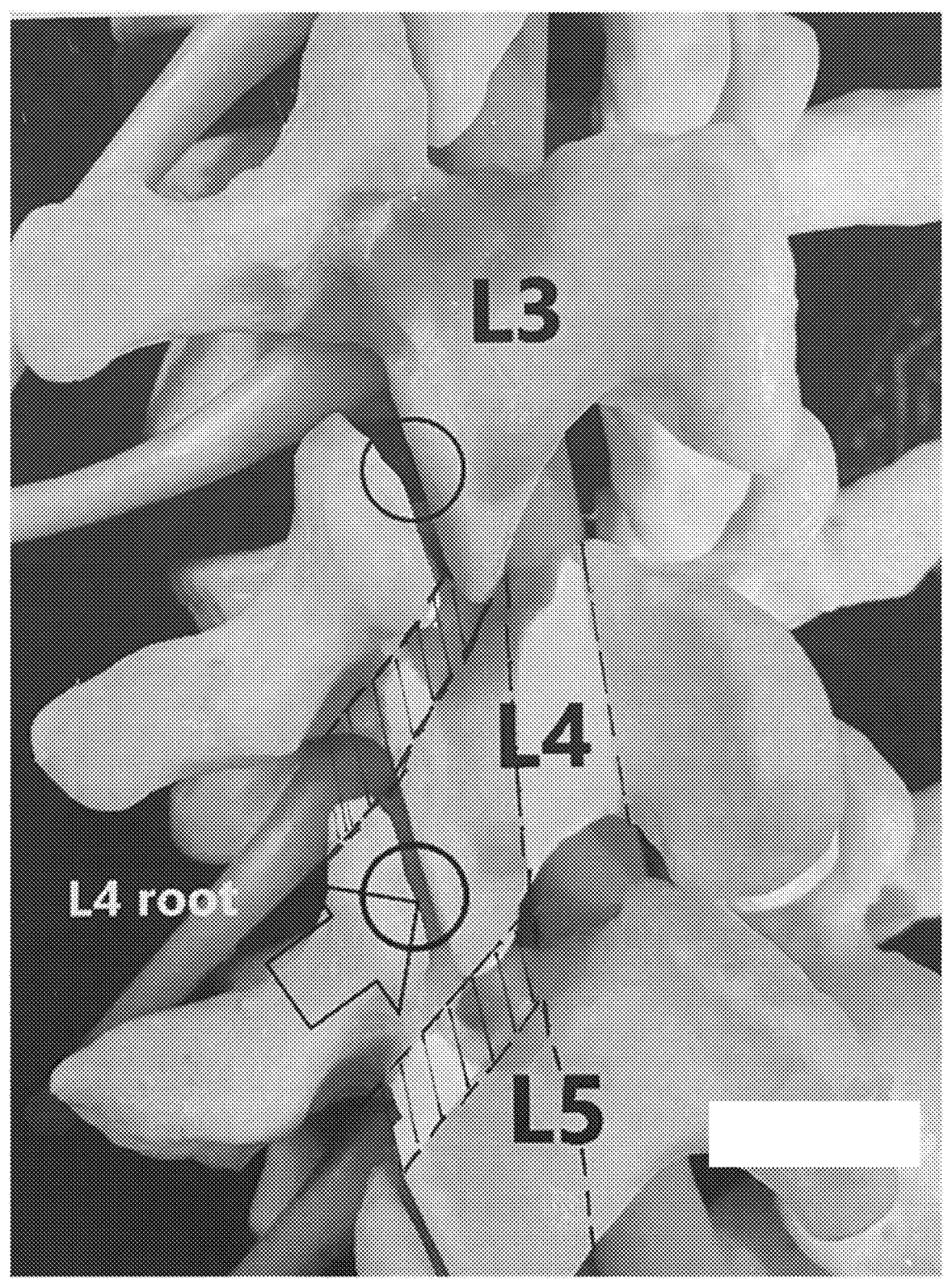
FIG. 48 illustrates a lumbar portion of a spine, showing facet joints, nerve roots, and the thecal sac of the spine.

With the creation of a corridor within the facet joint using the present technique, the surgeon may protect the nerve root above it as well as the thecal sac medial to it (FIG. 48). The surgeon may be most successful in the approach to a disc space when he/she does not even have to encounter any of the neural elements, which is the case with the present technique. Not only does that eliminate the chance of nerve root injury but also even the development of epidural scarring or arachnoiditis. With this novel Trans-Facet approach, the surgeon may enter into the middle of the facet joint midway between the superior and inferior articular processes, creating a corridor towards the disc space. This leaves a few millimeters of circumferential bony protection between the exposure and the nerve roots above and below. In addition, there is an additional 1 to 2 mm of the fibrous capsule of the facet joint especially superiorly. The safety of this approach may be enhanced by the size of the facet joints, which are sometimes hypertrophied in those patients. Basically, the larger the facet joint, the safer this technique is. The safety is further enhanced by using a narrow corridor and the use of a smaller expandable cage. The technology of expandable interbody peek and titanium cages has allowed surgeons to create such a narrow corridor into the disc space. Not only do we now have expandable cages in terms of height, but we also have expandable cages in terms of width. With the current instrumentation available today, the surgeon can use 13 mm, 14 mm, and 16 mm minimal access tubes. Visualization through the tube via microscopy or endoscopy may be employed for safety. In the last 21 cases performed by the present inventor, visualization via microscopy did not reveal the exposure of any of the nerve roots or the thecal sac. This evidences that the present technique renders itself to the use of a strictly percutaneous exposure.

Accuracy of the approach depends on a preoperative Lumbar MRI or post myelogram CT scan to study the anatomy of the approach. A preoperative Lumbar CT scan in the prone position may be preferable. An accurate robotic system fixed to the table and/or the floor may be particularly advantageous. The patient well fixed into the Jackson table also may be important. A navigation system and navigated instruments also are advantageous, along with live fluoroscopy with AP, lateral, and oblique trajectories to verify the approach. Navigation helps to verify the robotic approach; however, it is not 100% accurate. Finally, it is advantageous to visualize the approach by an intra-operative microscope or endoscopy.

The present trans-facet technique, with the creation a corridor in the middle aspect of the facet joint, is unique and totally different from other techniques of posterior lumbar interbody fusion involving the facet joints. PLIF invariably necessitates a medial partial facetectomy (FIG. 49) with a hemilaminectomy performed as well as drilling of the medial aspect of the inferior articular process. TLIF may or may not need a lateral partial facetectomy (FIG. 50). TLIF procedures are also done using a total facetectomy whether open or via a tubular system. This may further expose the neural elements which can be subject to injury or scarring. Creation of a corridor in the middle of the facet joint midway between the superior and inferior articular processes is therefore not an approach employed in PLIF or TLIF.

Figure 49:
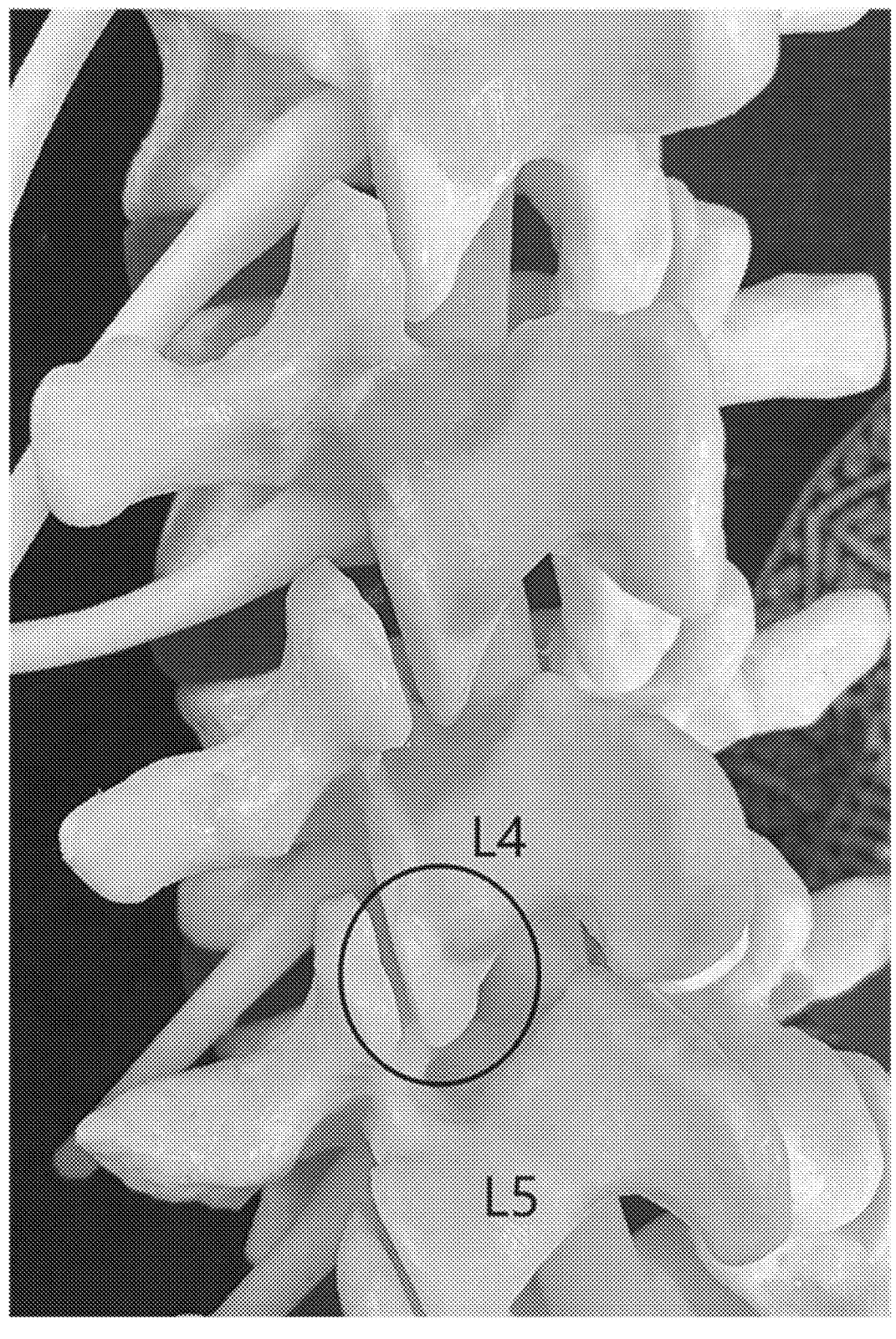
FIG. 49 illustrates a lumbar portion of a spine, showing a facet joint of the spine and indicating how a PLIF may necessitate a medial partial facetectomy.
Figure 50:
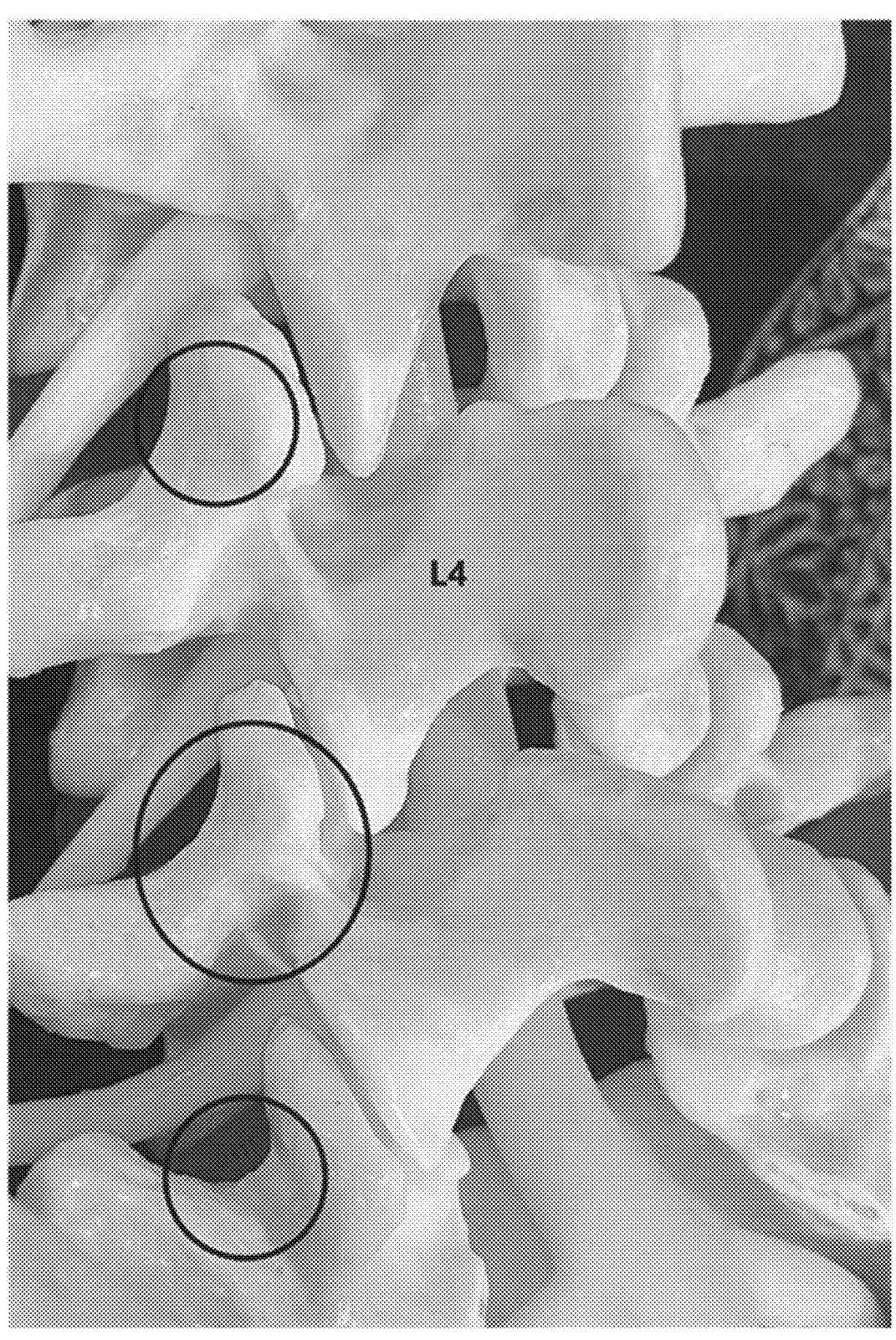
FIG. 50 illustrates a lumbar portion of a spine, showing a facet joint of the spine and indicating how a TLIF may necessitate a lateral partial facetectomy.

The PLIF technique requires exposure of the thecal sac as well as the shoulder of the lower exiting nerve root with some degree of retraction of the latter (FIG. 49). The TLIF technique through Kambin's triangle involves at least exposure of and perhaps some degree of retraction of the upper exiting nerve root (FIG. 50). Both PLIF and TLIF therefore put those nerve roots at risk of injury at worst, and at best the high chance of epidural scarring and fibrosis with subsequent neuropathic pain.

The use of robotic technology has allowed surgeons to save operative time without compromising accuracy. The planning portion of the procedure can be carried out a few days before surgery as opposed to using an intraoperative CT or O arm and perform the planning during surgery. If a robotic system is not available, however, the use of a CT or MRI or O-Arm guided navigation may be a good alternative and may be considered an integral element in this surgery. As technology develops further and with the advent of more navigated instrumentation, the surgeon may be able to eliminate fluoroscopy altogether and further reduce radiation exposure to the surgeons as well as the OR crew. The present approach provides for an excellent potential for the development of an elaborate highly intelligent autonomous robotic system, hopefully in the near future.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. A method for implanting an interbody device, the method comprising:
    forming an access corridor through an aspect of a facet joint of a patient between an inferior articular process of a vertebra above a disc space of the patient and a superior articular process of a vertebra below the disc space such that an aspect of the inferior articular process is preserved on a medial side of the access corridor and an aspect of the superior articular process is preserved on a lateral side of the access corridor, forming the access corridor comprising:

advancing a first drill bit through the aspect of the facet joint;
advancing a first threaded tap through the aspect of the facet joint, wherein the first threaded tap has a greater diameter than the first drill bit;
advancing a second threaded tap through the aspect of the facet joint, wherein the second threaded tap has a greater diameter than the first threaded tap; and
advancing a second drill bit through the aspect of the facet joint, wherein the second drill bit has a greater diameter than the second threaded tap;
removing disc material from the disc space of the patient via one or more instruments advanced through the access corridor; and
advancing the interbody device through the access corridor and into the disc space.

2. The method of claim 1, wherein forming the access corridor comprises using a robotic system, MRI assisted navigation, CT assisted navigation, O-Arm assisted navigation, or fluoroscopic assisted navigation, or any combination thereof.

3. The method of claim 1, wherein advancing the first threaded tap through the aspect of the facet joint comprises advancing the first threaded tap into a posterior third of the disc space.

4. The method of claim 1, wherein advancing the second threaded tap through the aspect of the facet joint comprises advancing the second threaded tap into a posterior third of the disc space.

5. The method of claim 1, wherein the one or more instruments comprises one or more shavers, rongeurs, or curettes.

6. The method of claim 1, wherein the interbody device is expandable from a compact configuration to an expanded configuration, and wherein advancing the interbody device through the access corridor and into the disc space comprises advancing the interbody device through the access corridor and into the disc space while the interbody device is in the compact configuration.

7. The method of claim 6, further comprising expanding the interbody device from the compact configuration to the expanded configuration within the disc space.

8. The method of claim 7, wherein the interbody device has first maximum transverse and vertical dimensions when the interbody device is in the compact configuration and second maximum transverse and vertical dimensions when the interbody device is in the expanded configuration, and wherein the access corridor has third maximum transverse and vertical dimensions,
    wherein at least one of the third maximum transverse and vertical dimensions is greater than the first maximum transverse dimension and/or the first maximum vertical dimension and less than the second maximum transverse dimension and/or the second maximum vertical dimension.

9. The method of claim 8, wherein expanding the interbody device from the compact configuration to the expanded configuration comprises placing graft material within the interbody device.

10. The method of claim 9, wherein placing graft material within the interbody device comprises placing graft material within the interbody device before advancing the interbody device through the access corridor and into the disc space.

11. The method of claim 9, wherein placing graft material within the interbody device comprises placing graft material within the interbody device after expanding the interbody device within the disc space.

12. The method of claim 9, wherein expanding the interbody device from the compact configuration to the expanded configuration comprises incrementally adding additional graft material within the interbody device.

13. The method of claim 12, further comprising placing graft material within the access corridor.

14. The method of claim 13, wherein placing graft material within the access corridor comprises placing graft material between the interbody device and an entry point of the access corridor.

15. The method of claim 13, further comprising expanding the interbody device within the disc space, wherein placing graft material within the access corridor comprises placing graft material within the access corridor after expanding the interbody device within the disc space.

16. The method of claim 1, wherein the aspect of a facet joint through which the access corridor is formed is positioned closer to one of the inferior articular process of the vertebra above the disc space or the superior articular process of the vertebra below the disc space than the other of the inferior articular process of the vertebra above the disc space or the superior articular process of the vertebra below the disc space.

17. The method of claim 1, further comprising:

decompressing a portion after advancing the interbody device through the access corridor and into the disc space, decompressing a portion.

18. The method of claim 17, further comprising at least one of:

excising a ligamentum flavum adjacent the disc space, or decompressing a distally exiting portion of a nerve root adjacent the disc space.

19. A method for performing spinal surgery, the method comprising:

forming an access corridor through an aspect of a facet joint of a patient between an inferior articular process of a vertebra and a superior articular process of a vertebra such that an aspect of the inferior articular process is preserved on a medial side of the access corridor and an aspect of the superior articular process is preserved on a lateral side of the access corridor, forming the access corridor comprising:

advancing a first drill bit through the aspect of the facet joint;

advancing a first threaded tap through the aspect of the facet joint, wherein the first threaded tap has a greater diameter than the first drill bit;

advancing a second threaded tap through the aspect of the facet joint, wherein the second threaded tap has a greater diameter than the first threaded tap; and advancing a second drill bit through the aspect of the facet joint, wherein the second drill bit has a greater diameter than the second threaded tap; and advancing an interbody device into the access corridor.

20. A method for performing spinal surgery, the method comprising:

forming an access corridor through an aspect of a facet joint of a patient between an inferior articular process of a vertebra and a superior articular process of a vertebra such that an aspect of the inferior articular process is preserved on a medial side of the access corridor and an aspect of the superior articular process is preserved on a lateral side of the access corridor, forming the access corridor comprising:

advancing a first drill bit through the aspect of the facet joint;

advancing a first threaded tap through the aspect of the facet joint, wherein the first threaded tap has a greater diameter than the first drill bit;

advancing a second threaded tap through the aspect of the facet joint, wherein the second threaded tap has a greater diameter than the first threaded tap; and advancing a second drill bit through the aspect of the facet joint, wherein the second drill bit has a greater diameter than the second threaded tap; and placing graft material within the access corridor.

* * * * *